United States Patent
Wilkerson et al.

(10) Patent No.: US 11,285,504 B2
(45) Date of Patent: Mar. 29, 2022

(54) SPRAY EJECTOR DEVICE AND METHODS OF USE

(71) Applicant: Eyenovia, Inc., Tampa, FL (US)

(72) Inventors: Jonathan Ryan Wilkerson, Raleigh, NC (US); Iyam Lynch, Boone, NC (US); Charles Eric Hunter, Boone, NC (US); Joshua Richard Brown, Hickory, NC (US); Louis Thomas Germinario, Kingsport, TN (US); James Thornhill Leath, Burlington, NC (US); Nathan R. Faulks, Boone, NC (US); Kris Grube, Boone, NC (US); Matthew Ditrolio, Boone, NC (US); J. Sid Clements, Boone, NC (US)

(73) Assignee: Eyenovia, Inc., New York, NY (US)

( * ) Notice: Subject to any disclaimer, the term of this patent is extended or adjusted under 35 U.S.C. 154(b) by 538 days.

(21) Appl. No.: 15/197,033

(22) Filed: Jun. 29, 2016

(65) Prior Publication Data
US 2017/0136484 A1 May 18, 2017

Related U.S. Application Data

(63) Continuation of application No. 13/866,783, filed on Apr. 19, 2013, now abandoned.
(Continued)

(51) Int. Cl.
*B05B 17/00* (2006.01)
*B05B 17/06* (2006.01)
(Continued)

(52) U.S. Cl.
CPC ........ *B05B 17/0646* (2013.01); *A61F 9/0008* (2013.01); *A61M 11/00* (2013.01);
(Continued)

(58) Field of Classification Search
CPC ............ B05B 17/0646; B05B 17/0661; B05B 17/0676; B05B 17/0684; B05B 17/063;
(Continued)

(56) References Cited

U.S. PATENT DOCUMENTS 2,698,619 A * 1/1955 Beacham .................. A61J 1/10
604/408
3,892,235 A * 7/1975 Van Amerongen .........................
A61M 15/0085
128/200.16
(Continued)

FOREIGN PATENT DOCUMENTS

CN  1347349 A   5/2002
CN  1854503     11/2006
(Continued)

OTHER PUBLICATIONS

Santvliet et al., "Determinants of Eye Drop Size," *Survey of Ophthamology*, Mar.-Apr. 2004, vol. 49, pp. 197-211.
(Continued)

*Primary Examiner* — Steven M Cernoch
*Assistant Examiner* — Christopher R Dandridge
(74) *Attorney, Agent, or Firm* — Mintz Levin Cohn Ferris Glovsky and Popeo, P.C.

(57) ABSTRACT

An ejector device for ejecting droplets of fluid onto a surface includes an ejector mechanism attached to a fluid reservoir through a fluid loading plate that is configured to pierce the reservoir and channel the fluid to a rear surface of the ejector mechanism by capillary action. The ejector mechanism may have a centro-symmetric configuration with a lead free piezo actuator and may be covered by an auto-closing cover.

9 Claims, 41 Drawing Sheets

Related U.S. Application Data

(60) Provisional application No. 61/722,611, filed on Nov. 5, 2012, provisional application No. 61/722,616, filed on Nov. 5, 2012, provisional application No. 61/643,150, filed on May 4, 2012, provisional application No. 61/636,565, filed on Apr. 20, 2012, provisional application No. 61/636,559, filed on Apr. 20, 2012.

(51) Int. Cl.
*A61M 11/00* (2006.01)
*A61F 9/00* (2006.01)
*A61M 15/02* (2006.01)

(52) U.S. Cl.
CPC ........ *A61M 11/005* (2013.01); *A61M 15/025* (2014.02); *B05B 17/0661* (2013.01); *B05B 17/0676* (2013.01); *A61F 9/00* (2013.01); *A61M 2210/0612* (2013.01)

(58) Field of Classification Search
CPC ............ B05B 17/0638; B05B 17/0615; A61M 16/18; A61M 16/147; A61M 11/00; A61M 11/005; A61M 11/002; A61M 15/025
See application file for complete search history.

(56) References Cited

U.S. PATENT DOCUMENTS

| | | |
|---|---|---|
| 4,533,082 A | 8/1985 | Maehara et al. |
| 5,024,355 A | 6/1991 | Jouillat et al. |
| 5,152,456 A | 10/1992 | Ross et al. |
| 5,200,248 A | 4/1993 | Thompson et al. |
| 5,296,673 A | 3/1994 | Smith |
| 5,518,179 A | 5/1996 | Humberstone et al. |
| 5,607,410 A | 3/1997 | Branch |
| 5,630,793 A | 5/1997 | Rowe |
| 6,011,062 A | 1/2000 | Schneider et al. |
| 6,378,780 B1 * | 4/2002 | Martens, III ........ B05B 17/0646 239/102.2 |
| 6,530,370 B1 * | 3/2003 | Heinonen ............ A61M 11/005 128/200.14 |
| 6,550,472 B2 | 4/2003 | Litherland et al. |
| 6,921,020 B2 | 6/2005 | Ivri |
| 6,976,639 B2 | 12/2005 | Williams et al. |
| 7,448,559 B2 | 11/2008 | Le Maner et al. |
| 7,828,232 B2 | 11/2010 | Oomori et al. |
| 7,883,031 B2 | 2/2011 | Collins, Jr. et al. |
| 7,954,486 B2 | 6/2011 | Papania et al. |
| 8,012,136 B2 | 9/2011 | Collins, Jr. et al. |
| 8,371,290 B2 * | 2/2013 | Haveri ................. A61M 16/18 128/200.14 |
| 8,485,503 B2 * | 7/2013 | Lei ...................... B01F 3/04751 261/76 |
| 8,540,169 B2 * | 9/2013 | Kambayashi ............. A61L 9/14 239/102.2 |
| 8,545,463 B2 | 10/2013 | Collins, Jr. et al. |
| 8,684,980 B2 | 4/2014 | Hunter et al. |
| 2002/0085067 A1 | 7/2002 | Palifka et al. |
| 2002/0185125 A1 * | 12/2002 | Klimowicz .......... A61M 11/007 128/200.16 |
| 2003/0116642 A1 | 6/2003 | Williams et al. |
| 2004/0039355 A1 | 2/2004 | Gonzalez et al. |
| 2004/0215157 A1 | 10/2004 | Peclat et al. |
| 2004/0256487 A1 | 12/2004 | Collins, Jr. et al. |
| 2005/0211797 A1 | 9/2005 | Abergel et al. |
| 2006/0011737 A1 | 1/2006 | Amenos et al. |
| 2006/0243820 A1 | 11/2006 | Ng |
| 2007/0119969 A1 * | 5/2007 | Collins, Jr. .......... A61M 11/041 239/102.1 |
| 2007/0211212 A1 | 9/2007 | Bennwik |
| 2008/0043061 A1 | 2/2008 | Glezer et al. |
| 2008/0237530 A1 | 10/2008 | Tsukada et al. |
| 2008/0303850 A1 | 12/2008 | Shin et al. |
| 2009/0114742 A1 | 5/2009 | Collins, Jr. |
| 2009/0149829 A1 | 6/2009 | Collins, Jr. |
| 2009/0167812 A1 | 7/2009 | Asai et al. |
| 2009/0212133 A1 | 8/2009 | Collins, Jr. |
| 2009/0272818 A1 | 11/2009 | Valpey et al. |
| 2010/0211408 A1 | 8/2010 | Park et al. |
| 2010/0222752 A1 * | 9/2010 | Collins, Jr .......... B05B 17/0646 604/296 |
| 2010/0308132 A1 | 12/2010 | Marchetti et al. |
| 2011/0175971 A1 | 7/2011 | Newton et al. |
| 2011/0233302 A1 | 9/2011 | Lin et al. |
| 2011/0254901 A1 | 10/2011 | Sakai |
| 2011/0284656 A1 * | 11/2011 | Kambayashi ....... B05B 17/0646 239/102.2 |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0318260 A1 | 12/2012 | Hsieh et al. |
| 2013/0125878 A1 | 5/2013 | Hsieh et al. |
| 2013/0150812 A1 | 6/2013 | Hunter et al. |
| 2013/0172830 A1 | 7/2013 | Hunter et al. |
| 2013/0299607 A1 | 11/2013 | Wilkerson et al. |
| 2013/0334335 A1 | 12/2013 | Wilkerson et al. |
| 2014/0151457 A1 | 6/2014 | Wilkerson et al. |
| 2014/0336618 A1 | 11/2014 | Wilkerson et al. |
| 2014/0361095 A1 | 12/2014 | Haran |
| 2017/0136484 A1 | 5/2017 | Wilkerson et al. |

FOREIGN PATENT DOCUMENTS

| | | | | |
|---|---|---|---|---|
| CN | 101274850 | | 10/2008 | |
| CN | 101479046 | | 7/2009 | |
| CN | 101663097 A | | 3/2010 | |
| EP | 1219314 | | 7/2002 | |
| EP | 2253322 | | 11/2010 | |
| FR | 2797189 | * | 2/2001 | ............ A61L 9/122 |
| FR | 2934128 | | 1/2010 | |
| JP | S62-142110 | | 6/1987 | |
| JP | 5-49067 | | 6/1993 | |
| JP | 2008-515625 | | 5/2008 | |
| JP | 2012-508129 | | 4/2012 | |
| WO | WO 95/15822 | | 6/1995 | |
| WO | WO 2011/083379 | | 7/2011 | |
| WO | WO 2012/009696 | | 1/2012 | |
| WO | WO 2012/009706 | | 1/2012 | |
| WO | WO 2012/119702 | | 1/2012 | |
| WO | WO 2013/090468 | | 6/2013 | |

OTHER PUBLICATIONS

Brown et al., "The Preservation of Ophthalmic Preparations," *Journal of the Society of Cosmetic Chemists*, 1965, vol. 16, pp. 369-393.

* cited by examiner 0.3 mL Air △ P = 50.40 kPa 0.4 mL Air △ P = 50.33 kPa

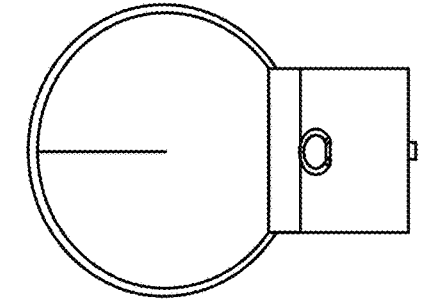
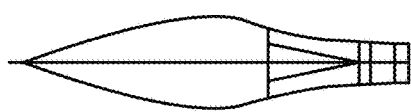
FIG. 32A
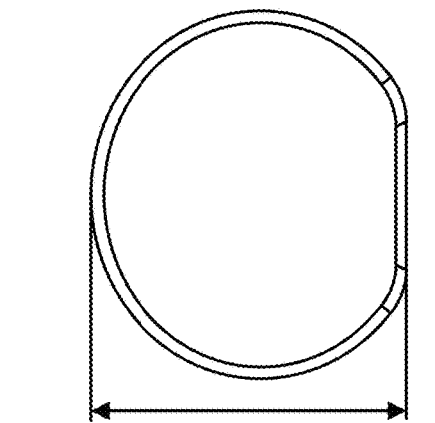
FIG. 32B
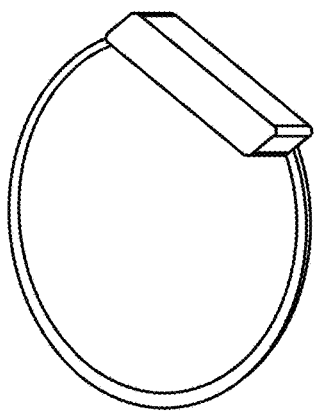
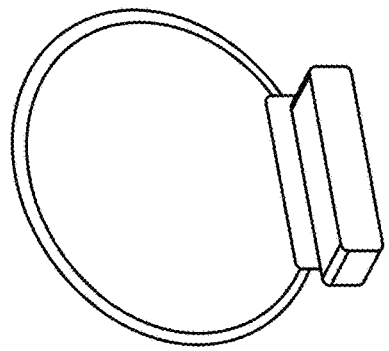

FIG. 43

SPRAY EJECTOR DEVICE AND METHODS OF USE

RELATED APPLICATIONS

This application is a continuation of U.S. patent application Ser. No. 13/866,783, entitled "SPRAY EJECTOR DEVICE AND METHODS OF USE," filed on Apr. 19, 2013, which claims the benefit of the filing date of US Provisional Application Nos.: 61/636,559 filed Apr. 20, 2012; 61/636,565 filed Apr. 20, 2012; 61/643,150 filed May 4, 2012; 61/722,611 filed Nov. 5, 2012, and 61/722,616 filed Nov. 5, 2012, the contents of which are herein incorporated by reference in their entireties.

FIELD OF THE DISCLOSURE

The present disclosure relates to ejector devices, and methods of manufacturing ejector devices. In particular, it relates to devices and methods for ejecting mists, or sprays of micro-droplets.

BACKGROUND OF THE INVENTION

Using spray devices to administer products in the form of mists or sprays is an area with large potential for safe, easy-to-use products. A major challenge in providing such a device is to provide consistent and accurate delivery of suitable doses and to avoid contamination of the product being delivered.

An important area where spray devices are needed is in delivery of eye medications. The application of fluids, as in the case of eye drops, has always posed a problem, especially for children and animals, which tend to blink or jerk at the critical moment of administration, causing the droplet to land on the eyelid, nose or other part of the face. The impact of a large drop or drops of fluid on the eyeball, especially when the fluid is at a different temperature, also tends to produce a blinking reaction. The elderly also often lose the hand coordination necessary to get the eye drops into their eyes. Stroke victims have similar difficulties. Currently, many of these medications are administered using eye droppers, which often require either the head to be tilted back, the subject to lie down or provide downward traction on the lower eyelid, or a combination of traction and tilting, since the delivery mechanism typically relies on gravity for applying the medication. This is not only awkward, but involves a fair amount of coordination, flexibility and cooperation on the part of the subject to ensure that the medication gets into the eye while avoiding poking the eye with the dropper tip. In current eye dropper bottles, the pointed applicator tip poses the risk of poking the user in the eye, potentially causing physical damage to the eye, and further, exposing the tip to bacterial contamination due to contact with the eye. As such, the subject runs the risk of contaminating the medication in the eye dropper bottle and subsequently infecting the eye. Additionally, a large volume of the medication flows out of the eye or is washed away by the tearing reflex. As a result, this method of administration is also inaccurate and wasteful. Moreover, the eye dropper does not provide a satisfactory way of controlling the amount of medication that is dispensed, nor does it provide a way of ensuring that the medication that is dispensed actually lands on the eye and remains on the eye.

Eye droppers also provide no way of verifying compliance by a subject. Even if after a week of use the eye dropper bottle could be checked for the total volume of medication dispensed, e.g., by weighing the bottle, this does not provide a record of day-to-day compliance. A subject may have missed one or more doses and overdosed on other occasions. Also, the poor precision with which eye droppers deliver drops to the eye makes it difficult to determine whether the medication is actually delivered into the eye, even though it may have been dispensed.

The ability of piezoelectric droplet generation systems to eject fluid has conventionally been largely limited by the piezoelectric material properties of the employed ceramic. For many years, an alternative piezoelectric material system that is lead free with comparable properties to lead based systems has been sought in order to meet worldwide regulations. This material system has yet to surface. An ejector system design which minimizes the dependency on piezoelectric material properties to allow comparable ejection with inferior material characteristics is thus highly desirable.

Accordingly, there is a need for a delivery device that delivers safe, suitable, and repeatable dosages to a subject for ophthalmic, topical, oral, nasal, or pulmonary use.

SUMMARY OF THE INVENTION

According to the present disclosure there is provided an ejector device comprising a housing, a reservoir having a volume of fluid contained within the housing, a fluid loading plate in fluid communication with the fluid in the reservoir and an ejector mechanism in fluid communication with the fluid loading plate, wherein the fluid loading plate provides fluid to a rear surface of the ejector mechanism, and the ejector mechanism is configured to eject a stream of droplets of fluid through at least one opening. The fluid loading plate may be configured to be placed in a parallel arrangement with the ejector mechanism so as to provide fluid to a rear ejection surface of the ejector mechanism. The ejector device of the disclosure is capable of delivering a defined volume of fluid in the form of droplets having properties that afford adequate and repeatable high percentage deposition upon application.

In this regard, an important consideration according to the present disclosure is not only to be able to deliver the medication in an easier to use manner, e.g. by spraying a mist horizontally onto the surface to be treated, but also to ensure that the medication is consistently provided to the ejector or delivery mechanism in any orientation. In some implementations, the ejector device is capable of ejecting a stream of droplets when the ejector device is tilted, even if tilted 180 degrees upside-down.

In certain embodiments, the fluid loading plate may comprise a capillary plate fluid delivery device for delivering fluid from a reservoir to an ejector mechanism of an ejector device, and methods of use for delivering safe, suitable, and repeatable dosages of fluids to a subject for ophthalmic, topical, oral, nasal, or pulmonary use. The capillary plate may comprise a fluid reservoir interface, an ejector mechanism interface, and one or more fluid channels for channeling fluid to the ejector mechanism by one or more mechanisms, including capillary action.

In other embodiments, the fluid loading plate may comprise a puncture plate fluid delivery system for delivering fluid from a reservoir to an ejector mechanism of an ejector device. The puncture plate fluid delivery system, also referred to as a capillary/puncture plate fluid delivery system, may include a capillary plate portion comprising a fluid retention area between the puncture/capillary plate fluid delivery system and a rear surface of an ejector mechanism for channeling fluid to the ejector mechanism by one or more mechanisms, including capillary action, and at least one hollow puncture needle for transferring fluid from a reservoir to the fluid retention area.

In certain aspects, the puncture plate fluid delivery system may include a first and a second mating portion, wherein a reservoir is attached in fluid communication to the second mating portion, the second mating portion including a puncturable seal. The first mating portion may form a receptacle for the second mating portion, and may include the least one hollow puncture needle for puncturing the puncturable seal. The first mating portion and the at least one puncture needle may be integrally formed. The puncturable seal included in the second mating portion may comprise a self-sealing silicone.

The reservoir, also referred to herein as an ampoule, may comprise a collapsible and flexible container. The reservoir may comprise a container and a lidding wherein the reservoir is configured so that the lidding and container form a volume capable of containing a fluid. The reservoir may be configured to be partially collapsed (at sea level) and capable of expanding to accommodate expansion of gas within the volume and prevent leaks.

The ejector mechanism may comprise an ejector plate coupled to a droplet generator plate (referred to herein simply as a generator plate) and a piezoelectric actuator; the generator plate including a plurality of openings formed through its thickness, and the piezoelectric actuator being operable to oscillate the ejector plate and thereby oscillate the generator plate at a frequency to generate a directed stream of droplets. The ejector plate may have a central open region aligned with the generator plate, wherein the piezoelectric actuator is coupled to a peripheral region of the ejector plate so as not to obstruct the plurality of openings of the generator plate. The plurality of openings of the generator plate may be disposed in a center region of the generator plate that is uncovered by the piezoelectric actuator and aligned with the central open region of the ejector plate. The three-dimensional geometry and shape of the openings, including orifice diameter and capillary length, and spatial array on the generator plate may be controlled to optimize generation of the directed stream of droplets. The generator plate may be formed from a high modulus polymer material, for example, formed from a material selected from the group consisting of: ultrahigh molecular weight polyethylene (UHMWPE), polyimide, polyether ether ketone (PEEK), polyvinylidene fluoride (PVDF), and polyetherimide. The ejector mechanism may be configured to eject a stream of droplets having an average ejected droplet diameter greater than 15 microns, with the stream of droplets having low entrained airflow such that the stream of droplets deposits on the eye of the subject during use.

The ejector mechanism may have a centro-symmetric structure in which the ejector plate includes symmetrically arranged mounting structures, with a symmetric configuration in which droplets are ejected from a central region of the symmetrical structure. The piezoelectric actuator may induce a resonance amplification of the generator plate coupled to the ejector plate to provide for a greater variety of piezoelectric constants. The ejector plate may be made of a high modulus polymeric material, and the piezoelectric actuator may be lead free, or substantially lead free.

The droplets may be formed in a distribution of sizes, each distribution having an average droplet size. The average droplet size may be in the range of about 15 microns to over 400 microns, e.g., greater than 20 microns to about 400 microns, about 20 microns to about 200 microns, about 100 microns to about 200 microns, about 20 microns to about 80 microns, about 25 microns to about 75 microns, about 30 microns to about 60 microns, about 35 microns to about 55 microns, etc. However, the average droplet size may be as large as 2500 microns, depending on the intended application. Further, the droplets may have an average initial velocity of about 0.5 m/s to about 100 m/s, e.g., about 0.5 m/s to about 20 m/s, about 0.5 to about 10 m/s, about 1 m/s to about 5 m/s, about 1 m/s to about 4 m/s, about 2 m/s, etc. As used herein, the ejecting size and the initial velocity are the size and initial velocity of the droplets when the droplets leave the ejector plate. The stream of droplets directed at a target will result in deposition of a percentage of the mass of the droplets including their composition onto the target.

The ejector mechanism and fluid loading plate may be assembled to form a unit defining an ejector assembly, the ejector assembly comprising a fluid loading plate in fluid communication with an ejector mechanism such that the fluid loading plate provides fluid to a rear surface of the ejector mechanism, the ejector mechanism being configured to eject a stream of droplets. In certain embodiments, the ejector assembly may further comprise a reservoir in fluid communication with the fluid loading plate.

The ejector device may further include an auto-closing system, which generally reduces crystallization, evaporation, and contamination risk. The auto-closing system may include a user-activated slide-plate that sealingly engages a gasket or seal formed to surround at least the holes in the generator plate, and which is slidable between an open position in which the holes are exposed and a close position in which the holes are covered by the slide-plate. The slide-plate may be biased toward its closed position by means of a spring. The slide plate may include an opening configured to coincide with the holes in the generator plate when the slide-plate is in its open position. Means may be included in the auto-closing system to ensure that the slide plate presses with sufficient pressure against the seal when in the closed position.

Further, according to the disclosure, there is provided an auto-closing system for a droplet ejection device which generally reduces crystallization, evaporation, and contamination risk.

Still further, according to the disclosure, there is provided a method for the fabrication of a generator plate for ejecting high viscosity fluids suitable for ophthalmic, topical, oral, nasal, or pulmonary use, comprising laser micromachining of materials to form three-dimensional openings through the thickness of the material, each of the openings defining an entrance cavity and a capillary channel, wherein the opening comprises an overall pitch length.

Still further, according to the disclosure there is provided a method of delivering a volume of ophthalmic fluid to an eye of a subject, the method comprising ejecting a directed stream of droplets of an ophthalmic fluid contained in a reservoir from openings of an ejector plate, the droplets in the directed stream having an average ejecting diameter in the range of 5-2500 microns, e.g., 20-400 microns, e.g., 20-200 microns, and including but not limited to a range of 100-200, etc., and an average initial velocity in the range of 0.5-100 m/s, e.g., 1-100 m/s, e.g., 2-20 m/s.

These and other aspects of the invention will become apparent to one of skill in the art.

BRIEF DESCRIPTION OF THE DRAWINGS

FIG. 1 is a three-dimensional exploded view of the mechanical parts of one embodiment of an ejector device of the disclosure;

FIG. 5 illustrates the variation of atmospheric pressure (p) with altitude (h);

FIGS. 6A-6D illustrate various embodiments of components of a reservoir according to one embodiment of the disclosure;

FIG. 7 illustrates a form, fill and seal process for generation of reservoirs in accordance with one embodiment of the disclosure;

FIG. 8 shows an embodiment of a reservoir, fluid loading plate and ejector plate in accordance with an aspect of the disclosure, illustrating the direction of droplet ejection relative to attitude angle.

FIG. 11 illustrates the effect of the volume $V_{gas}$ expressed as a percentage of $V_t$ on the differential leakage pressure value for different embodiments of a reservoir, fluid loading plate and ejector assembly in accordance with aspects of the disclosure.

FIG. 12 illustrates the loss of mass from reservoirs (ampoules) over time, in accordance with an aspect of the disclosure;

FIGS. 13A-13B illustrate the attitude insensitivity of an embodiment of the disclosure having a collapsible and flexible reservoir (ampoule) in FIG. 13B, compared to an embodiment of the disclosure having a hard reservoir in FIG. 13A;

FIGS. 15A-15C show one embodiment of an ejector mechanism in relation to an embodiment of a capillary plate of the disclosure;

FIG. 19 illustrates that an increased water height behind an ejector plate in the presence of a capillary plate leads to an increased mass loading effect at a particular frequency;

FIG. 20 illustrates the downward shift in frequency associated with a capillary plate used with the delivery of various fluids;

FIG. 21 illustrates the reduction in mass loading for fluids of increasing density and viscosity;

FIG. 22 illustrates the attitude insensitivity of an ejector device that includes a capillary plate;

FIG. 27 is a schematic representation of a puncture plate system of the disclosure showing the Venturi effect;

FIG. 28 illustrates the principles of Bernoulli's equation;

FIG. 29 illustrates the principles of hydrostatic pressure;

FIG. 30 shows schematic representations of different reservoir configurations of the disclosure;

FIGS. 32A-32B show three dimensional pictures and side view and front view drawings of two collapsible reservoir embodiments of the disclosure;

FIG. 41 shows the pull down performance for select round LTS ampoule designs from FIG. 35.

FIG. 42 shows the mechanism involved in inverted spray using a round LTS reservoir;

FIG. 43 shows the actual spray down performance results of an LTS reservoir embodiment sprayed down in a complete puncture system upside down of the disclosure;

FIG. 44 shows the spray down performance of another puncture plate configuration with an embodiment of an embodiment an IV bag reservoir of the disclosure;

FIG. 45 shows the spray down performance of two different puncture plate configurations with an embodiment of an IV bag reservoir of the disclosure in different orientations and with different spray directions;

FIG. 46 shows the spray down performance of one embodiment of a puncture plate configuration with an embodiment of an IV bag reservoir of the disclosure in different orientations and with different spray directions and different puncture plate vent opening options;

FIG. 47 shows schematically the relationship between capillary effect and hydrostatic pressure of the reservoir;

FIG. 48 shows capillary pressure for various sized half droplets of water;

FIG. 49 shows capillary pressure for various sized half droplets of latanaprost;

FIG. 50 shows capillary rise for various fluid types having different contact angle values;

FIG. 55A shows a cross-sectional view of one embodiment of an ejector assembly of the disclosure;

FIG. 55B shows a three dimensional view of one embodiment of an ejector mechanism of the disclosure;

FIG. 55C shows a front view of one embodiment of a centro-symmetric ejector mechanism of the disclosure;

FIG. 55D shows a dismantled view of one embodiment of an ejector mechanism of the disclosure;

FIG. 56 shows the nomenclature of the axis numbering convention for piezoelectric effects;

FIG. 57 shows modes of operation of an active region of one embodiment of generator plate, and digital holographic microscopy images of oscillation of the generator plate;

FIG. 58 illustrates a comparison of mass ejection for PZT and $BaTiO_3$ (lead free) piezoelectric actuator materials using an ejector assembly with an inside mounted piezoelectric actuator according to one embodiment of the disclosure;

FIGS. 69A-69C show transmission light microscopy images over time of a mesh screen of a generator plate in which the system was not provided with a capillary plate, and FIGS. 70A-70C show transmission light microscopy images over time of a mesh screen of a generator plate in which the system was provided with a capillary plate.

DETAILED DESCRIPTION

The present application relates to ejector devices for delivering fluid to a surface as an ejected stream of droplets. The ejector device may for example be as described in U.S. Provisional Application Nos. 61/569,739, 61/636,559, 61/636,565, 61/636,568, 61/642,838, 61/642,867, 61/643,150 and 61/584,060, and in U.S. patent application Ser. Nos. 13/184,446, 13/184,468 and 13/184,484, the contents of which are incorporated herein by reference.

The ejector device of the present disclosure may, for example, be useful, in the delivery of fluid for ophthalmic, topical, oral, nasal, or pulmonary use. However, the disclosure is not so limited, and may be useful with any ejector devices (e.g., printer devices, etc.).

In certain embodiments, the ejector device may comprise a housing, a reservoir disposed within the housing for receiving a volume of fluid, a fluid loading plate, and an, ejector mechanism configured to eject one or more streams of droplets of a fluid, wherein the reservoir is in fluid communication with the fluid loading plate, which is in fluid communication with the ejector mechanism such that the fluid loading plate provides fluid to a rear surface of the ejector plate.

Thus the present disclosure generally relates to an ejector device for ejecting a fluid onto a surface e.g., the ejection of ophthalmic fluid onto the eye of a patient. One embodiment components of the ejector device will be described broadly with respect to FIG. 1, whereafter some of the elements making up the device will be discussed in greater detail. It will however be appreciated that the application is not limited to the particular embodiments described herein but includes variations and different combinations of the elements making up the ejector device.

For purposes of this application, fluid includes, without limitation, suspensions or emulsions which have viscosities in a range capable of droplet formation using an ejector mechanism.

Figure 1:
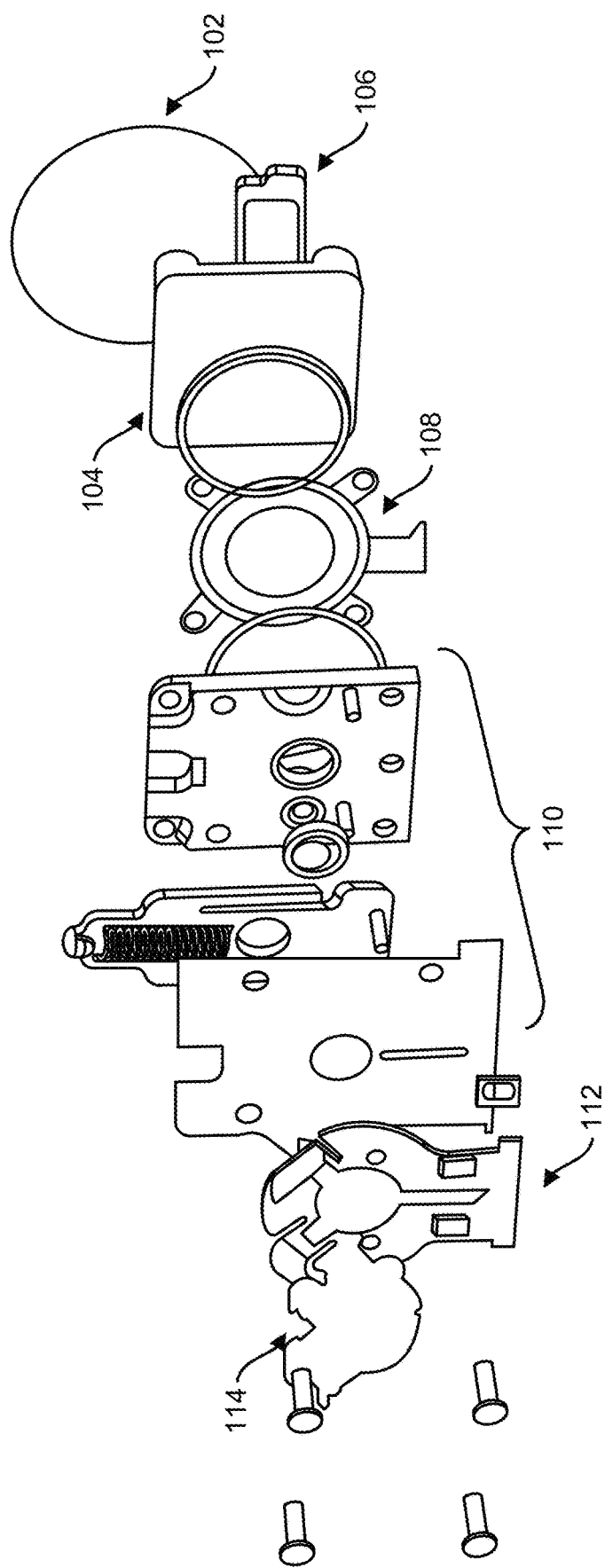

FIG. 1 shows an exploded view of one embodiment of internal components of an ejector device 100 of the present disclosure, and includes a reservoir 102, which in this embodiment is a flexible reservoir made using a self-sealing RF weld technique. The reservoir 102 is placed into fluid communication with a fluid loading plate 104 by means of puncturable seal mating 106. The fluid loading plate supplies the fluid from the reservoir to the rear face of an ejector mechanism 108 by, e.g., capillary action. The ejector in this embodiment comprises a piezo ejector mechanism configured to generate a controllable stream of droplets of fluid. While the present embodiment describes a fluid loading plate 104, which is also discussed in greater detail below, other configurations may be adopted for channeling fluid by capillary action from the reservoir to the ejector mechanism. In order to limit evaporation, crystallization and contamination of the fluid, an auto-closing system 110 is mounted in front of the ejector mechanism 108. A bracket 112 for supporting a housing 114 for a targeting LED is configured to clip onto the front face of the auto-closing system 110.

Figure 2:
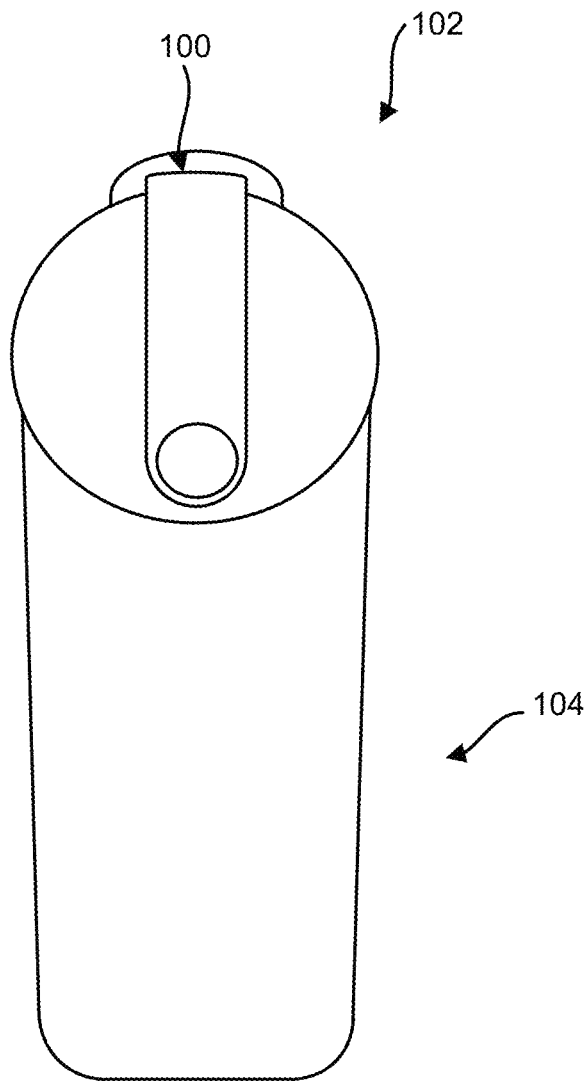
FIG. 2 is front view of one embodiment of a an ejector device of the disclosure.

As shown in FIG. 2, in certain embodiments, the mechanical components of the ejector device may be mounted inside a removable top section 200 of a housing 202, which mates with lower hand-grip portion 204. The electronics for controlling the ejection of fluid and power source may be housed inside the lower hand-grip portion 204 of the housing 202.

Figure 3:
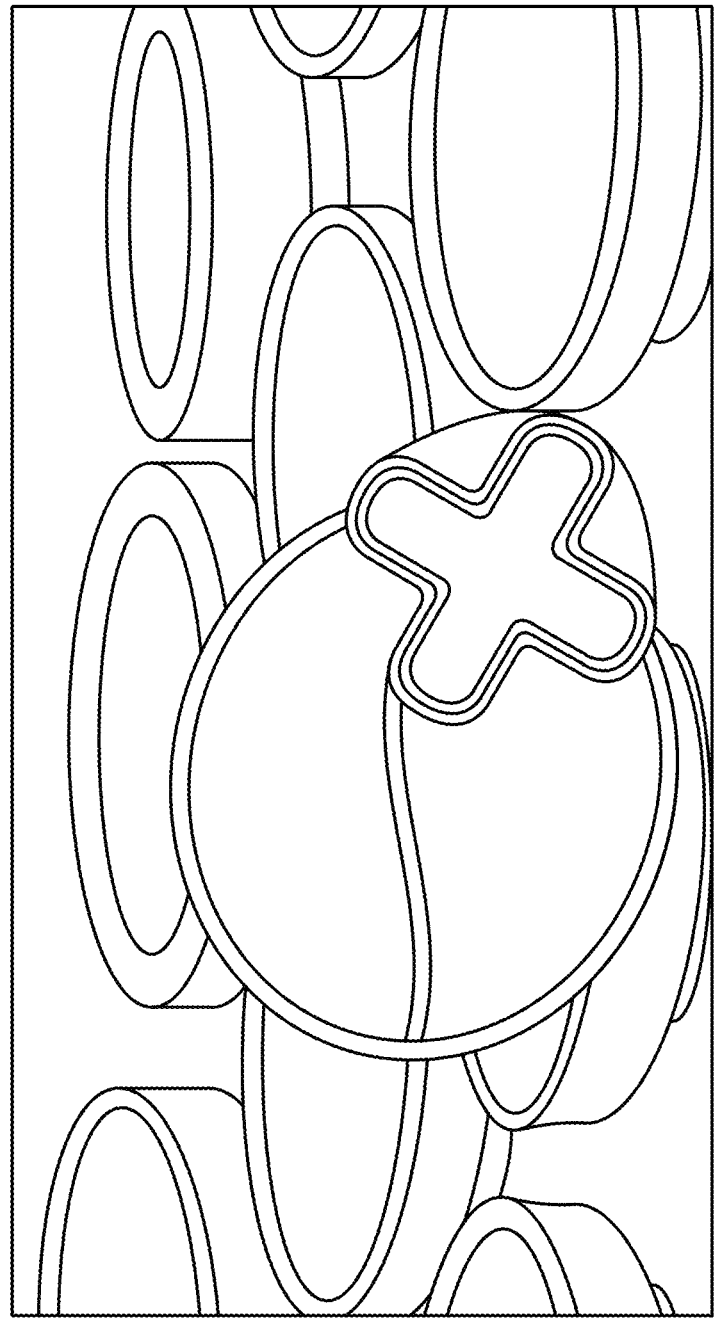
FIG. 3 shows one embodiment of a reservoir of the disclosure.
Figure 4:
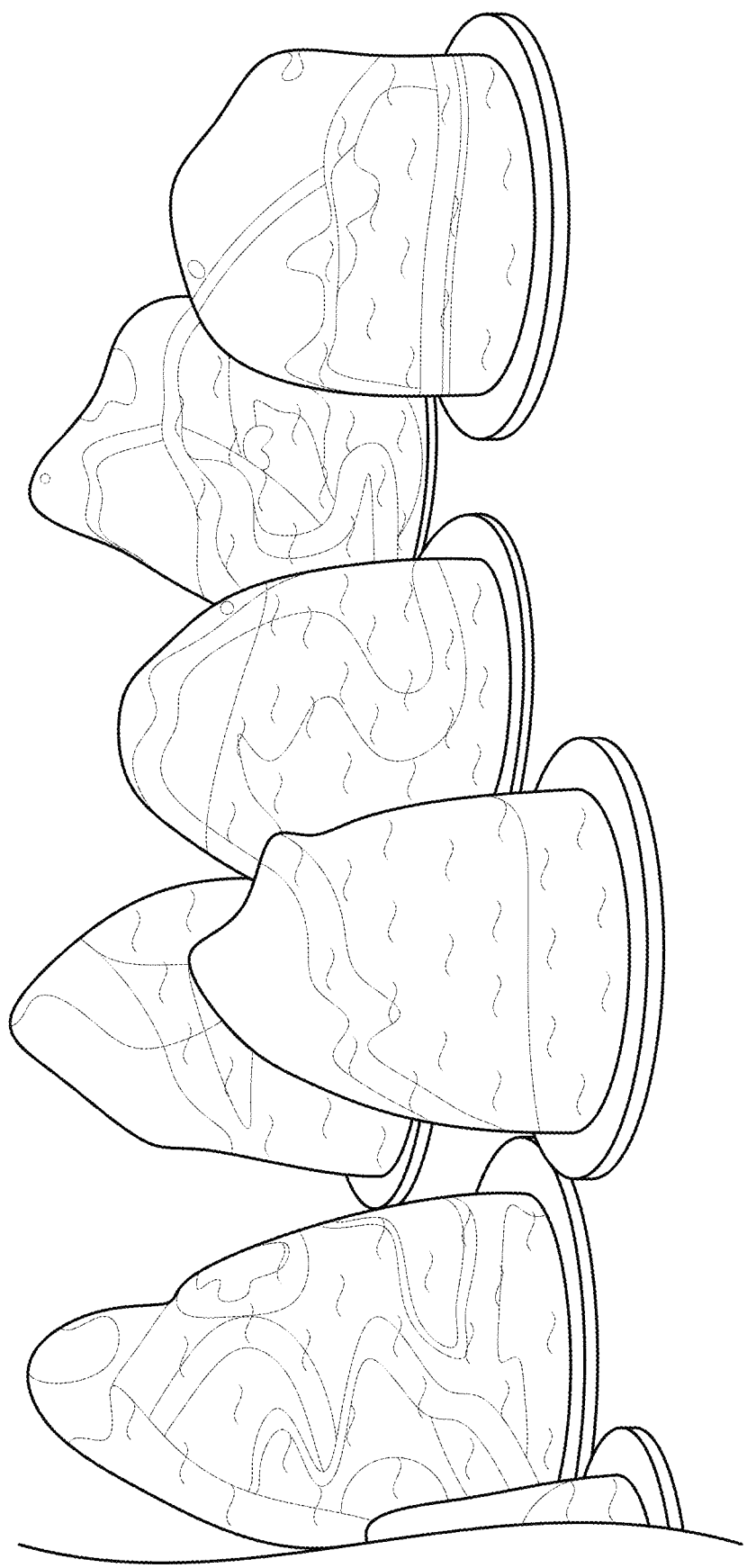
FIG. 4 shows another embodiment of a reservoir of the disclosure.

The reservoir or ampoule 102 for use with the ejector device 100 may comprise a flexible, or a hard, non-flexible reservoir. In certain embodiments, the reservoir comprises a collapsible and flexible reservoir 102 disposed within the top section 200 of the housing 202, and contains or is adapted to receive a volume of fluid. Different types of flexible reservoirs made using different techniques are contemplated by the present disclosure, including self-sealing, radio frequency (RF) weld reservoirs as shown in FIG. 1. Alternatively, a blow-fill-seal technique can be used to form a similar configuration reservoir as shown in FIG. 3, or a form-fill-seal technique can be used to provide a reservoir such as that shown in FIG. 4. As will become clearer from the discussion below, the particular configuration of the reservoir may vary from one embodiment to the next. For example, the shape of the form-fill-seal reservoirs is not limited to that shown in FIG. 4.

With reference to FIG. 5, atmospheric pressure varies with altitude. Specifically, as the altitude increases, the pressure decreases. In accordance with Boyle's Law, the volume of a gas increases as the pressure decreases. Similarly, Charles' Law provides that as the temperature increases, so does the volume of a gas. In contrast, liquids generally have small changes in volume in response to changes in pressure and temperature, water being a notable exception which expands when cooled from 4° C. to 0° C. Thus while a liquid in a reservoir will change little when the pressure and temperature conditions change, a reservoir having a volume of liquid and also a volume of gas must be designed to accommodate decreases in pressure and increases in temperature. In many cases, the greater concern arises from changes in pressure, causing significant volume changes in the gas. Changes in altitude are a common cause of changes in pressure and therefore in the volume of gases.

Without intending to be limited by theory, a change in atmospheric pressure due to changes in altitude can be determined according to the following equation:

$$p = p_0 \cdot \left(1 - \frac{L \cdot h}{T_0}\right)^{\frac{g \cdot M}{R \cdot L}},$$

Where:

| Parameter | Description | Value |
| --- | --- | --- |
| $p_0$ | sea level standard atmospheric pressure | 101325 Pascal (Pa) |
| L | Temperature lapse rate | 0.0065° Kelvin (K)/meter (m) |
| $T_0$ | sea level standard temperature | 288.15° K |
| g | Earth-surface gravitational acceleration | 9.80665 m/sec (s) |
| M | molar mass of dry air | 0.0289644 kg/mol |
| R | Universal gas constant | 8.31447 Joule (J)/(mol ° K) |

An ampoule or reservoir, or a device containing the ampoule or reservoir may, according to the disclosure, be transported in an airplane or to a geographic location high above sea level. As discussed, such changes can lead to pressure differentials from sea level that can lead to leakage from orifices of an ejector device. For example, cabins in an airplane can be pressurized for altitudes from 6000 ft. to 8000 ft. The corresponding pressure differential from sea level is 20 to 29 kPa, respectively Ampoules that are not capable of accommodating for this pressure differential by expanding often lead to pressure buildup within the ampoule and subsequent fluid leakage from the device. As used herein, "ambient pressure" refers to the air pressure to which the reservoir, ampoule or the device having a reservoir or ampoule is exposed to. As used herein, "pressure differential" refers to the air pressure difference between the ambient pressure and the standard air pressure at sea level (101325 Pascal (Pa)). Thus, the reduced pressure as found in a plane is the ambient pressure and the pressure differential is the difference between the ambient pressure and the standard pressure at sea level (e.g., about 20 kPa at 6000 ft). Similarly, the pressure differential at an altitude above sea level is the difference between the standard pressure at sea level (101325 Pascal (Pa)) and the ambient pressure at that altitude.

In other embodiments, the reservoir or ampoule may be a hard reservoir designed to accommodate expansion of any gas therein. In some embodiments, the expansion may be suppressed by providing a pressurized enclosure. In other embodiments, leakage may be suppressed by sealing any orifice present on the reservoir.

With reference to FIGS. 6A to 6D, in certain embodiments, the reservoir (in this case a form-fill-seal reservoir) may comprise an ampoule having three components, a lidding 601, a container 602, and optionally a stiffening ring 603. In some embodiments, the lidding 601 is sealed to the container 602 to form an enclosed impermeable container. In an embodiment, the sealed impermeable combination of lidding 601 and container 602 provides for storage of the liquid. In other embodiments, the container 602 forms a flexible reservoir that can accommodate the expansion of a gas contained with and trapped by the reservoir. In other embodiments, the reservoir may be formed of non-pliable materials to make a stiff reservoir.

In some aspects according to the present disclosure, the ampoule or reservoir may be assembled from multiple components so that the properties of lidding 601, container 602, and stiffening ring 603 may be adapted according to the needs of the device's application. In other embodiments, the container 602 and stiffening ring 603 may be formed together, and lidding 601 applied following addition of a desired fluid. In an embodiment, the sealed impermeable combination of lidding 601 and container 602 may be formed separately. In certain embodiments, the lidding 601 may be puncturable.

In certain embodiments, the shape and size of the ampoule or reservoir may be selected according to the needs of the intended use. In a non-limiting example, a fluid for ophthalmic use may be required by a person in need for a short treatment time, and thus may require fewer doses. Where few doses are indicated, the shape and size of the ampoule may be scaled appropriately to avoid unnecessary waste. In other aspects, large volumes may be indicated where the fluid is required over a long period of time, or may require multiple daily doses.

The volume 610 may be controlled by varying the depth 607, the diameter 604, and the shape 609. In some aspects, for example for pulmonary use, the diameter 604 may be more than 1 cm in diameter. In another aspect, the diameter may be 1.5 cm. In a further embodiment, the diameter may be from 1 to 3 cm. In another embodiment the diameter may be between 1 and 4 cm, or 1 and 5 cm. In other embodiments, the diameter 604 may be 3 cm or more, 4 cm or more, 5 cm or more, 6 cm or more, or 7 cm or more. In other embodiments, the diameter may be configured for a device, for example, for ophthalmic applications. For example, the diameter 604 may be 20 mm or less. In other embodiments, the diameter 604 may be 19 mm or less. In another embodiment, the diameter 604 may be 18 mm or less. In yet another embodiment, the diameter 604 may be 17 mm or less. In an embodiment, the diameter 604 may be 16 mm or less. In other embodiments of the present disclosure, the diameter 604 may be from 18 to 19 mm. In another embodiment, the diameter may be from 15 to 20 mm, 16 to 20 mm, 17 to 20 mm, 18 to 20 mm, or 19 to 20 mm. In other embodiments, the diameter 604 may be from 15 to 19 mm, 16 to 19 mm, 17 to 19 mm, or 18 to 19 mm.

In certain embodiments according the present disclosure, the shape 609 of the ampoule may be modified to increase or decrease the volume in view of the diameter 604. In some embodiments, the shape 609 may be configured so that the diameter decreases toward the closed end of the container along the depth 607. In certain aspects, the decreasing diameter may provide for removal of a mold. Design and manufacture of molds to form ampoules according to the present invention having a container 602 are known in the art.

In certain embodiments of the present disclosure, the ampoule may comprise a stiffening ring 603 configured to add stability to the container 602. In some embodiments, the container 602 may be flexible and a stiffening ring 603 may provide for connection to the devices or housings according to the present disclosure. The thickness 606 and the diameter 605 may be determined based on the diameter 604 of the shaped container 602. In an aspect, the thickness 606 may be determined according to the material of stiffening ring 603.

The sealed combination of lidding 601 and container 602, and optional stiffening ring form an ampoule suitable for holding and storing a fluid for ophthalmic, topical, oral, nasal, or pulmonary use until insertion of the ampoule into an ejector device or ejector device housing. In some embodiments, the sealed ampoule may be suitable for short-term storage of a fluid for ophthalmic, topical, oral, nasal, or pulmonary use. In other embodiments, the sealed ampoule may be suitable for long term storage of a fluid for ophthalmic, topical, oral, nasal, or pulmonary use.

In certain implementations, the sealed fluid containing ampoule may be stored without loss or degradation of the fluid for 1 week. In other embodiments, the sealed ampoule may be stored for more than 1 week. In some embodiments, the sealed ampoule may suitable for short term storage including 2 weeks, 3 weeks, or one month. In certain implementation, the sealed ampoule may be stored for a month.

In certain implementations, the sealed fluid containing ampoule may be stored for longer periods without significant loss or degradation. In other embodiments, the sealed fluid containing ampoule may be stored for more than one month. In other embodiments, the sealed ampoule may be stored for more than two months. In some embodiments, the sealed ampoule may be suitable for long-term storage including three months, four months, or more. In certain implementations, the sealed ampoule may be stored for 5 months. In other embodiments, the sealed ampoule may be stored for 6 months. In some embodiments, the sealed ampoule may suitable for long-term storage including 7 months, 8 months, or more. In certain implementations, the sealed ampoule may be stored for 9 months. In certain implementations, the sealed ampoule may be stored for 10 months. In other embodiments, the sealed ampoule may be stored for 11 months. In some embodiments, the sealed ampoule may be suitable for long-term storage including 12 months, or more. In certain implementations, the sealed ampoule may be stored for 1.5 years. In yet other implementations, the sealed fluid filled ampoule may be stored for more than 1.5 years.

The lidding 601, container 602, and stiffening ring 603 may be formed from any suitable materials for use in the intended application. By way of example, in ophthalmic applications, any suitable material for use in pharmaceutical ophthalmic applications may be used, such as polymer materials that do not chemically react with or adsorb fluids to be delivered. In other aspects, the surfaces of the lidding 601, container 602, and stiffening ring 603 that are exposed to the fluid to be delivered may be formed from materials that provide desired surface properties, including for example hydrophobicity, hydrophilicity, non-reactivity, stability, etc. Examples of materials suitable for the lidding 601 and container 602 include materials presented in, but not limited by, Table 1.

TABLE 1

Example lidding and container materials

| Manufacturer | Product Name | Description |
| --- | --- | --- |
| Sealed Air | Nexcel Latitude ML29xxC | PE based coextruded film |
| Sealed Air | Nexcel M2930 | |
| Sealed Air | Nexcel MF513 clear | Barrier Medical film with oxygen barrier |
| Rollprint | Triad "C" | Extrusion laminated composite of polyester, polyethylene, aluminum foil and modified polyolefin sealant |
| Alcan Packaging Pharmaceutical Packaging Inc. | Pouch laminate Product Code 92036 | High barrier coextruded composite of PET, adhesive, aluminum, polyethylene |
| Texas Technologies | SV-300X | 3 mil nylon, EVOH, poly coex |
| SAFC Biosciences | Bioeaze | ethyl vinyl acetate film |
| Winpak | DF15YG2 | Peelable Al-foil based (Al/PE) |
| Winpak | WCS100 | Flexible packaging laminate composed of PET, LDPE Al, and coex |

In some embodiments according to the present disclosure, the material for container 602 may be selected for properties consistent with an FDA-approved medical device. Materials may be selected by methods and criteria known in the art, for example, ISO 10993-5, Biological Evaluation of Medical Devices—Part 5 US Pharmacopeia 32, Biological Reactivity Tests, In Vitro; ISO 13485, Medical Device Quality Management System; and ISO 17025, General Requirements for the Competence of Testing and Calibration Labs. For example, the container 602 may be a non-cytotoxic film such as ML29xxC available from Sealed Air.

According the present disclosure, material for container 602 may be a polymer. In certain embodiments the polymer may be a layered polymer. In other embodiments, the polymer may be a coextruded forming film. In certain embodiments, the polymer may be a polymer for use in medical devices. In one example according to the present disclosure, the film may be a polyethylene-based coextruded forming film. In certain embodiments, the polymer may be sterilized. In an aspect, the film may be selected according to its ability to bond to other films. In one example, the other film may be Tyvek or other coated medical material. In an aspect, the film may be either clear or opaque. In another aspect, the film may be resistant to punctures. In yet another aspect, the film may be resistant to down-gauging.

In an aspect, the film may formable. Formable films according to the present disclosure may be selected according to the requirements of the application. In certain aspects, the film may be selected based on one or more of the following criteria: thickness, Young's modulus, elongation, tensile strength, puncture force, tear and haze. In certain aspects, the flexibility of the film may provide for a collapsible ampoule. In an aspect, the collapsible ampoule may provide for the elimination of leakage upon changes of atmospheric pressure.

Examples of films compatible with devices and methods of the present invention include films provided in Table 2. According to the present disclosure, similar films may be selected based on the desired properties of Thickness, Young's modulus (MD), Elongation (MD), Tensile Strength (MD), Puncture, Tear, and Haze.

TABLE 2

Example films of the present disclosure
Sealed Air Nexcel ® Medical films: Latitude ML29xxC

|  | Unit | ASTM | 30 C. | 45 C. | 60 C. | 70 C. | 80 C. | 10 C. |
|---|---|---|---|---|---|---|---|---|
| Thickness* | micron |  | 75 | 112.5 | 150 | 175 | 200 | 250 |
| Young's modulus (MD) | kg/cm$^2$ | D882 | 4967 | 5059 | 4995 | 5002 | 5016 | 5023 |
| Elongation (MD) | % | D882 | 280 | 340 | 350 | 345 | 374 | 406 |
| Tensile Strength (MD) | kg/cm$^2$ | D882 | 375 | 332 | 329 | 335 | 315 | 296 |
| Puncture | N | F1306 | 13.26 | 19.39 | 24.24 | 28.02 | 31.70 | 38.99 |
| Tear | g | D1004 | 718 | 1020 | 1360 | 1610 | 1817 | 2262 |
| Haze | % | D1003 | 12 | 16 | 22 | 31 | 33 | 43 |

According to some implementations, lidding 601, container 602, and stiffening ring 603 may be a formed of materials suitable for sterilization. In some aspects lidding 601, container 602, and stiffening ring 603 may be sterilized together as a unit. In other aspects, lidding 601, container 602, and stiffening ring 603 may be sterilized separately, using one or more of the various methods of sterilization known in the art. In certain aspects of the present disclosure, one or more sterilization methods may be combined, for example chemical and irradiation methods as provided below.

In an aspect, lidding 601, container 602, and stiffening ring 603 may be formed from materials that are compatible with sterilization by irradiation. In an aspect, the material may be compatible with sterilization by gamma irradiation. In other aspect, the material may be chosen to be compatible with radiation such as electron beams, X-rays, or subatomic particles.

In another aspect, the container may be formed from materials that are compatible with chemical methods of sterilization. In an embodiment, the material may be compatible with ethylene oxide (EtO) sterilization. In another embodiment, the material may be compatible with ozone (O$_3$) sterilization. In another embodiment, the material may be compatible with Ortho-phthalaldehyde (OPA). In a further embodiment, hydrogen peroxide may be used as a chemical sterilizing agent.

In some aspects according the present disclosure, lidding 601, container 602, and stiffening ring 603 may be formed from materials that are compatible with heat sterilization. In an embodiment, the heat sterilization compatible material may be resistant to dry heat sterilization. In another embodiment, the heat sterilization compatible material may be compatible to moist heat sterilization. In some aspects according the present disclosure, lidding 601, container 602, and stiffening ring 603 may be formed from materials that are compatible with Tyndalization.

In some aspects, the materials chosen for lidding 601, container 602, and stiffening ring 603 provide for long term storage of the liquid. In some embodiments, the sealed ampoule may comprise impermeable materials. In certain aspects, the impermeability may be selected on the basis of the fluid. In one non-limiting example according to the present disclosure, the fluids for ophthalmic, topical, oral, nasal, or pulmonary use may require protection from light or air to maintain stability. In another non-limiting example according to the present disclosure, the fluids for ophthalmic, topical, oral, nasal, or pulmonary use may require protection from light and oxygen to maintain stability. In some embodiments, the materials may be impermeable to gases. In an embodiment, the gas may be oxygen. In other embodiments, the material may be impermeable to light. In another embodiment, the material may be impermeable to gas, for example oxygen, and impermeable to light.

In an aspect according to the present disclosure, the container 602 and lidding 601 material may be selected to be stable for extended periods. As one aspect, in certain embodiments, one or more properties including, but not limited to, the tensile strength, the percent elongation, tear resistance and impact stability may be used to determine the stability of the material.

Referring to FIG. 7, containers containing a fluid of the present invention may be prepared using a form, fill and seal process as known in the art. In certain embodiments, the entire process outlined in FIG. 7 may be performed under sterile conditions in compliance with applicable regulatory standards for medical devices and preparations. In one embodiment, a film may be applied to a mold and then heated and vacuum formed to create a container of shape 609 and depth 607. By varying the shape 609, depth 607 and diameter 604, a container or ampoule of a defined total volume ($V_t$) may be formed.

Once formed, the container (e.g., container 602 for example), may be filled with a fluid and a lidding applied to the filled container or ampoules. In some embodiments and by way of example only, a seal is applied to create a leak-proof closure. Other methods to attach and seal a lidding to the container are known in the art. Following sealing individual ampoules may be cut from the form. In other embodiments, the sealing and cutting can occur simultaneously. The final sealed containers or ampoules are then suitable for storage, shipping or use in an ejector devise. As mentioned above, the form-fill-seal process discussed in this embodiment is only one technique for forming and sealing containers are known in the art. Other techniques such as blow-fill-seal and self-sealing RF weld can also be used and do not make use of a lidding element.

In some embodiments of the current disclosure, the fluid ($V_f$) may fill the entire volume of container 602 (e.g., $V_t$). In other embodiments, the fluid may not completely fill the volume, leaving a space ($V_{AT}$). In embodiments where the liquid volume $V_f$ equals $V_{AT}$, applying a lidding may result in the entrapment of a volume of gas $V_{gas}$. In other embodiments, the volume of container 602 may be decreased by crushing or deforming up to a volume to reduce the volume by a volume ($V_r$). According the present disclosure, the volume of the sealed container or ampoule will be:

$$V_t = V_f + V_{gas} + V_r \text{ where}$$

$$V_{\Delta T} = V_{gas} + V_r$$

According to certain aspects of the present disclosure, the volume $V_r$ provides a capability to the container to expand to volume Vt, and thereby reduce the tendency of the container to leak when employed in an ejector device. Similar, the volume $V_r$ can accommodate an expansion of a volume of an aqueous fluid when shipped or stored frozen or under conditions where the volume of liquid may expand. In other embodiments, $V_{\Delta T}$ may include both a volume of gas $V_{gas}$ and a volume $V_r$ whereby, the change in gas volume associated with changes in ambient pressure may be compensated and provide for the preparation of leak free ejector devices. Similarly, the volume $V_r$ also provides for an expansion of gas of volume $V_{exp}$ that may occur during shipping or storage under conditions of lower ambient pressure.

In certain aspects according the present disclosure, the container may contain a volume of gas $V_{gas}$. In an aspect, the gas may be air. In an aspect, the gas may be air that has been depleted of oxygen. In other aspects the gas may be a non-reactive gas. In an aspect, the gas may be nitrogen. In another aspect, the gas may be a noble gas such as helium or argon. In other aspects, the gas may be $CO_2$. Any gas may be accommodated according to the present disclosure.

In certain embodiments of the disclosure, the reservoirs provide for attitude insensitivity of ejector devices. In an aspect the reservoir includes a flexible container. Specifically, as provided by certain aspects of the present disclosure, the reservoir provides a consistent amount of fluid to the ejector mechanism, regardless of the fluid level and device orientation. In some aspects, an ampoule or reservoir in fluid communication with an ejector mechanism provides a consistent flow of fluid to the rear surface of the ejector mechanism so that a consistent volume of fluid is ejected as droplets. In another aspect, the reservoir or ampoule is in fluid communication with a capillary plate that provides for consistent supply and delivery of fluid in a capillary fluid loading area at a rear ejection surface of an ejector mechanism. The ampoule provides for attitude insensitivity of the ejector device and a resistance to leakage as the ambient pressure is decreased relative to the standard pressure at sea level. Thus the combination of ampoule, capillary plate and ejector mechanism provide both reduced attitude and altitude sensitivity to the device so that a consistent volume of droplets is delivered.

Referring to FIG. 8, a device of the present disclosure ejects fluid in a direction 804, perpendicular to the direction of gravity 805. In an aspect of the present disclosure, the combination of ampoule 803 and fluid loading plate 802 provide for a consistent flow of fluid to the ejector plate 801 as the attitude angle theta (θ) is change. For example, as the attitude is increased, the combination provides for continued consistent flow of fluid. Accordingly, according to aspects of the present invention, the device continues to dispense droplets in the direction 804. In an aspect of the present disclosure, the attitude angle theta (θ) may be arbitrarily increased or decreased while maintaining a consistent flow of fluid to the ejector plate 801. For instance, the attitude angle theta (θ) may be more or less than 45°. Thus, the attitude angle theta (θ) may be between 0 and 45° or may be between 45° and 90°. The attitude angle theta (θ) may also be 90°. The attitude angle theta (θ) may also be 180° or may be between 0 and 180°.

In certain implementations according to the present invention, the containers are flexible containers having a total volume $V_t$ and contain a volume of liquid $V_f$ and a volume of gas $V_{gas}$, and have a expandable volume $V_r$. In certain aspects, the expandable volume $V_r$ provides for and accommodates the expansion of the gas $\Delta V_{gas}$ due to changes in pressure while not resulting in an increase in pressure within the container. Thus, while in transit for example, an expansion of $\Delta V_{gas}$ does not cause the container to leak. Similarly, the expansion of an aqueous fluid upon freezing can be similarly accommodated.

Many implementations of the invention have been disclosed. This disclosure contemplates combining any of the features of one implementation with the features of one or more of the other implementations. For example, any of the ejector mechanisms or capillary plates can be used in combination with the container, as well as any of the housings or housing features, e.g., covers, supports, rests, lights, seals and gaskets, fill mechanisms, or alignment mechanisms. Further variations in any of the elements of any of the embodiments within the scope of ordinary skill are contemplated by this disclosure. Such variations include selection of materials, coatings, or methods of manufacturing. Other methods of fabrication known in the art and not explicitly listed herein can be used to fabricate, test, repair, or maintain the device.

Example 1: Measurement of Differential Pressure Leak Values

Figure 9B:
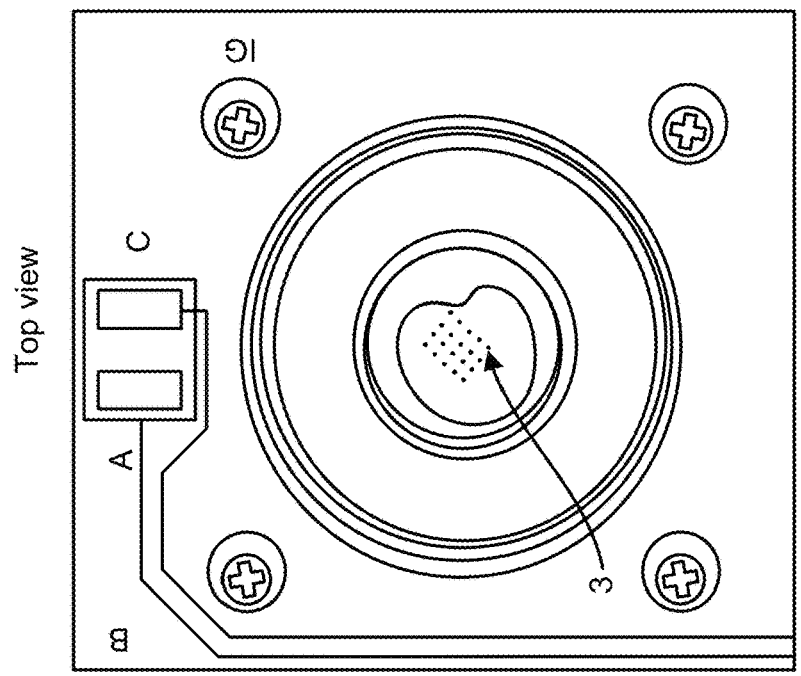
FIGS. 9A-9B show an embodiment of a testing apparatus for measuring differential pressure induced leakage in an embodiment of a reservoir, fluid loading plate and ejector assembly (FIG. 9A, side view, FIG. 9B, top view) in accordance with an aspect of the disclosure.
Figure 9A:
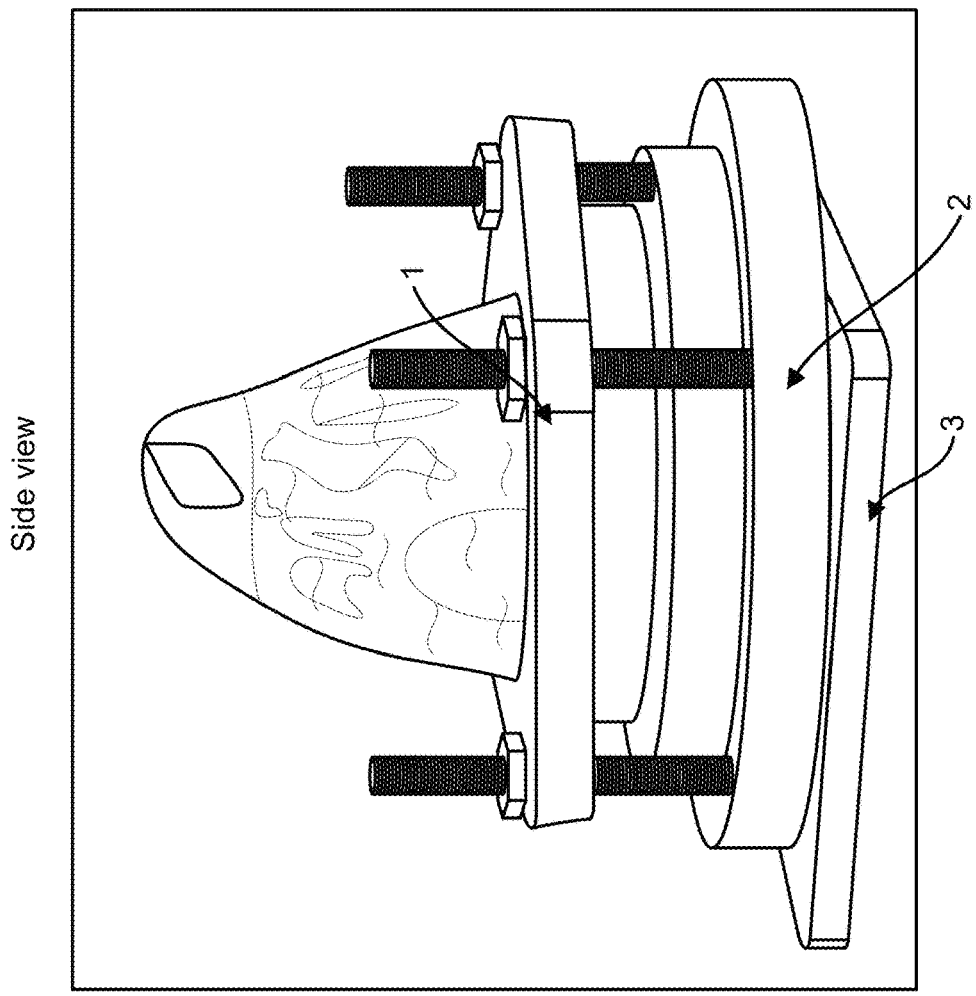
Figure 10A:
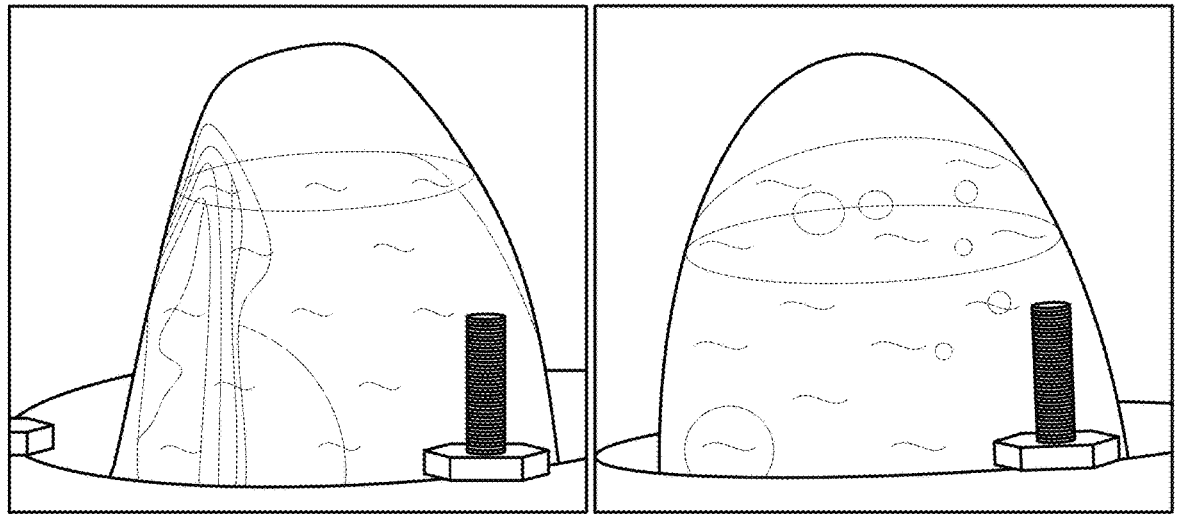
FIGS. 10A-10E illustrate reservoir expansion following a decrease in pressure and a determination of the leak point pressure for embodiments of a reservoir, fluid loading plate and ejector assembly, in accordance with aspects of the disclosure.
Figure 10B:
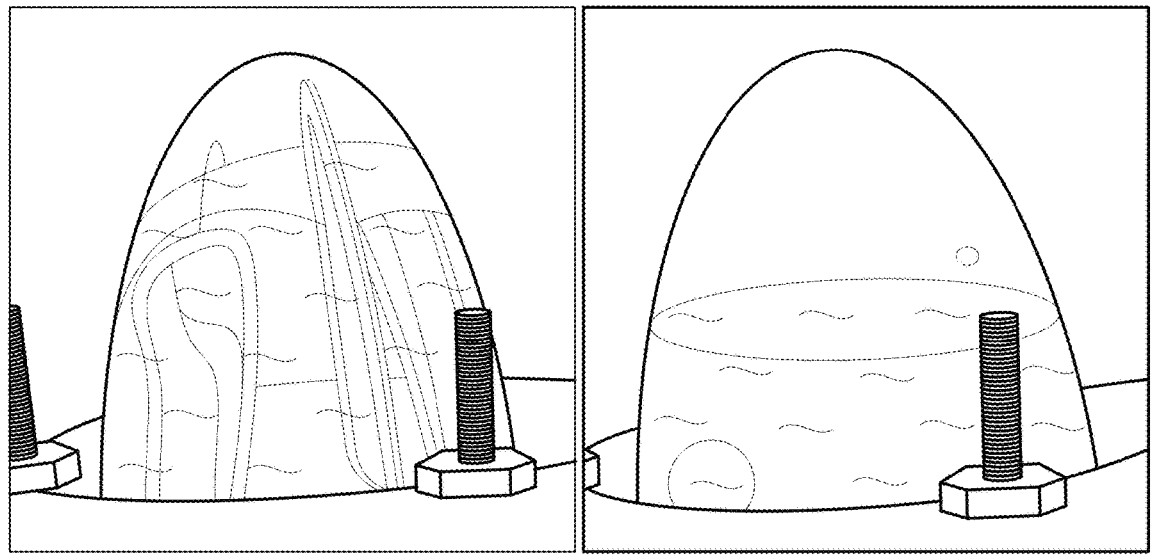
Figure 10C:
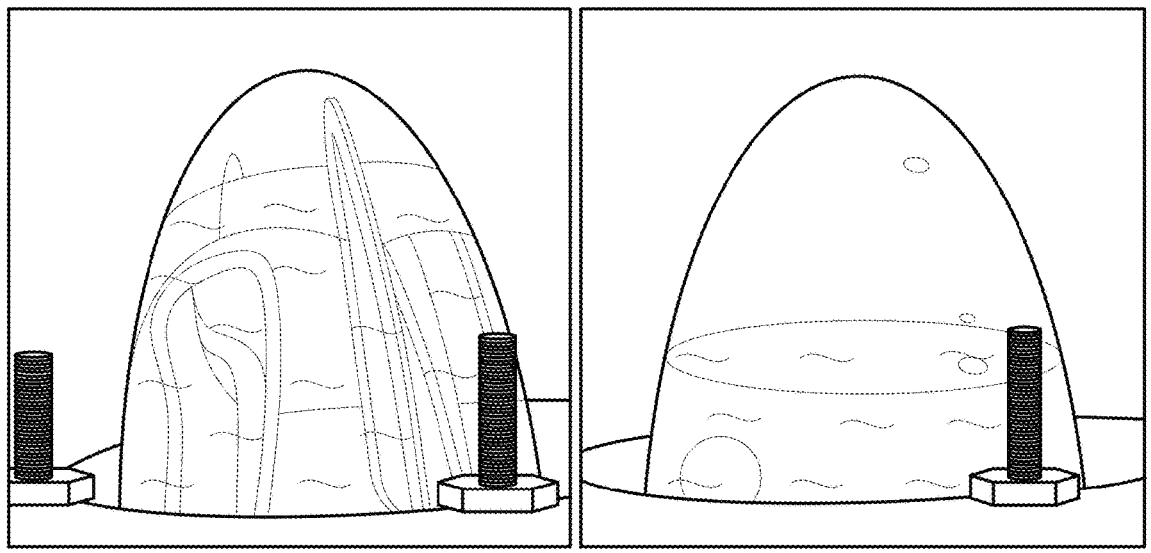
Figure 10D:
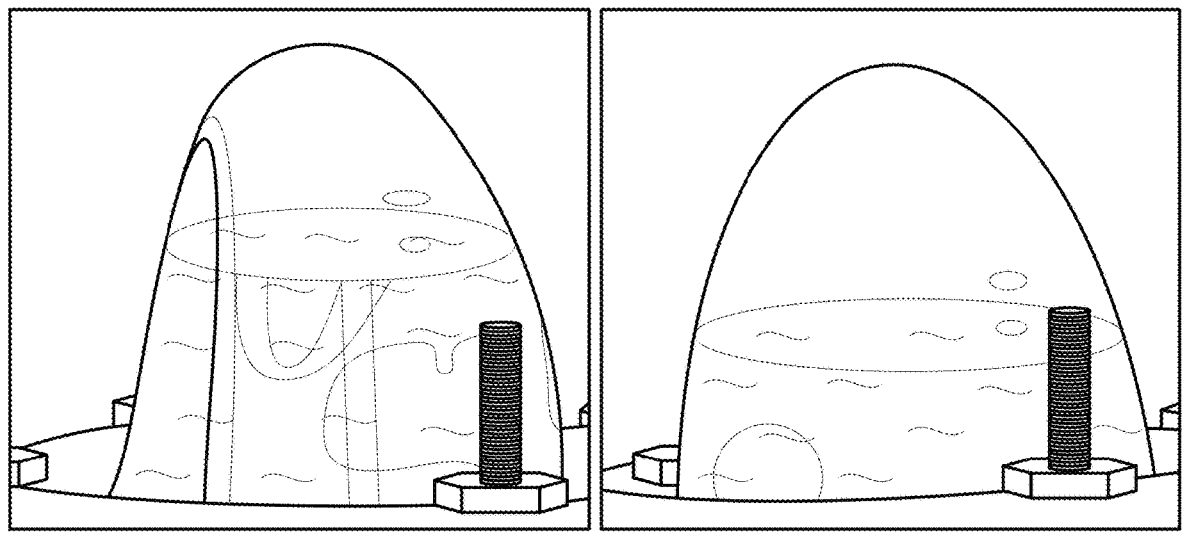
Figure 10E:
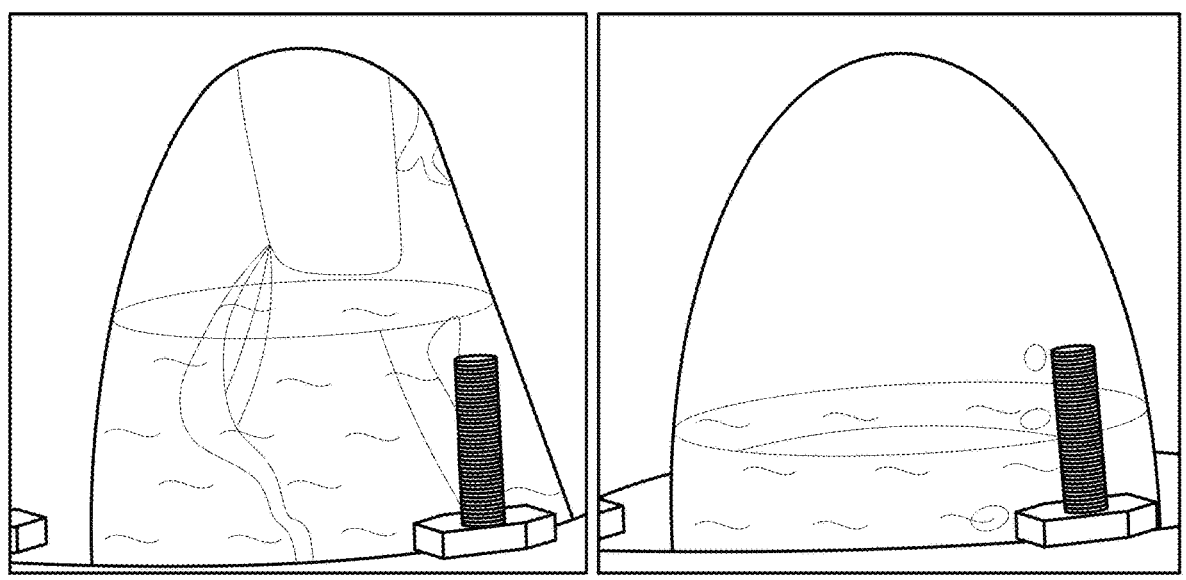

FIG. 9 shows an assembly that allows an assembly of container, fluid loading plate and ejector device to be tested for leakage as the pressure is decreased. The fluid filled container is mounted onto a leak pressure test apparatus which consists of an ampoule retaining mount (1), fluid loading plate (2), which delivers fluid behind the ejector plate (3). The leak pressure test apparatus is placed within a vacuum chamber that is pumped by a mechanical pump suitable for attaining 2.75 psi. At this pressure (2.75 psi) the measured pressure differential between STP (13.23 psi) and the lowest measurable leakage pressure (2.75 psi) is 10.5 psi, or 72.3 kPa. Leakage at this pressure is equivalent to a pressure differential encountered in traveling from sea level to 31,000 feet. FIG. 9 also illustrates an aspect of the container having a $V_r$ greater than zero. Thus, the container provides for expansion of the gas as the ambient pressure is decreased inside the vacuum chamber. Variation of the $V_r$ can affect the leak pressure.

Table 3 provides the results of leak pressure testing through 40 um holes on a 12 mm deep (e.g., depth 607 of FIG. 6) flexible container.

TABLE 3

Leak pressure test through 40 um holes with 12 mm deep flexible container

| Experiment #: | % Full (%) | % Air Volume | Delta P (psi) | Delta P (kPa) |
| --- | --- | --- | --- | --- |
| 1 | 97.20 | 3.43 | 1.66 | 11.43 |
| 2 | 93.20 | 8.34 | 2.45 | 16.91 |
| 3 | 77.38 | 22.70 | 0.99 | 6.80 |
| 4 | 81.89 | 18.18 | 1.16 | 8.00 |
| 5 | 87.72 | 12.32 | 3.51 | 24.18 |

TABLE 3-continued

Leak pressure test through 40 um holes with 12 mm deep flexible container

| Experiment #: | % Full (%) | % Air Volume | Delta P (psi) | Delta P (kPa) |
|---|---|---|---|---|
| 6 | 85.28 | 14.77 | 1.80 | 12.41 |
| 7 | 81.17 | 18.90 | 1.89 | 13.05 |
| 8 | 73.31 | 26.79 | 1.00 | 6.89 |

Table 4 provides the results of leak pressure testing through 20 um holes on a 20 mm deep flexible container.

TABLE 4

Leak pressure test through 20 um holes with 20 mm deep flexible container

| Experiment #: | % Air Volume | Start Pressure (psi) | Leak Pressure (psi) | Delta P (psi) | Delta P (kPa): |
|---|---|---|---|---|---|
| 1 | 3.13 | 13.23 | 2.75 | 10.48 | 72.26 |
| 2 | 3.13 | 13.26 | 2.95 | 10.31 | 71.09 |
| 3 | 15.63 | 13.26 | 6.40 | 6.86 | 47.30 |
| 4 | 9.38 | 13.26 | 5.95 | 7.31 | 50.40 |
| 5 | 6.25 | 13.25 | 3.75 | 9.50 | 65.50 |
| 6 | 12.50 | 13.25 | 5.95 | 7.30 | 50.33 |
| 7 | 9.38 | 13.25 | 5.25 | 8.00 | 55.16 |

Table 5 provides the results of leak pressure testing through 40 um holes on a 20 mm deep flexible container.

TABLE 5

Leak pressure test on 20 mm flexible container with 40 um holes

| Experiment #: | % Air Volume | Start Pressure (psi) | Leak Pressure (psi) | Delta P (psi) | Delta P (kPa): |
|---|---|---|---|---|---|
| 1 | 2.3 | 13.28 | 2.75 | 10.53 | 72.6 |
| 2 | 6.3 | 13.28 | 3.18 | 10.1 | 69.6 |
| 3 | 9.4 | 13.28 | 5.2 | 8.08 | 55.7 |
| 4 | 12.5 | 13.28 | 5.5 | 7.78 | 53.6 |
| 5 | 15.6 | 13.28 | 5.9 | 7.38 | 50.9 |
| 6 | 18.8 | 13.27 | 6.15 | 7.12 | 49.1 |
| 7 | 21.9 | 13.27 | 6.35 | 6.92 | 47.7 |

Table 6 provides the results of leak pressure testing through 40 um holes on a 20 mm deep hard container.

TABLE 6

Leak Pressure Test on Hard container with 40 um holes

| Experiment #: | % Air Volume | Start Pressure (psi) | Leak Pressure (psi) | Delta P (psi) | Delta P (kPa): |
|---|---|---|---|---|---|
| 1 | 12.5 | 13.25 | 12.85 | 0.4 | 2.8 |
| 2 | 4.2 | 13.25 | 12.75 | 0.5 | 3.4 |
| 4 | 29.2 | 13.25 | 12.75 | 0.5 | 3.4 |
| 5 | 37.5 | 13.25 | 12.7 | 0.55 | 3.8 |
| 8 | 20.8 | 13.25 | 12.72 | 0.53 | 3.7 |

FIG. 10 illustrates the results of container expansion as a mechanism of pressure equalization. As tested in Example 1 and presented in Table 4, as the pressure is decreased, the gas expands, causing an expansion of the collapsed volume $V_r$. As $V_{gas}$ approaches the total volume $V_{AT}$ the tendency of the apparatus to leak increases. Smaller volumes of air are generally associated with lower leak point pressures. Delta P represents the pressure at which the combination begins to leak.

FIG. 11 graphically presents the results of leak pressure testing of different embodiments of the present disclosure. As shown, a hard reservoir leaks at low differential pressures that is independent of the % air volume (e.g., $V_{air}/V_t$). The 12 mm deep container (ampoule) requires higher differential pressures to induce leakage and a maximal pressure of about 25 is observed for about a 12% air volume. A 20 mm deep container having either 40×160 um holes or 20×40 um holes, requires the highest differential pressures to cause leakage. In these embodiments, the hole number and size were not distinguishable.

Example 2: Measurement of Mass Loss Over Time

FIG. 12 shows the mass loss from an ampoule (reservoir) over time to determine the storage ability of ampoules (reservoirs) of the present disclosure. A series of reservoirs are stored for 72 days and the amount of mass determined. From a total volume of 3.5 ml, a total volume of 50 μl escapes over the time period.

Experiment 3. Measurement of Ejection Volume at Different Attitude Angles

FIG. 13 shows the ejection volume at differing attitude angles over a range of frequencies of a piezoelectric ejector device having either a hard reservoir or a flexible reservoir. The flexible ampoule design provides more consistent ejection of fluid volume over a broader frequency range and fill level.

Although the foregoing describes various reservoir embodiments by way of illustration and example, the skilled artisan will appreciate that various changes and modifications may be practiced within the spirit and scope of the present application. As used herein, a reservoir may be any object suitable for holding a fluid. By way of example, the reservoir may be made of any suitable material capable of containing a fluid. Reservoirs of the present disclosure may be rigid or flexible and the reservoirs of the present disclosure may further be collapsible. As used herein, collapsible refers to a decrease in volume obtainable in a reservoir achieved by squeezing, folding, crushing, compressing, vacuuming, or other manipulation, such that total volume enclosed after collapsing is less than a volume that could be enclosed in a non-collapsed container. A reservoir may be made of any suitable material that can formed into a volume capable of holding a volume of fluid. Suitable materials, for example, may either be flexible or rigid and may be formable or pre-formed. As used herein a reservoir, by way of example, may be formed from a film.

In other aspects, a fluid loading plate of the disclosure may be integrated into an ejector device between a reservoir and an ejector mechanism. In certain embodiments, the ejector device may be for delivering a fluid to an eye of a subject, and may comprise a housing, a reservoir disposed within the housing for receiving a volume of fluid, the reservoir being in fluid communication with a fluid loading plate, the fluid loading plate being in fluid communication with an ejector mechanism such that the fluid loading plate provides fluid to a rear ejection surface of an ejector mechanism, wherein the ejector mechanism is configured to eject a stream of droplets of a fluid. The ejector mechanism may be configured to eject a stream of droplets having an average ejected droplet diameter greater than 15 microns, with the stream of droplets having low entrained airflow such that the stream of droplets deposits on the eye of the subject during use.

In certain embodiments, the ejector mechanism may comprise an ejector plate and a piezoelectric actuator; the ejector plate including a plurality of openings formed through its thickness; and the piezoelectric actuator being operable to oscillate the ejector plate at a frequency, and generate a directed stream of droplets. In certain aspects, the ejector plate may be formed from a high modulus polymer material.

In certain embodiments, the piezoelectric actuator is coupled to a peripheral region of the ejector plate so as not to obstruct the plurality of openings of the ejector plate. The plurality of openings of the ejector plate may be disposed in a center region of the plate that is uncovered by the piezoelectric actuator. In certain embodiments, the three-dimensional geometry and shape of the openings, including orifice diameter and capillary length, and spatial array on the ejector plate may be controlled to optimize generation of the directed stream of droplets.

By way of example, the fluid loading plate may be integrated into an ejector device or ejector assembly, or configured to interface with an ejector mechanism as disclosed, for example, in the applications: U.S. Application No. 61/591,786, filed Jan. 27, 2012, entitled "High Modulus Polymeric Ejector Mechanism, Ejector Device, and Methods of Use"; U.S. Application No. 61/569,739, filed Dec. 12, 2011, entitled "Ejector Mechanism, Ejector Device, and Methods of Use"; and U.S. application Ser. No. 13/184,484, filed Jul. 15, 2011, entitled "Drop Generating Device", which applications are each herein incorporated by reference in their entireties.

Many embodiments and implementations of the invention are disclosed herein. This disclosure contemplates combining any of the features of one embodiment with the features of one or more of the other embodiments. For example, any of the ejector mechanisms or reservoirs can be used in combination with the fluid loading plate, as well as any of the housings or housing features discussed in the incorporated references, e.g., covers, supports, rests, lights, seals and gaskets, fill mechanisms, or alignment mechanisms. Further variations on any of the elements of any of the aspects of the present disclosure that are within the scope of ordinary skill are contemplated by this disclosure. Such variations include selection of materials, coatings, or methods of manufacturing.

Figure 14A:
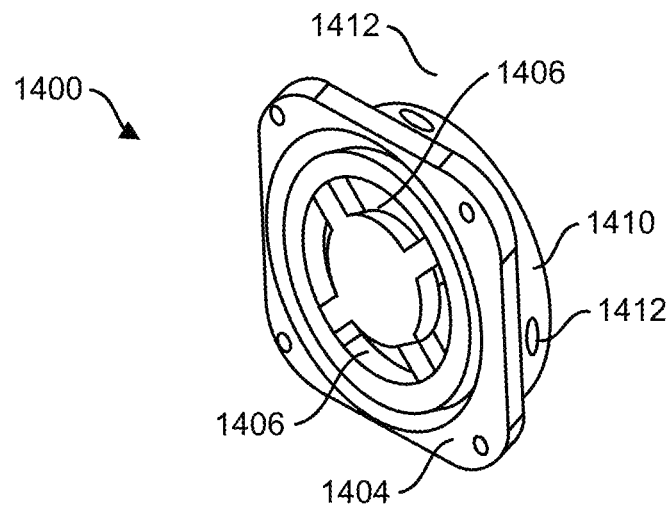
FIGS. 14A-14C show one embodiment of a capillary plate of the disclosure.
Figure 14B:
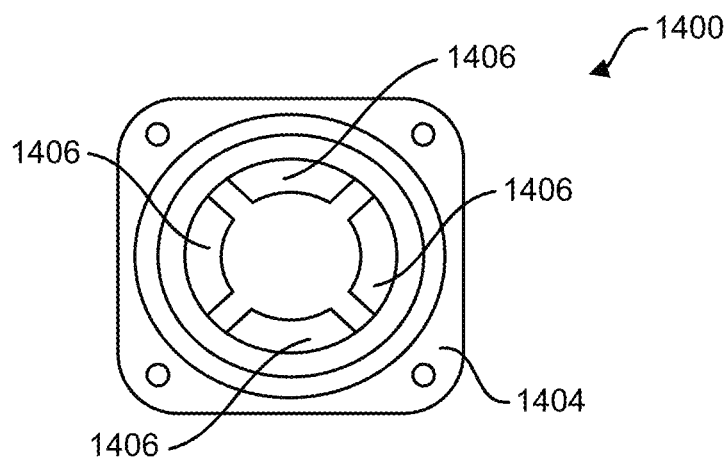
Figure 14C:
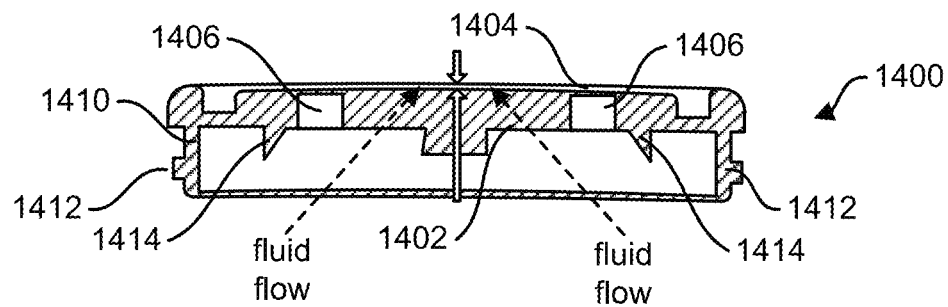

With reference to FIGS. 14A-14C, in one embodiment, the fluid loading plate may comprise a capillary plate 1400 including a fluid reservoir interface 1402, an ejector mechanism interface 1404, and one or more fluid openings 1406. If desired, the capillary plate 1400 may optionally include a reservoir housing mating ring 1410 to facilitate connection with various reservoir housing configurations (not shown), as described in U.S. application Ser. No. 13/184,484, filed Jul. 15, 2011, entitled "Drop Generating Device", which is herein incorporated by reference in its entirety.

In addition, the capillary plate 1400 may optionally include fastening clips 1412 on the housing mating ring 1410 to secure capillary plate 1400 to a reservoir housing (not shown). Although exemplary clip configurations and positions are shown, different embodiments and positions are envisioned and within the scope of the disclosure. Capillary plate 1400 may also include piercing projections 1414 on the fluid reservoir interface 1402 to facilitate opening of various reservoir housing configurations (not shown). Again, although exemplary piercing projections and positions are shown, different embodiments and positions are envisioned and within the scope of the disclosure. For instance, the piercing projections may be sized and shaped so as not to hinder fluid flow through the one or more fluid openings 1406.

With reference to FIGS. 15A-15C, in certain embodiments, the ejector mechanism interface 1502 of the capillary plate 1500 is placed in parallel arrangement with a rear ejection surface 1506 of the ejector mechanism 1504 so as to form a separation 1508 between the capillary plate and the ejector mechanism, and generate fluid flow 1510 between the capillary plate 1500 and the ejector mechanism 1504 in the capillary fluid loading area 1512 at the rear ejection surface of the ejector mechanism. This fluid flow 1510 allows the capillary plate 1500 to provide fluid to the rear ejection surface 1506 of the ejector plate 1514 of the ejector mechanism. The configuration of the capillary plate provides for consistent supply and delivery of fluid in the capillary fluid loading area at the rear ejection surface 1506 of the ejector plate 1514. As a result, a consistent volume of droplets is generated by the ejector mechanism, regardless of fluid level and device orientation (i.e., attitude).

Figure 16A:
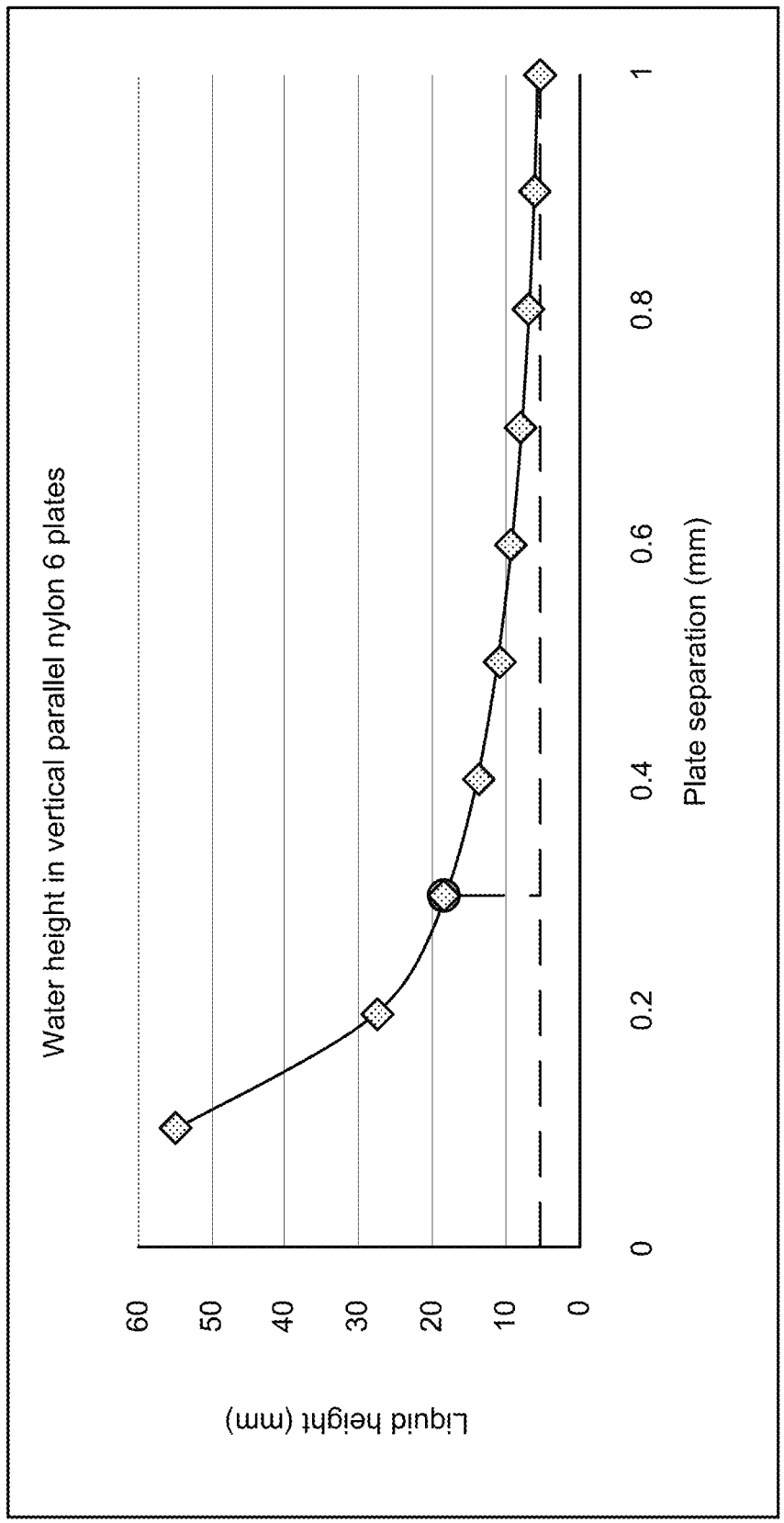
FIGS. 16A-16B illustrate the relationship between plate separation and water height in vertical parallel plates.
Figure 16B:
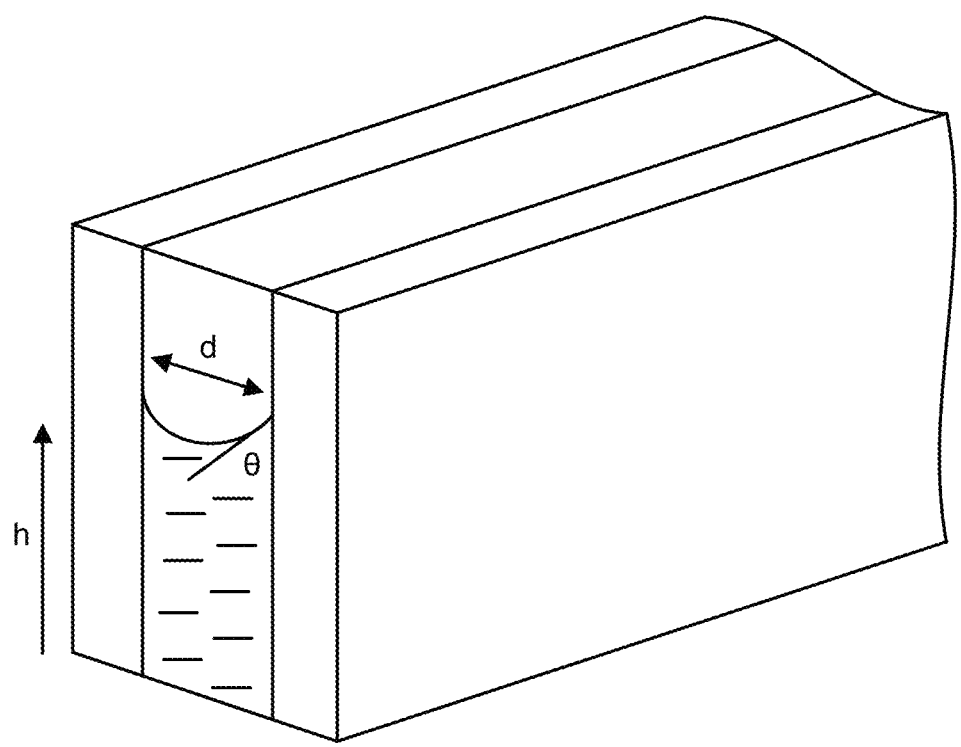

With reference to FIGS. 16A and 16B, the fluid loading between the parallel surfaces of the capillary plate and the ejector plate is dependent upon distance d of the capillary plate separation. As is shown in FIG. 16A, plate separation of up to 1 mm provides adequate fluid loading (liquid height) in the capillary fluid loading area. In certain embodiments, a separation distance between the capillary plate and the ejector mechanism of between about 0.2 mm and about 0.5 mm, more particularly between about 0.2 and about 0.4 mm, or more particularly of 0.3 mm may be used.

Without intending to be limited by theory, general expressions for capillary rise between two parallel surfaces are set out below:

$$\langle h \rangle = \frac{\gamma_{lv}(\cos(\theta_1) + \cos(\theta_2))}{\rho g d}; h = \frac{2\gamma_{lv}\cos(\theta)}{\rho g d}$$

where:
h is the liquid height;
$\gamma_{lv}$ is the liquid vapor surface tension in contact with a surface;
θ is the contact angle between the fluid and the surface;
ρ is density difference between fluid and vapor;
g is acceleration of gravity; and
d is the separation distance between surfaces.

The fluid loading plate may be formed from any suitable materials for use in the intended application. By way of example, in ophthalmic applications, any suitable material for use in pharmaceutical ophthalmic applications may be used, such as polymeric materials that do not chemically react with or adsorb fluids to be delivered. In certain embodiments, the surfaces of the fluid loading plate that are exposed to the fluid to be delivered may be formed from materials that provide desired surface properties, including hydrophilic/hydrophobic properties, surface energy, etc., so as to facilitate wicking and capillary action between the parallel surfaces. For example, see U.S. Pat. No. 5,200,248 to Thompson et al., which is herein incorporated by reference.

In certain embodiments, the fluid loading plate may be formed from a single material, e.g., in a capillary plate embodiment. In other aspects, the fluid loading plate may be a composite formed from more than one material wherein the surfaces that are exposed to the fluid to be delivered are selected so as to have desired surface properties. By way of example, a capillary plate may be injection molded or thermoformed as a unitary piece or as separate pieces. If desired, one or more reservoir mating surfaces may be separately formed, or formed as a unitary piece with other components of the capillary plate. Without intending to be limiting, and by way of example, materials include: polyamides including nylons such nylon-6, HDPE, polyesters, co-polyesters, polypropylene, and other suitable pharmaceutical grade hydrophilic polymers or polymeric structures.

Figure 17B:
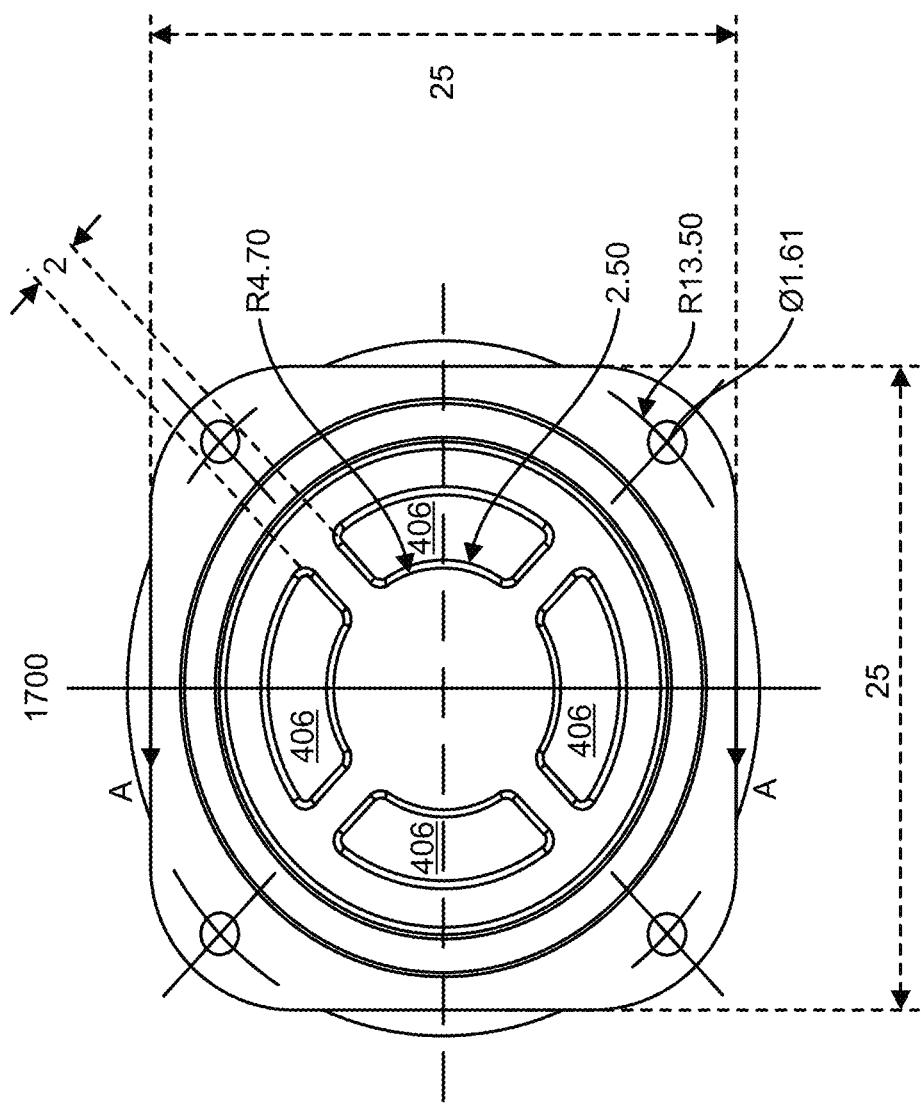
FIGS. 17A-17B show an embodiment of a capillary plate of the disclosure.
Figure 17A:
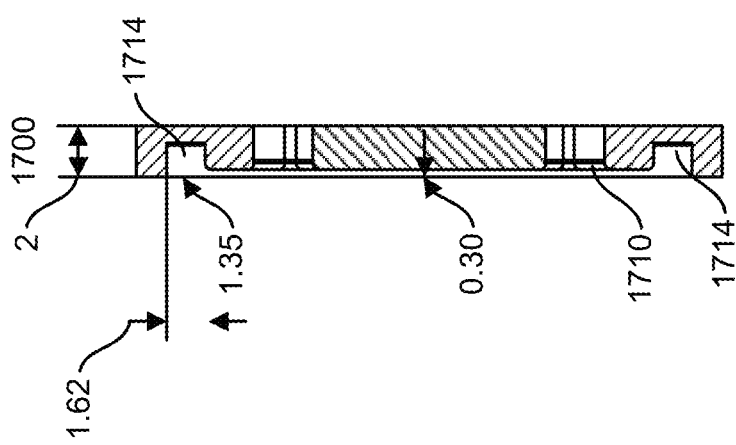

The fluid loading plate may be sized and shaped in any suitable manner so as to interface with the desired ejector mechanism such that fluid is provided to and a suitable capillary fluid loading zone is formed at the ejector mechanism interface between the capillary plate and the rear ejector surface of the ejector mechanism. With reference to FIGS. 17A and 17B, one embodiment of a capillary plate 1700 is illustrated. However the sizes given in FIGS. 17A and 17B are for illustration purposes only, and the disclosure is not so limited. By way of example, capillary plate 1700 may be generally square shaped and have an edge length of about 25 mm. However, other shapes are envisioned, including generally circular configurations, etc. Four separated fluid openings 1706 are shown about an annular radius of about 4.70 mm, having a general opening width of about 2.50 mm and a spacing of about 2 mm. The thickness of the fluid flow portion of capillary plate 1700 (i.e., the portion of capillary plate 1700 including fluid opening 1706) may be about 0.30 mm, and the thickness of the housing mating ring 1710 of capillary plate 1700 may be about 2 mm Piercing projections 1714 may be, e.g., about 1.62 mm across and about 1.35 mm in length to provide for desired protrusion properties while still allowing for fluid flow.

To assist in understanding the present invention, FIGS. 18-22 illustrate various effects of the use of a fluid loading plate described herein on the performance of an ejector device. The experiments described herein should not be construed as specifically limiting the invention and such variations of the invention, now known or later developed, which would be within the purview of one skilled in the art are considered to fall within the scope of the invention as described herein and hereinafter claimed.

Figure 18:
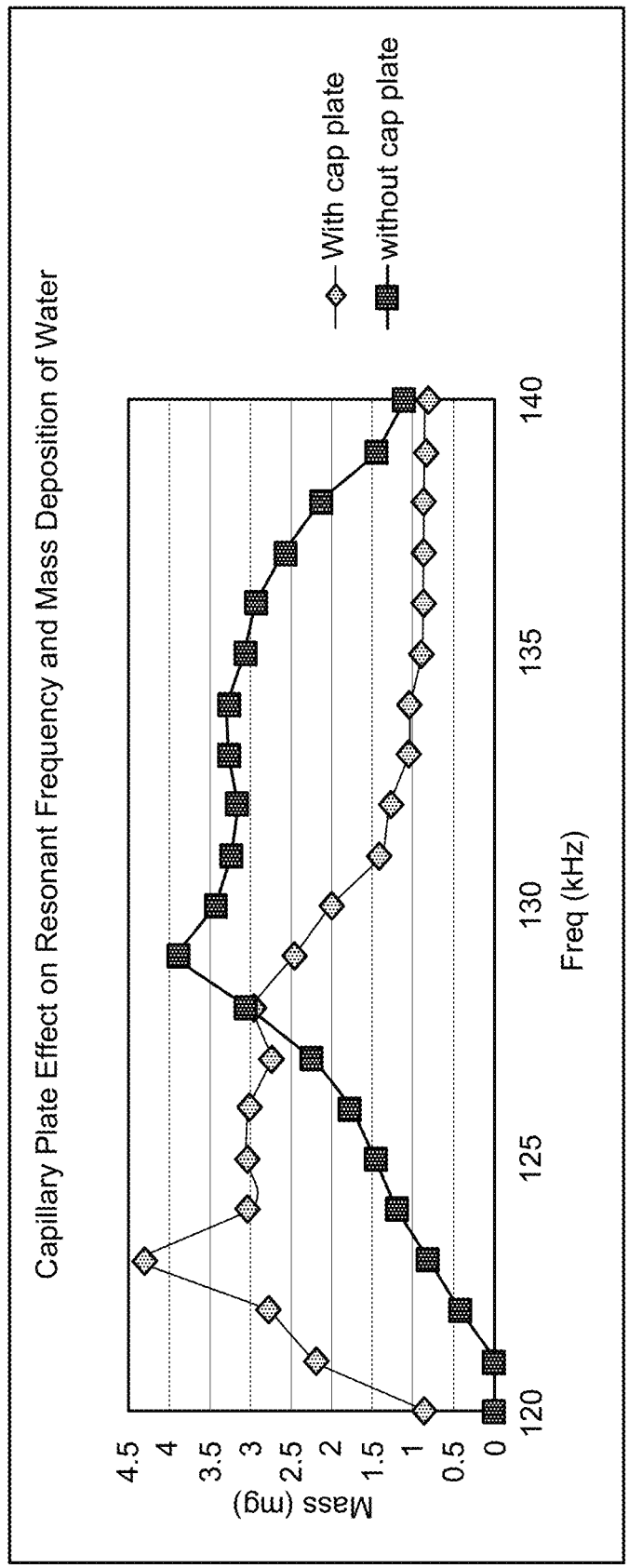
FIG. 18 shows the effect of resonant frequency on mass deposition of water with and without a capillary plate.

More specifically, FIG. 18 illustrates the effects of a capillary plate on resonant frequency and mass deposition of water using a 160 micron thick NiCo ejector plate with 25 and 40 micron holes, showing a downward shift in frequency. FIG. 19 illustrates that as the density (and therefore the mass) of a fluid in a resonant system (such as the capillary region behind the ejector plate) increases, so there is a downward shift in the resonant frequency. FIG. 20 illustrates the downward shift in frequency associated with a capillary plate used with the delivery of various fluids using a 160 micron thick NiCO ejector plate with 25 and 40 micron holes. FIG. 21 illustrates both a reduction in resonant frequency and amplitude of the resonant structure as the density ($\varphi$ and viscosity ($\eta$) of the fluid in the resonant system are increased. By way of example, and not necessarily related to the particular values in the graph of FIG. 21, the densities and viscosities of water, ethanol and propylene glycol are given in the table below the graph. As shown in FIGS. 18-21, the presence of a capillary plate leads to an overall shift in resonance frequency, to lower frequencies. The shift in volume sprayed for liquids is a consequence of increased density and viscosity, (water, ethanol, and propylene glycol).

FIG. 22 illustrates the attitude insensitivity of an ejector device that includes a capillary plate. As shown, volume (mass) delivered is relatively insensitive to ejector device orientation. This insures a constant delivery and supply of fluid behind the ejector plate. As a result, a consistent volume of droplets is formed and sprayed by the ejector mechanism, regardless of fluid level and device orientation.

In other embodiments, the fluid loading plate may comprise a puncture plate fluid delivery system, also referred to as a capillary/puncture plate fluid delivery system, which is configured to deliver fluid from the reservoir to a fluid retention area at the back of the ejector mechanism for delivery as a directed stream of droplets via piezoelectric ejection. Without intending to be limited by theory, the puncture plate system may utilize one or more of hydrostatic pressure, capillary pressure, geometrical pressure gradients (Venturi effect), and air exhaustion.

One embodiment of a puncture plate fluid delivery system and its operation is shown in FIGS. 23-27. FIGS. 23A and B show a front view and a back view, respectively, of an ejector mechanism 2300 with 5 rise holes 2302. As shown in front view in FIG. 23C and in back view in FIG. 23D, the puncture plate fluid delivery system may include a capillary plate portion comprising a fluid retention area between the puncture/capillary plate fluid delivery system and a rear surface of an ejector mechanism for channeling fluid to the ejector mechanism by one or more mechanisms, including capillary action, and at least one hollow puncture needle for transferring fluid from a reservoir to the fluid retention area. In this embodiment, 6 hollow puncture needles 2306 extend from the back surface of the capillary/puncture plate, the channels through the needles extending through to the front face of the capillary plate 2304 as shown by the holes 2308. The needles 2306 are surrounded by a wall 2310 defining a receptacle for a fitment 2312 (shown in FIG. 23E together with a self-sealing silicone sealing element 2314 that is housed in the fitment 2312).

Initially, the fluid containing reservoir or ampoule 2316 (these terms are used interchangeably herein) is connected to the fitment and is in fluid communication with a secondary reservoir defined by the fitment and the silicone sealing element 2314. The capillary plate 2304 is, in turn, attached to and in fluid communication with the ejector mechanism 2300. However, prior to use, the puncture plate and ejector mechanism 2300 may be provided in a disconnected state from the fitment 2312 and reservoir 2316 to prevent fluid exchange. During the initial stage of connection the hollow puncture needles 2302 shown on the back of the puncture plate image in FIG. 23D are partially inserted into the self-sealing silicone puncture gasket or grommet 2314 that rests inside the fitment 2312. The secondary reservoir formed in the fitment 2312 is constantly open to the fluid in the primary ampoule/reservoir 2316. At this stage, fluid from the primary reservoir that has moved into the secondary reservoir of the fitment 2312 does not enter into the hollow puncture needles 2306, however, due to the barrier created by the self-sealing silicone gasket material 2314.

Puncture is accomplished by pressing the puncture plate needles all the way through the gasket 2314 into the fluid filled fitment by forcing the needles through the silicone gasket. This may occur, e.g., when the fitment snap-fits (indicated by a clicking sound) into the receptacle 2310 of the puncture plate 2304. A seal is maintained after puncture because the silicone gasket 2314 is a compliant and self-sealing material. The initial transfer of fluid from the reservoir/container through the hollow puncture needles immediately after puncture results from a combination of hydrostatic pressure, fitment retention/reservoir volume, and the fluid reaction force from initial puncture which drives the fluid through the capillary tubes defined by the hollow needles and channels in the capillary/puncture plate.

Once the fluid passes through the capillary tubes, surface tension effects dominate the rise of the fluid against gravity. As the fluid rises, it removes air from the system by pushing it out of the front of the ejector openings or holes. Capillary rise holes 2301 are placed on the ejector plate 2320 of the ejector mechanism above the piezoelectric element 2322 that serves as a pressure relief for the air in the system. In the absence of these capillary rise holes 2302, the system would be closed in the region above the ejector openings and the fluid would cease to rise due to the increasing build up in air pressure that eventually equalizes with the capillary pressure. In order to achieve complete rise, all of the air needs to be pushed out of the system. The capillary rise holes 2302 (shown from the back in FIG. 25A and from the front in FIG. 25B) act as pressure equalizing holes and are placed and properly sized (to prevent fluid leaking) and allow the fluid to rise completely thereby ensuring that no (or very little) air remains in the system. The assembled ejector assembly is shown from the front in FIG. 24A and from the rear in FIG. 24B.

Figure 23:
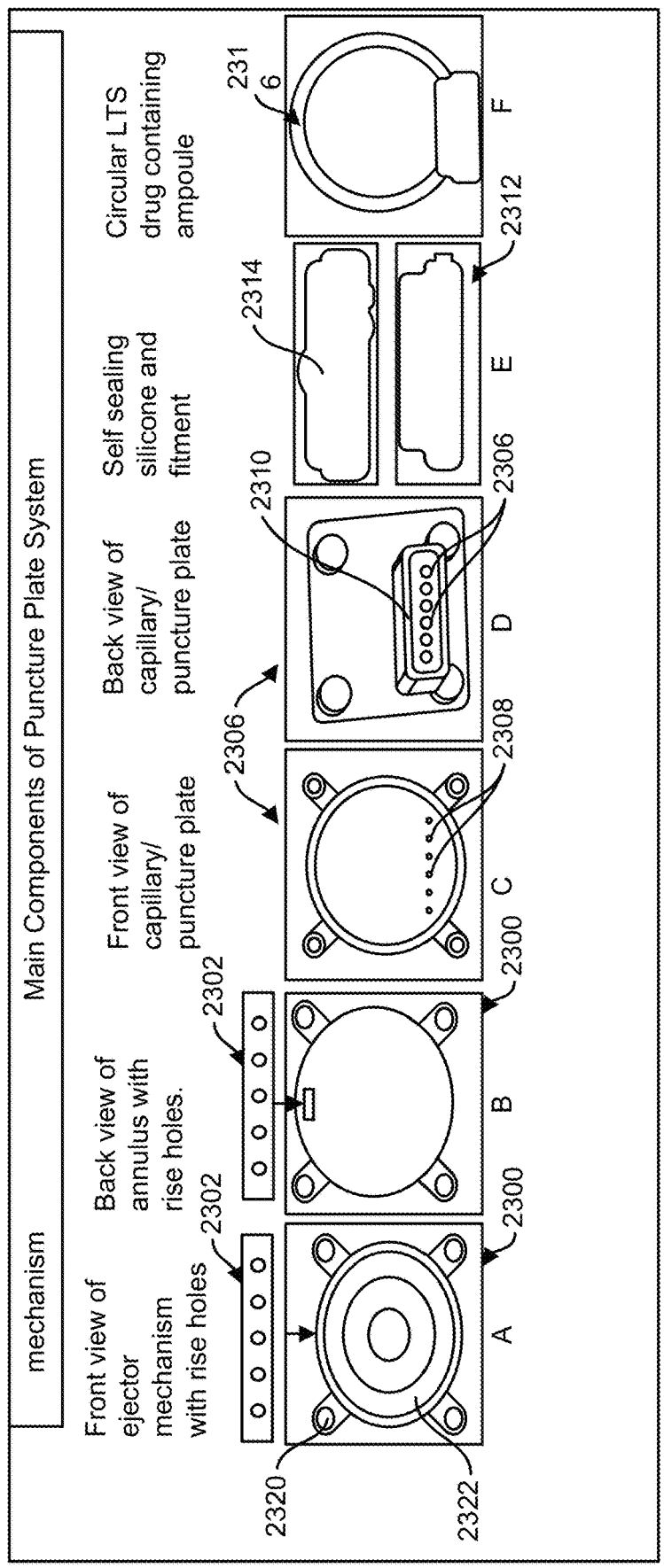
FIG. 23 shows the main components of one embodiment of an ejector assembly including a puncture/capillary plate system with reservoir and ejector mechanism according to the disclosure.
Figures 24A, 24B:
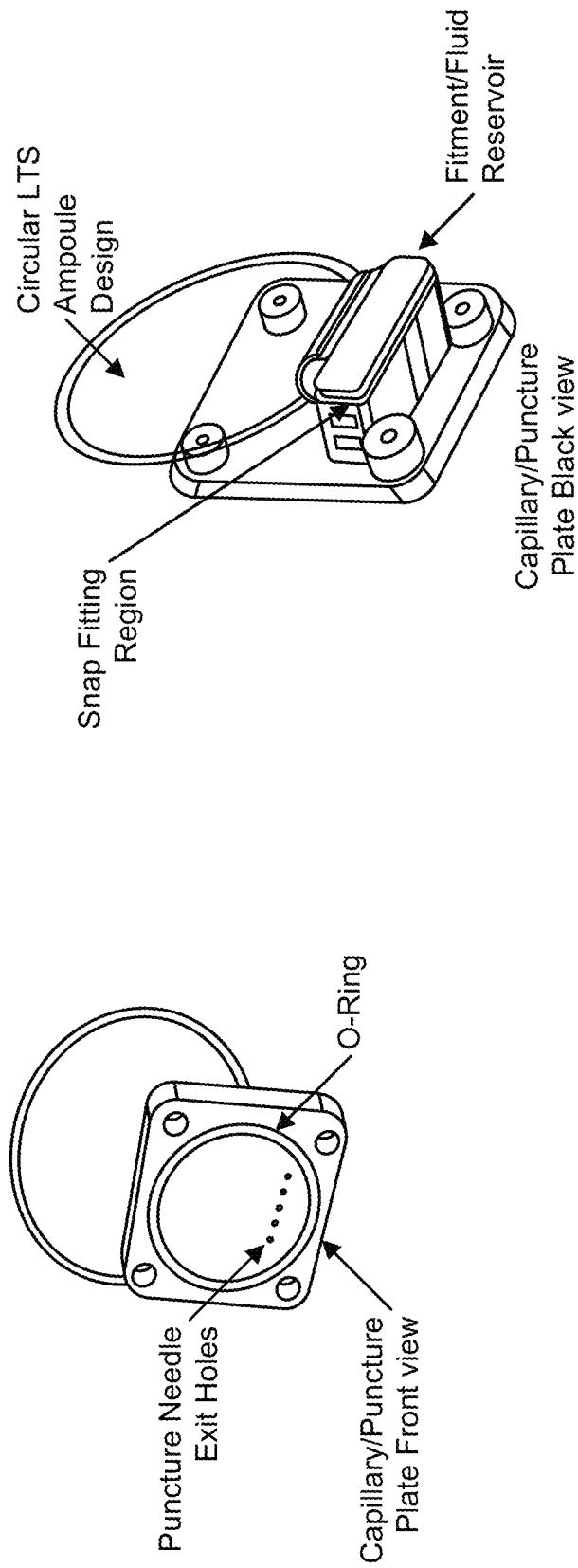
FIGS. 24A-24B show three dimensional front and back view of the components of FIG. 23 in assembled form.
Figure 25B:
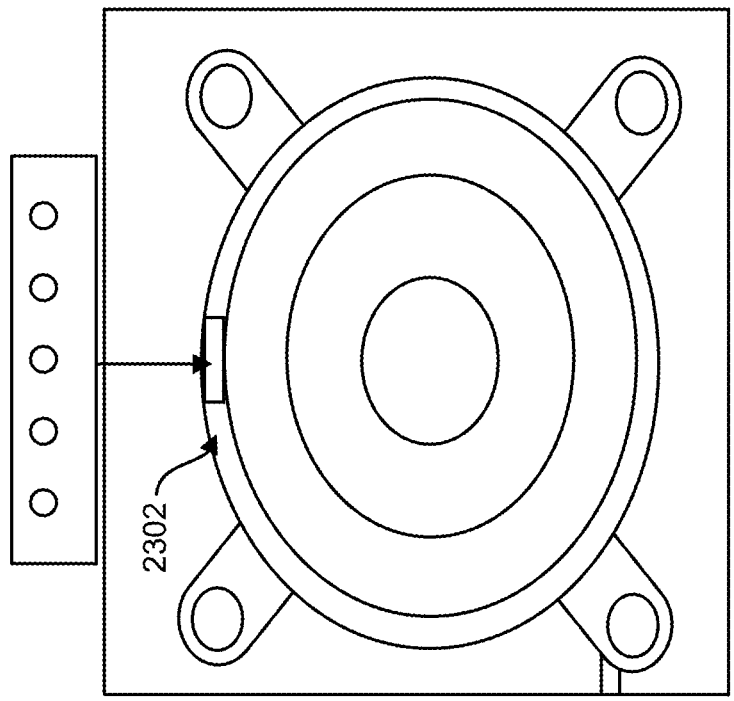
FIGS. 25A-25B show a detailed back and front view of one embodiment of an ejector mechanism of the disclosure.
Figure 25A:
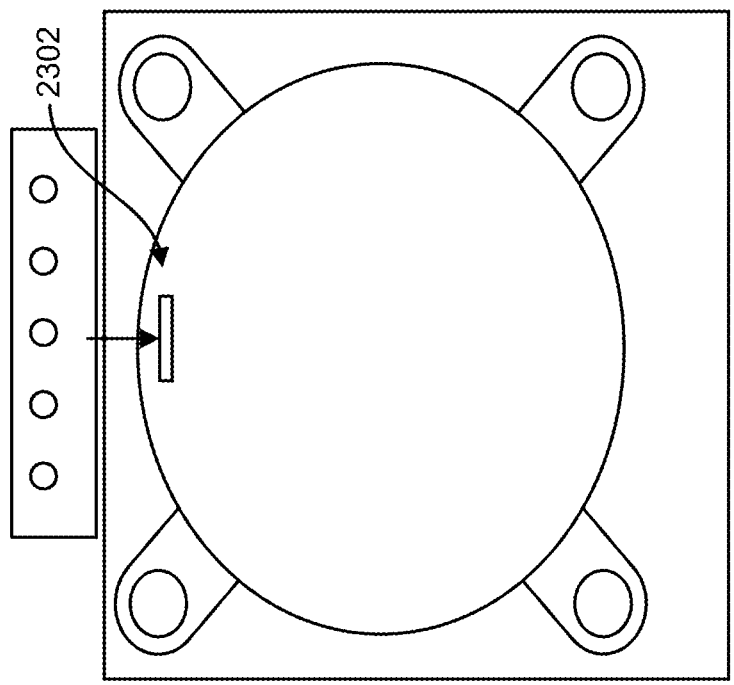
Figure 26:
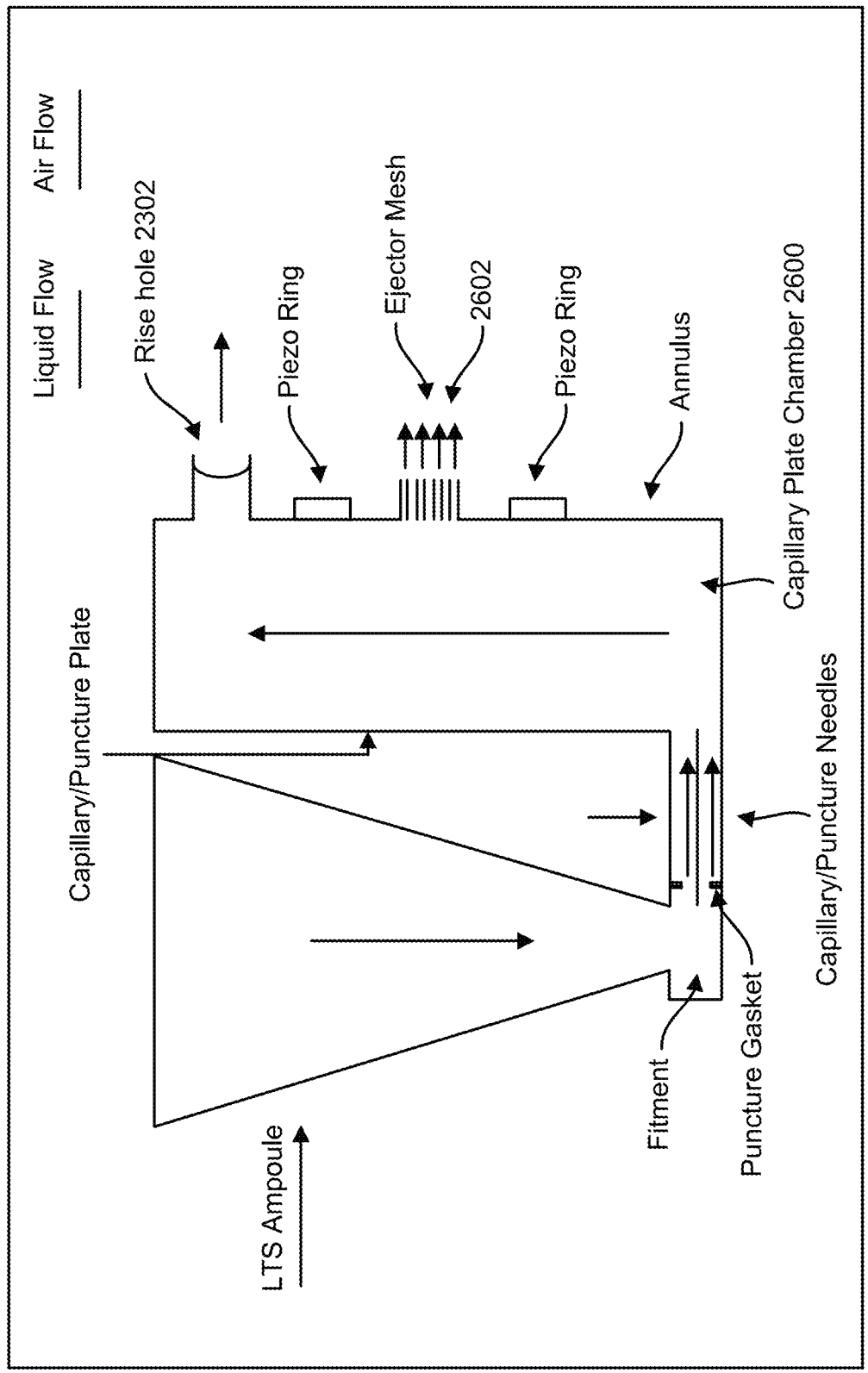
FIG. 26 is a schematic representation outlining fluid flow through a puncture plate system of the disclosure.

FIG. 26 illustrates a schematic outlining fluid flow through the puncture plate system after complete puncture through the silicone gasket. The liquid flows through the puncture system and up the capillary plate chamber 2600, pushing air out of the ejector openings or holes 2602 and capillary rise holes 2302. With reference to FIGS. 23 C and D, the puncture/capillary plate 2304 illustrates a design with 6 needles with an inner diameter (ID) of 650 microns and an outer diameter (OD) of 1 mm. The number of needles can be as small as 1 needle but can also include more needles, e.g., 8 needles with ID dimensions ranging from 500 microns-3 mm and OD dimensions ranging from 600 microns-4 mm. The rise holes shown in FIG. 25 can also vary from what is displayed in this figure. This FIG. shows 5 20 micron diameter sized rise holes however the number of holes can be as low as 1 hole but can also include more holes e.g., 8 holes with the diameter of the holes ranging from 10 microns-50 microns.

Figure 44:
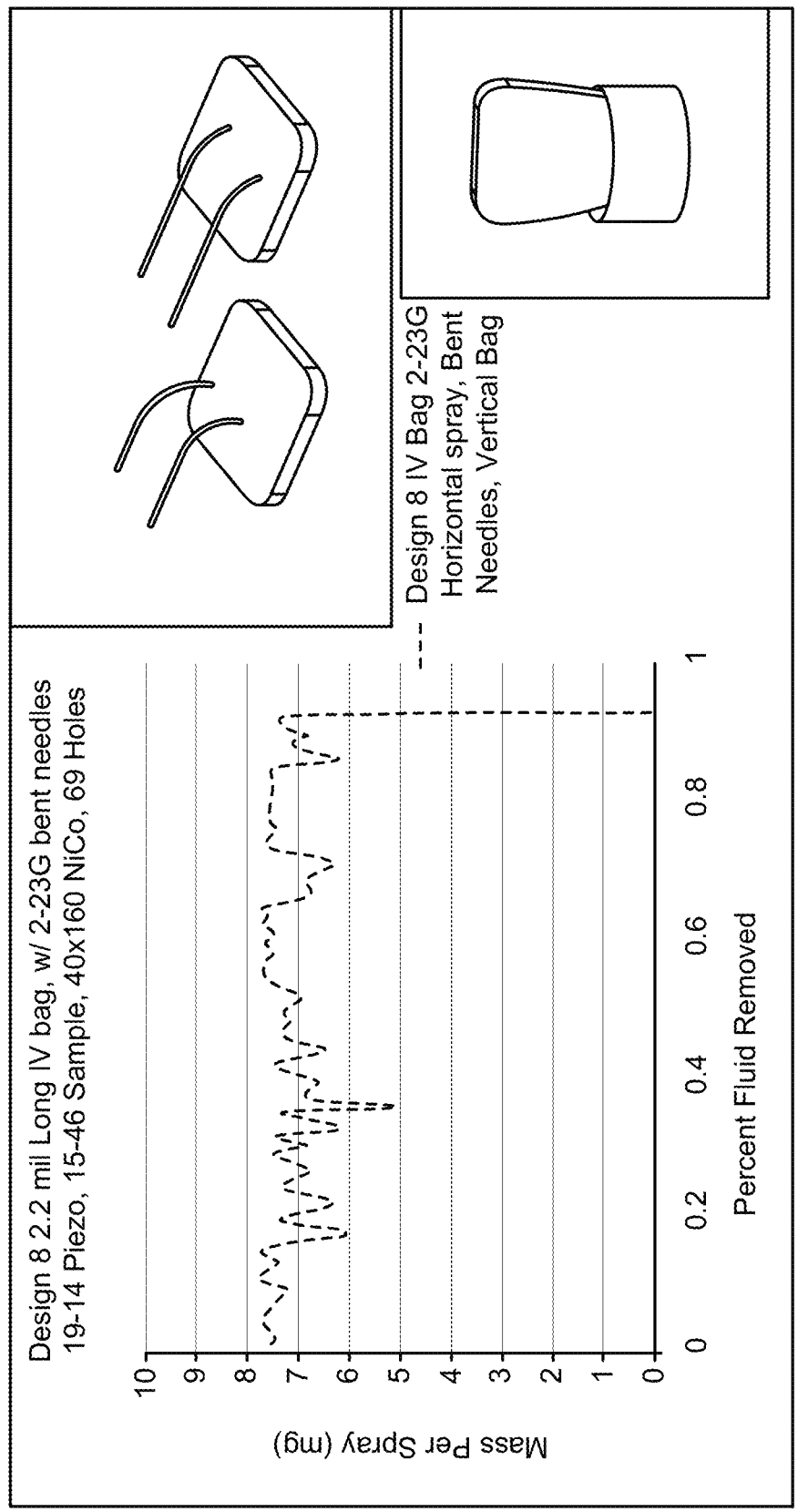
Figure 45:
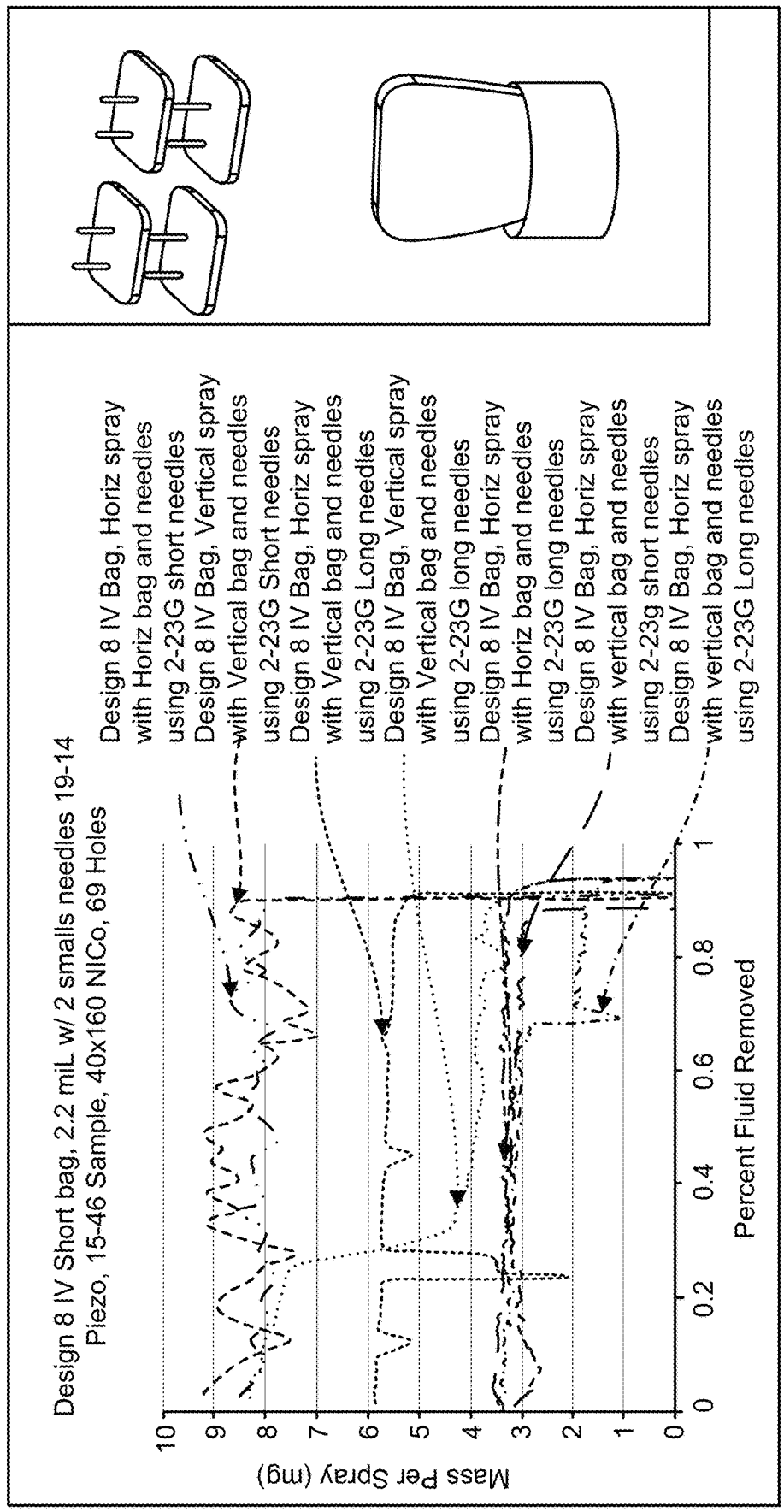
Figure 46:
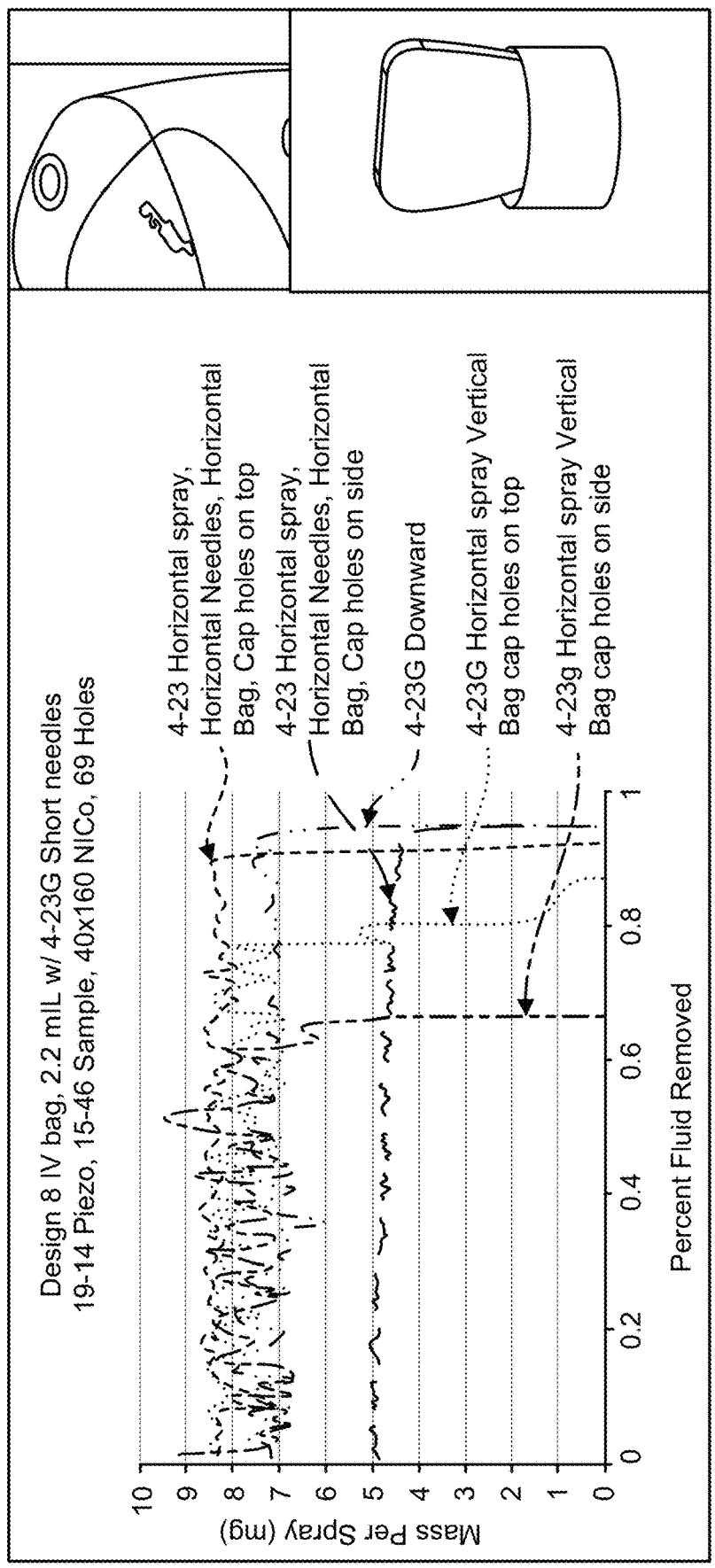
Figure 51:
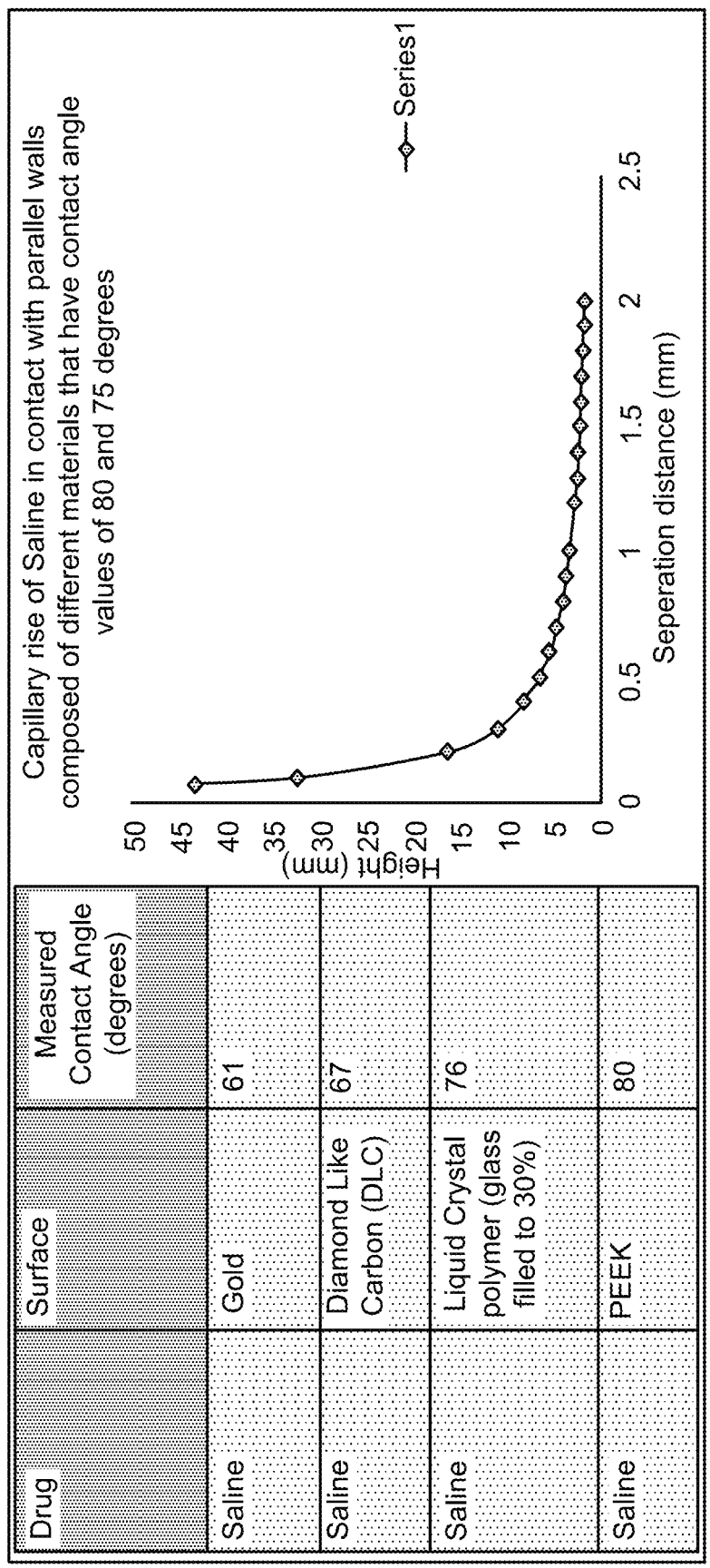
FIG. 51 shows capillary rise for saline in a capillary channel made of different types of materials.
Figure 52:
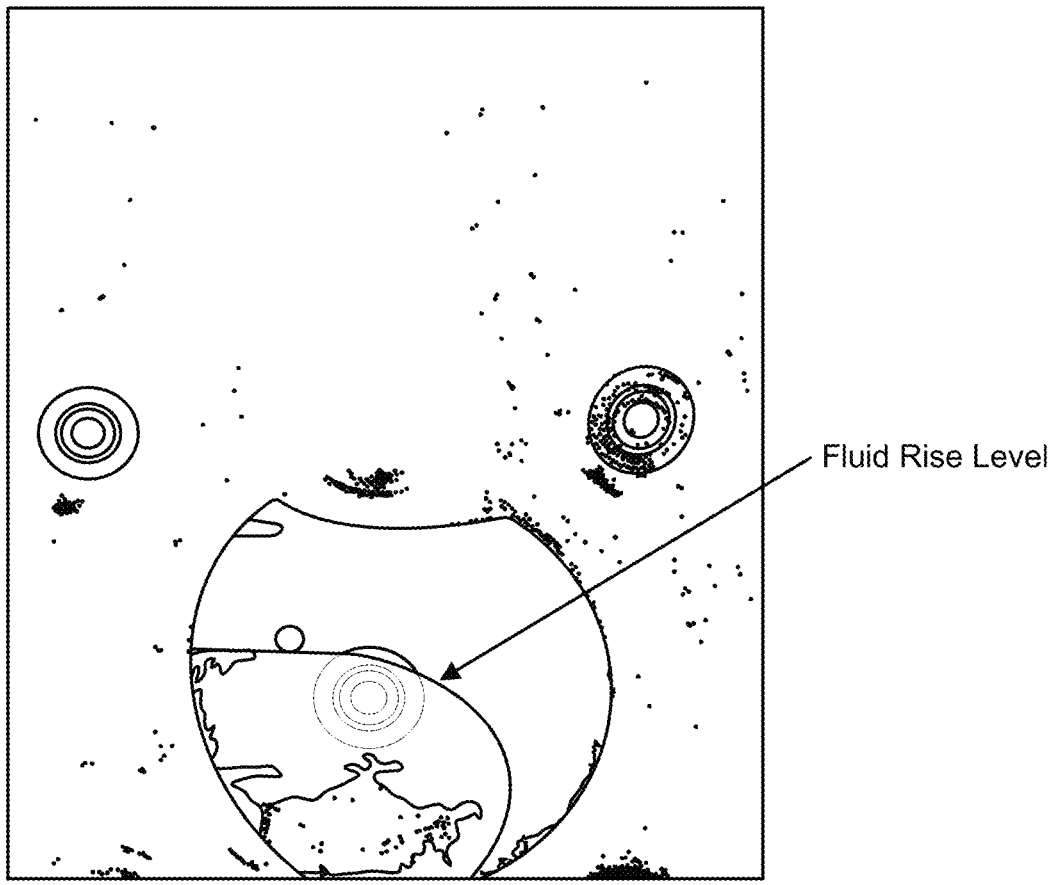
FIG. 52 shows fluid rise levels between puncture plate and ejector plate for an exemplary material.
Figure 53:
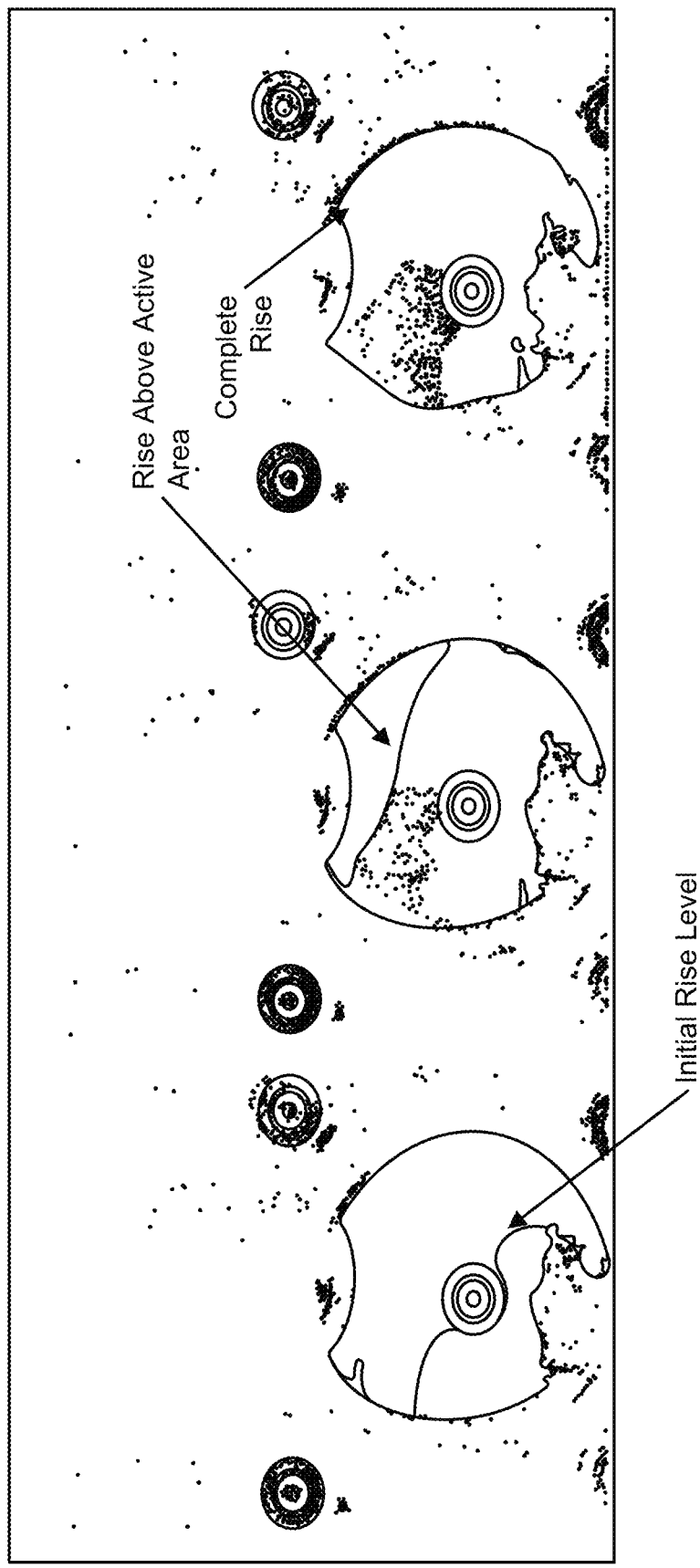
FIG. 53 shows fluid rise levels between puncture plate and ejector plate over time.

Alternatively, with reference to FIGS. 44-46, the puncture plate may be designed with an elongate needle puncture system. Such designs may, for instance, be used in connection with certain configurations of reservoir designs such as standing rectangular Low Tensile Stress (LTS) reservoirs (i.e., IV bag designs).

The puncture plate may be constructed from any suitable material, such as described and illustrated herein. By way of non-limiting example, the puncture plate may be constructed from: Liquid crystal polymer "LCP" (glass filled 0-30%); Nylon 6; Nylon 6,6; Polycarbonate; Polyetherimide (Ultem); Polyether ether ketone (PEEK); Kapton; Polyimide (Kapton); Stainless Steel 316L; Diamond-like carbon (DLC) coated Stainless Steel (300 series); Diamond-like carbon (DLC) coated aluminum; Diamond-like carbon (DLC) coated copper; Diamond-like carbon (DLC) coated nanocrystalline cobalt phosphate; Nano crystalline cobalt phosphate (nCoP); Gold coated Stainless Steel (300 series); Polymer coated (Polymers listed above) Stainless Steel (300 series); Polymer coated (Polymers listed above) Copper (300 series); Polymer coated (Polymers listed above) aluminum (300 series), etc.

Although the foregoing describes various embodiments by way of illustration and example, the skilled artisan will appreciate that various changes and modifications may be practiced within the spirit and scope of the present application. Even though the term "capillary plate" and "puncture plate" is used to describe various embodiments, it will be appreciated that the description is applicable to any fluid loading plate, need not take the form of a plate and can have any configuration suitable for channeling the liquid from the reservoir to the ejector mechanism.

As used herein, a reservoir may be any object suitable for holding a fluid. By way of example, the reservoir may be made of any suitable material capable of containing a fluid. Reservoirs of the present disclosure may be rigid or flexible and the reservoirs of the present disclosure may further be collapsible. As used herein, collapsible refers to a decrease in volume obtainable in a reservoir achieved by squeezing, folding, crushing, compressing, vacuuming, or other manipulation, such that total volume enclosed after collapsing is less than a volume that could be enclosed in a non-collapsed container. A reservoir may be made of any suitable material that can formed into a volume capable of holding a volume of fluid. Suitable materials, for example, may either be flexible or rigid and may be formable or pre-formed. As used herein a reservoir, by way of example, may be formed from a film.

Furthermore the reservoir may be in fluid communication with a fluid loading plate to form a fluid reservoir interface, and in certain embodiments the fluid loading plate may optionally include a reservoir mating surface or ring to facilitate connection with various fluid reservoir configurations.

In some aspects, the reservoir of the system of the disclosure may be configured as a low tensile stress or "LTS" reservoir. An LTS reservoir of the disclosure is generally designed to minimize or eliminate positive pressure gradients imposed on the system by the reservoir created from memory effects, crease formation, and unbiased collapse. Such gradients may result in a restoration of the reservoir (expansion in volume) that exerts a net pressure differential on the system, resulting in potential failure by drawing air into the system through the ejector openings. In certain aspects, to correct for the pressure differential, the LTS reservoir is configured so as to be biased to collapse into its low lying rest position, which reduces or eliminates the possibility of crease formation.

The LTS reservoir is also constructed from thin, flexible (low tensile stress) materials that resists volume expanding, rebounding, and memory effects without compromising the inertness and evaporation resistance (see Table 7). LTS reservoirs, as explained above and in further detail below, may be constructed in any suitable manner, e.g., including RF-welding, blow-fill seal processes, form-fill seal processing, etc.

Without intending to be limited by theory, to aid in fluid transport from the fluid retention/reservoir and through the capillary tubes during operation, the LTS reservoir may also be geometrically designed to accelerate the fluid by incorporating the principle of continuity and the Venturi effect as shown in FIG. 27 and as described below in the Bernoulli equation for incompressible flows, and shown in FIG. 28.

Again, without intending to be limited by theory, FIG. 28 describes how altering the reservoir geometry to a convergent shape profile (larger area to smaller area) results in the fluid accelerating as it moves down the reservoir due to the increase in velocity resulting from the continuity principle. According to the Bernoulli equation, an increase in velocity from the continuity principle will result in a decrease in pressure in the region of increased velocity (in order to maintain continuity). This change in pressure creates a gradient that aids in transporting the fluid into the fitment and through the puncture needles/capillary tubes. This increase in velocity resulting from a converging area change is known as the Venturi effect.

FIG. 29 illustrates how hydrostatic pressure drives fluid from the LTS ampoule into the fitment and through the puncture needles into the fluid reservoir. To maximize hydrostatic pressure the ampoule needs to be oriented in the upright position since hydrostatic pressure is a function of height.

TABLE 7

| Ampoule Type | Ampoule Material | Thicknesses |
| --- | --- | --- |
| RF-Welded | Polyurethane (PU), PU/Polyvinylidene Chloride (PVDC)/PU, Ethylene-Vinyl Acetate (EVA) Thermal Plastic Polyurethane (TPU) PU/Ethylene-Vinyl Alcohol (EVOH)/PU Isoplast ® ETPU | 2-12 mils |
| Blow fill seal | Low-Density Polyethylene (LDPE) LDPE w/ EVA (10%-50%) EVA (100%) | 2-15 mils |
| Form fill seal | Victrex (LDPE w/ oxygen barrier layer) TPU | 2-12 mils |

Figure 31:
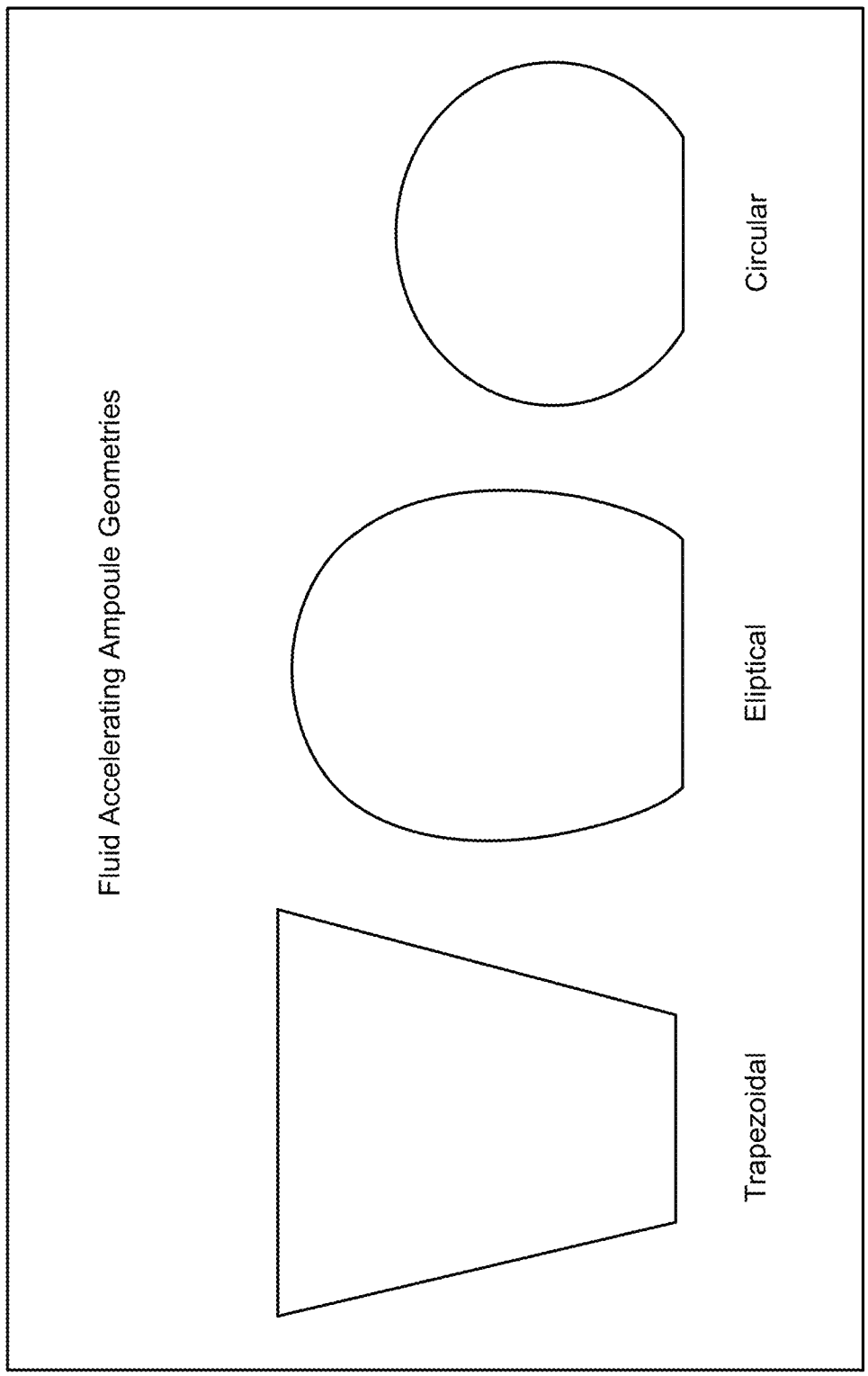
FIG. 31 shows schematic representations of further reservoir configurations of the disclosure.

FIG. 30 shows schematic representations of non-fluid accelerating LTS reservoir geometries, which collapse into themselves. The standing rectangle represents a reservoir (similar to an IV bag) that is designed to collapse along its minimum dimension (not shown). The standing rectangle reservoir design is oriented upright to maximize the height such that the effect of hydrostatic pressure is maximized. The second image shown is the lying rectangle which functions in a similar way to the standing rectangle, but without maximizing the effect of hydrostatic pressure. The third image shows a square reservoir configuration. FIG. 31 shows schematic representations of fluid accelerating LTS reservoir geometries.

With reference to FIG. 32, two examples of a circular fluid accelerating LTS reservoir are illustrated, one constructed by blow-fill-seal processes (FIG. 32A) and the other by RF-welding (FIG. 32B). As shown, the amount of collapse may be enhanced when the reservoir is biased to collapse along the minimum dimension, which in FIG. 32 is the thickness. This type of collapse largely prevents the formation of creases in the reservoir during operation. For standing reservoir designs, further protection against crease formation during operation of an ejector device may be created by enclosing the reservoir in a housing that prevents it from folding over itself as it is emptying. Supporting data of the performance of these reservoirs is provided herein.

Figure 33:
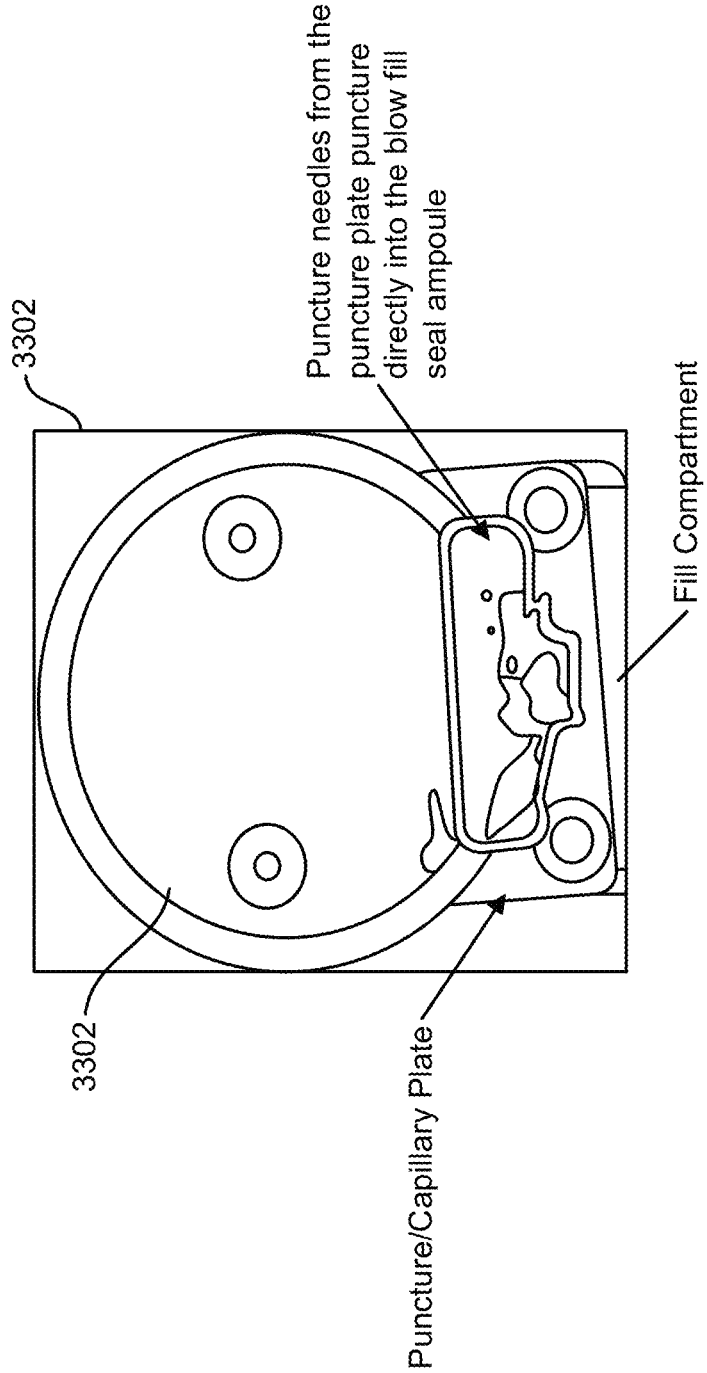
FIG. 33 shows a back view of one embodiment of a blow-fill-seal reservoir and puncture plate of the disclosure.

FIG. 33 shows a configuration of a puncture plate 3300 and a blow-fill-seal reservoir with the fitment removed. In certain embodiments, where for self-sealing reservoir materials are used, the puncture can occur directly through the lower region of the reservoir. The fill compartment shown at the bottom of FIG. 33 is designed to allow for maximal fluid fill of the secondary reservoir. Alternative puncture mechanisms for the blow fill seal puncture plate assembly are shown in FIG. 34.

Figure 34B:
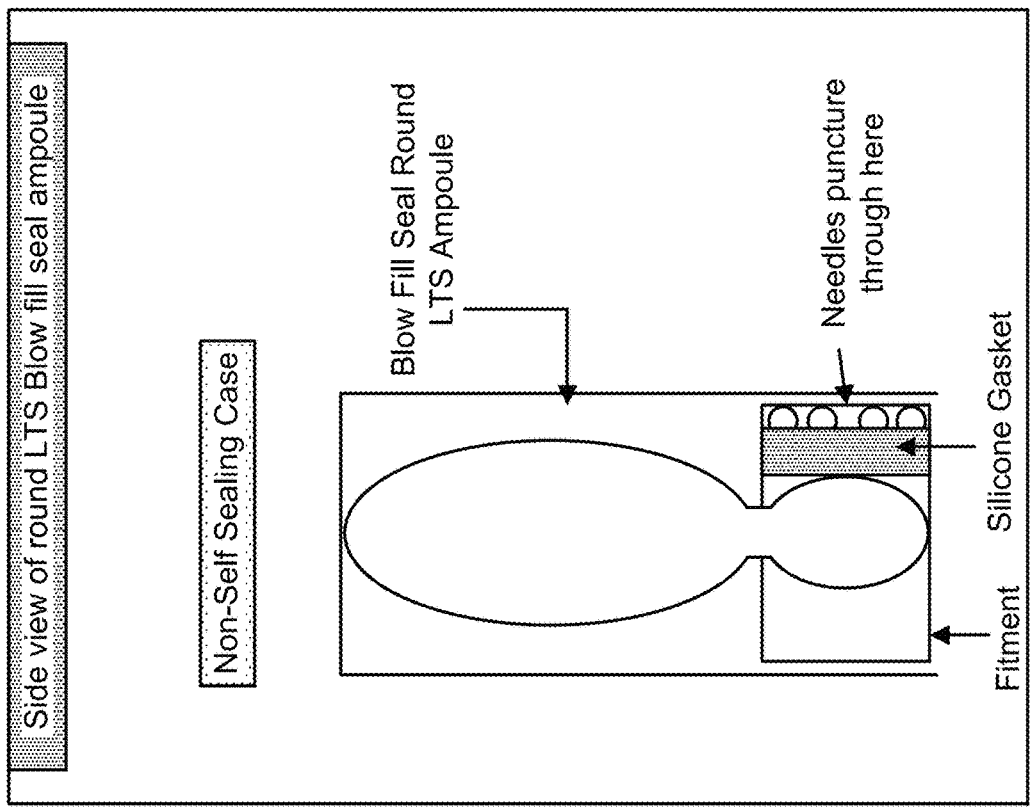
FIGS. 34A-34B show side views of two blow-fill-seal reservoir and puncture plate system embodiments of the disclosure.
Figure 34A:
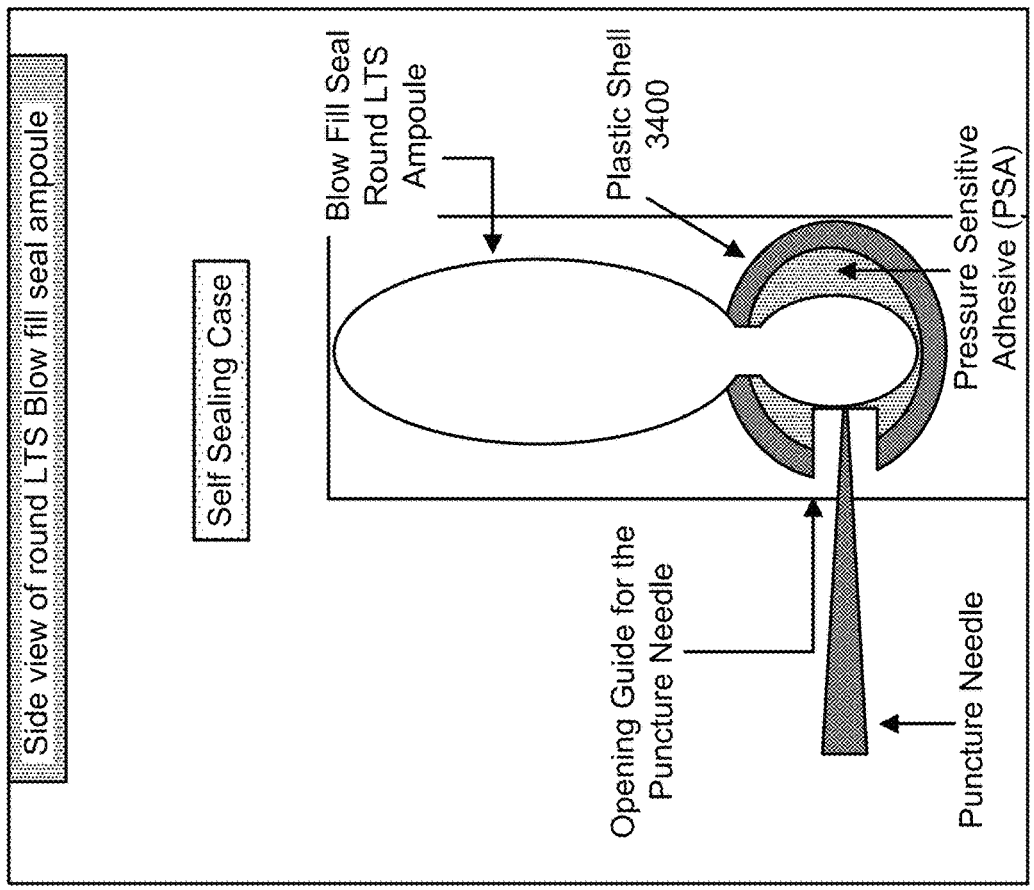

FIG. 34A shows a side profile of another embodiment of the blow fill seal reservoir puncture plate assembly. FIG. 34A shows a stiffening mechanism in the form of a plastic shell 3400 used to aid in needle puncture through the blow fill reservoir when it is constructed from a self-sealing material. The figure to the right (FIG. 34B) shows the configuration when the blow fill seal reservoir does not self-seal upon puncture and must be connected to the fitment in the same manner as in FIGS. 22 and 23. As is shown in FIG. 34B, the needles need to pass through the silicon gasket into the region shown as "Needles puncture through here".

Figure 35:
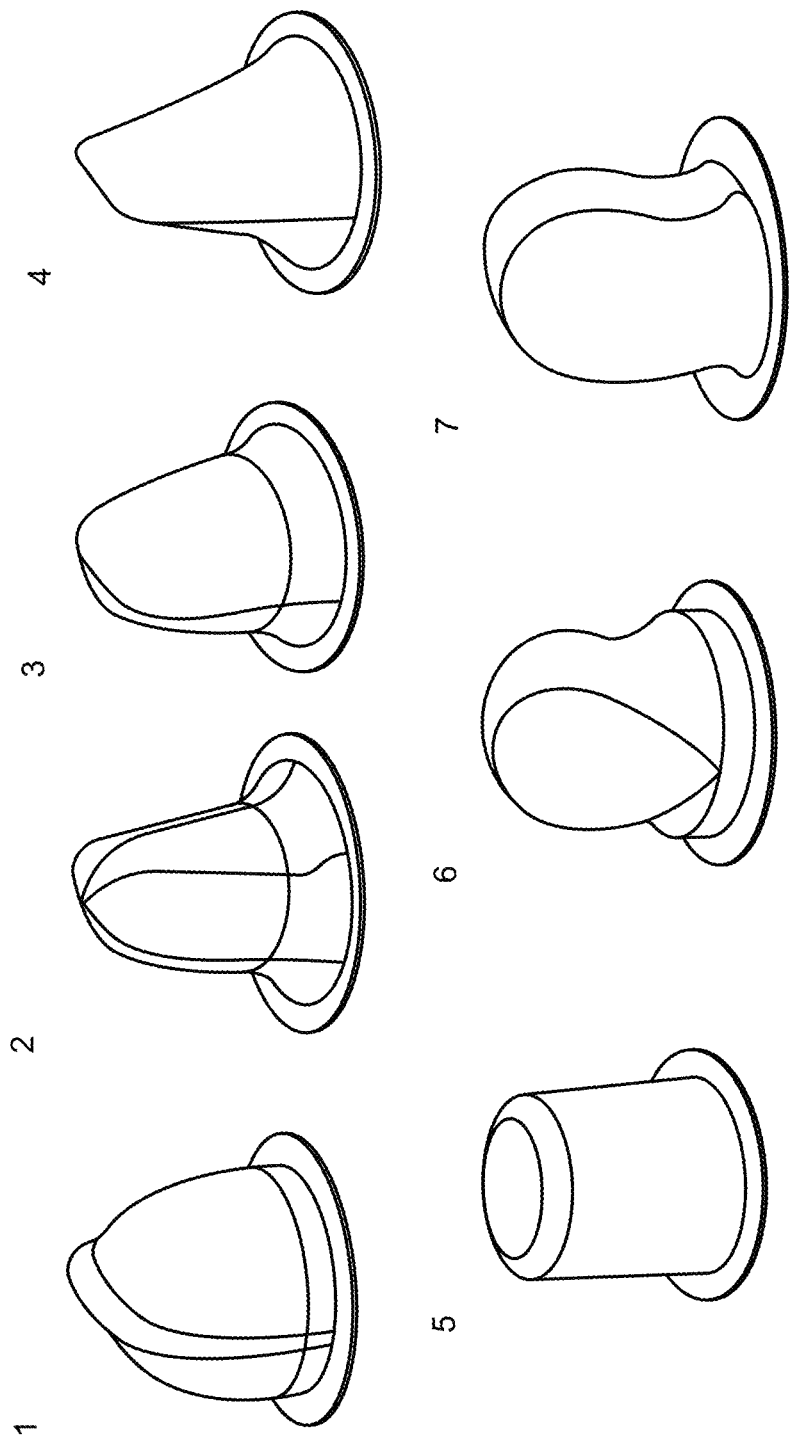
FIG. 35 shows different form-fill-seal reservoir embodiments of the disclosure.

In yet other embodiments of the disclosure, FIG. 35 illustrates geometries of reservoirs that are biased to collapse a certain way to prevent crease formation. Spray down and pull down procedures and results for these ampoules are disclosed in the example below.

Example 3: Measurement of Spray Down and Pull Down

Figure 36:
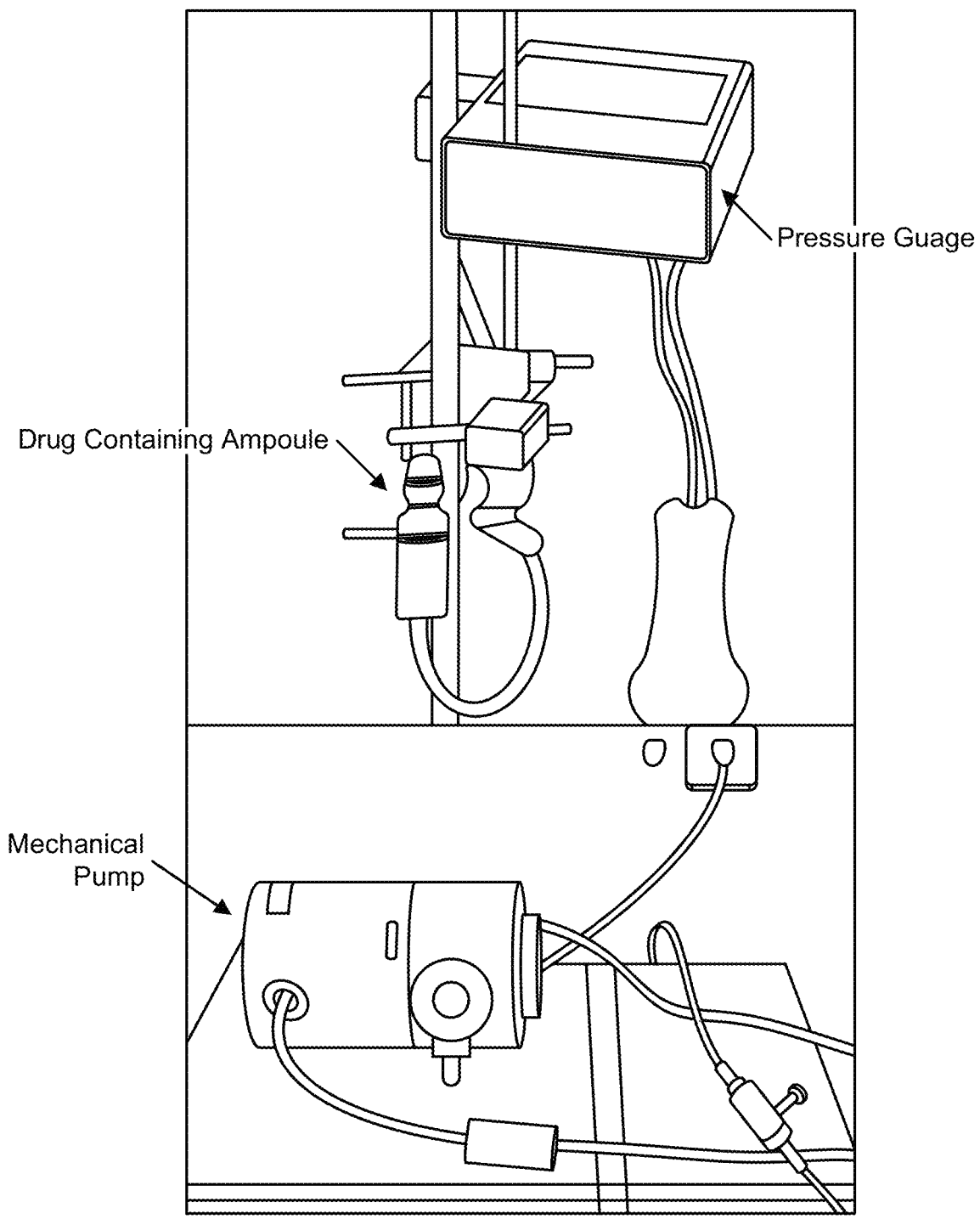
FIG. 36 shows aspects of an apparatus and set-up to determine the amount of negative pressure that different reservoir configurations exert as they are removing fluid.
Figure 37:
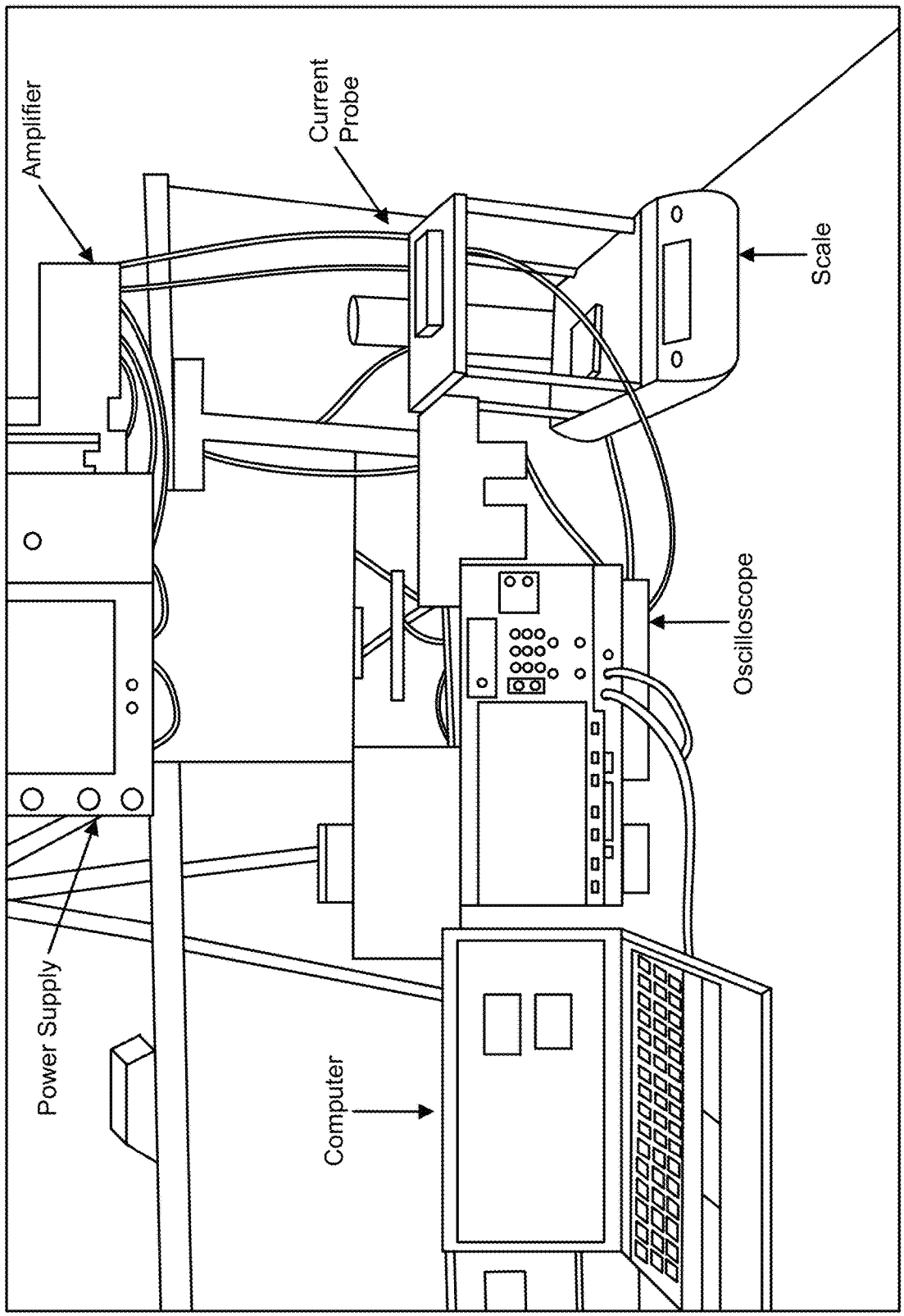
FIG. 37 shows additional aspects of an apparatus and set-up to determine the amount of negative pressure that different reservoir configurations exert as they are removing fluid.

Static pull down tests were performed to determine the amount of negative pressure that different reservoir configurations, e.g., as shown in FIGS. 30-35, exert on the system as they are removing fluid. The experimental setup for this test is shown in FIGS. 36-37. The experimental procedure is as follows: a reservoir is attached to a water column tube that is connected to a vacuum regulator connected to a mechanical pump used to draw fluid from the reservoir or ampoule.

Mass deposition testing was performed to determine the mass of a spray from a device at a given frequency or multiple frequencies (mass deposition sweep). Given that some frequencies have a very low mass per spray, which may be at the lower tolerance of the scale used for measuring the mass, the number of sprays were varied per sample at each frequency, then averaged to determine a per spray volume at each frequency. This also helped eliminate some error in the measurement. (The scale used could read to the tenth of a milligram.) These setups were run by a laptop computer, which communicated with the scale, a function generator, and an oscilloscope. The mass of the sprays was recorded as well as the electrical characteristics (phase and magnitude of the voltage and the current, and the impedance) during the spray. The setup was controlled by a labview program that was compiled into a labview executable program and run from the laptop. This program allowed the user to select the lab equipment in the setup, the com port for the scale, and Universal Serial Bus (USB) identification for the oscilloscope and function generator. The user also defined the testing parameters: voltage, wave form, start frequency, end frequency, step size, number of sprays, time between sprays, and spray duration. The program communicated with function generator, setting the frequency for the spray and the number of cycles to achieve the appropriate spray duration, and set the oscilloscope to single acquisition from a trigger (Voltage Probe). The program then instructed the function generator to trigger the wave form. The signal was sent to an operational amplifier to boost the signal to the appropriate voltage, which was then applied to the device (0 to ±90V). At the device, voltage and current probes were attached to verify the voltage and to read the current. A delay was written into the program to allow time for the scale to balance out (≈8 sec) before reading the mass from the scale and determine the mass per spray. The scale was zeroed at the start of the test and at every half gram. At every half gram when zeroing the scale, the scale was cleaned and the reservoir attached to the device was refilled. This insured that the device did not run out of fluid, and lowered the error from evaporation of the fluid on the scale by limiting the amount of fluid on the scale that could evaporate to 0.5 g. The scale was read after each set of sprays as defined by the user (normally 5). The mass of the sprays was determined by subtracting the previous value from the current scale reading, thereby eliminating the time required to zero the scale between sets of sprays.

Figure 38:
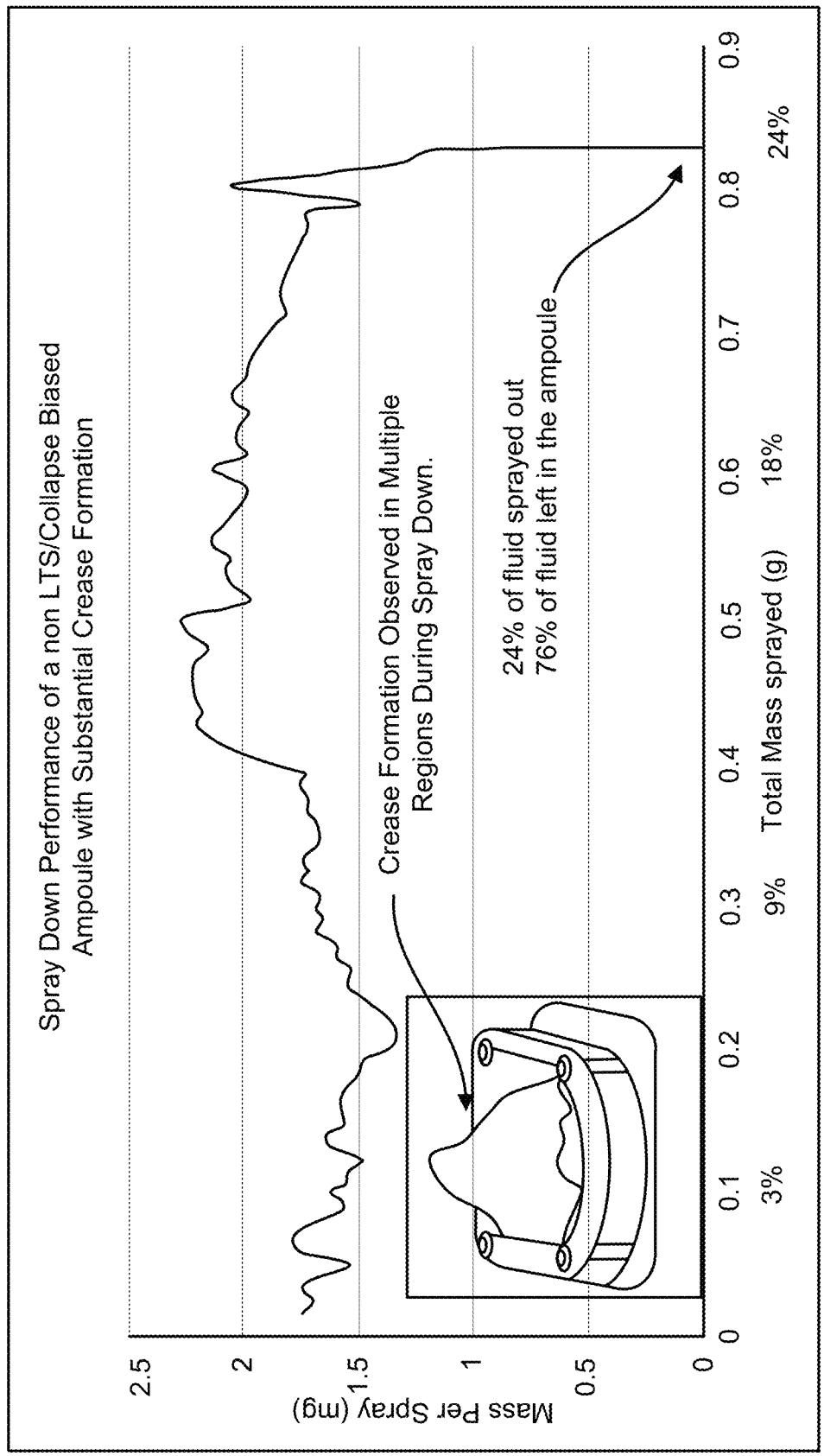
FIG. 38 shows the mass per spray and total spray (spray down performance) of a non-collapse biased reservoir embodiment with substantial crease formation of the disclosure.
Figure 39:
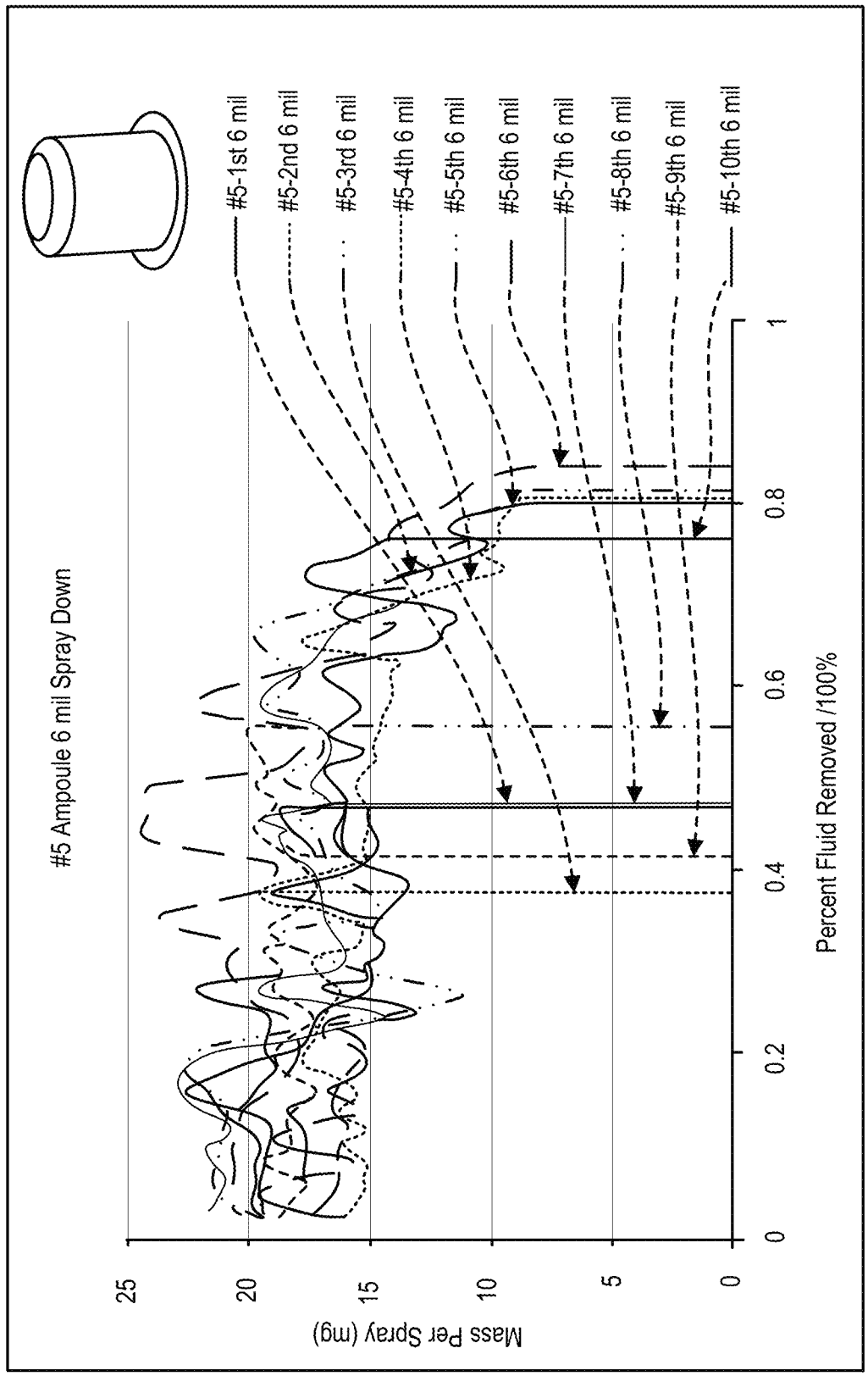
FIG. 39 shows the mass per spray and total spray (spray down performance) of various blow-fill-seal reservoir embodiments of the disclosure.

FIG. 38 shows spray down performance (24% of the fluid) of a control reservoir that is fairly rigid and collapses to form many creases that result in a buildup of negative pressure. FIG. 39 shows the results for a representative LTS reservoir of the disclosure, as illustrated in FIG. 35. This shows an improvement in spray down performance when creating a geometry biased to collapse in a controlled direction as well as choosing flexible materials and the appropriate material thickness. The graph shows that the majority of the samples (multiple tests of the same ampoule type with the same thicknesses) allowed 80 percent or more of the fluid to be removed, with a few outliers, which removed much less but better than the creased, control reservoir of FIG. 38.

Figure 40:
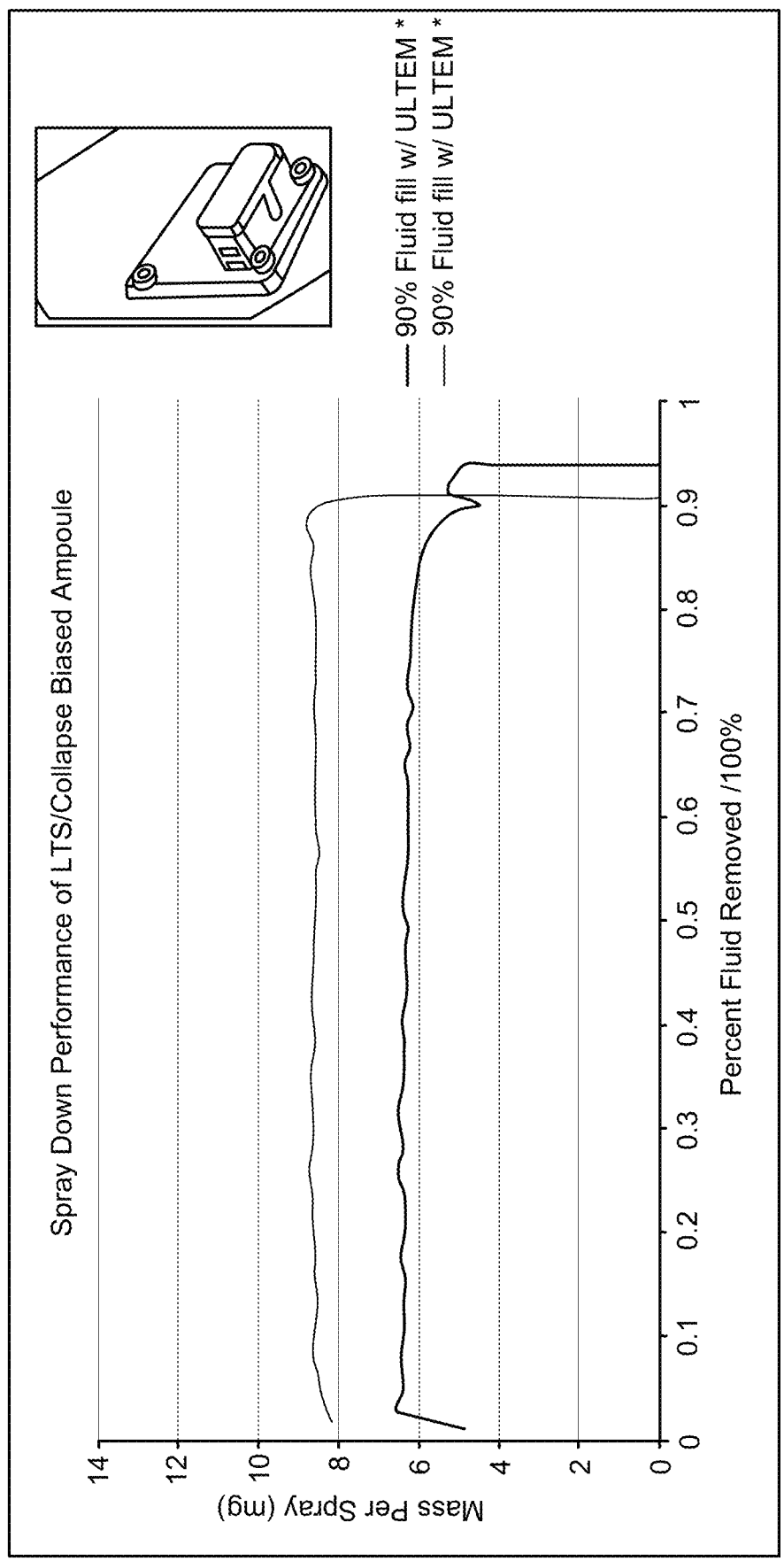
FIG. 40 shows two runs of a mass per spray and total spray (spray down performance) of an LTS/collapse-biased self-sealing RW weld reservoir embodiment of the disclosure.
Figure 43:
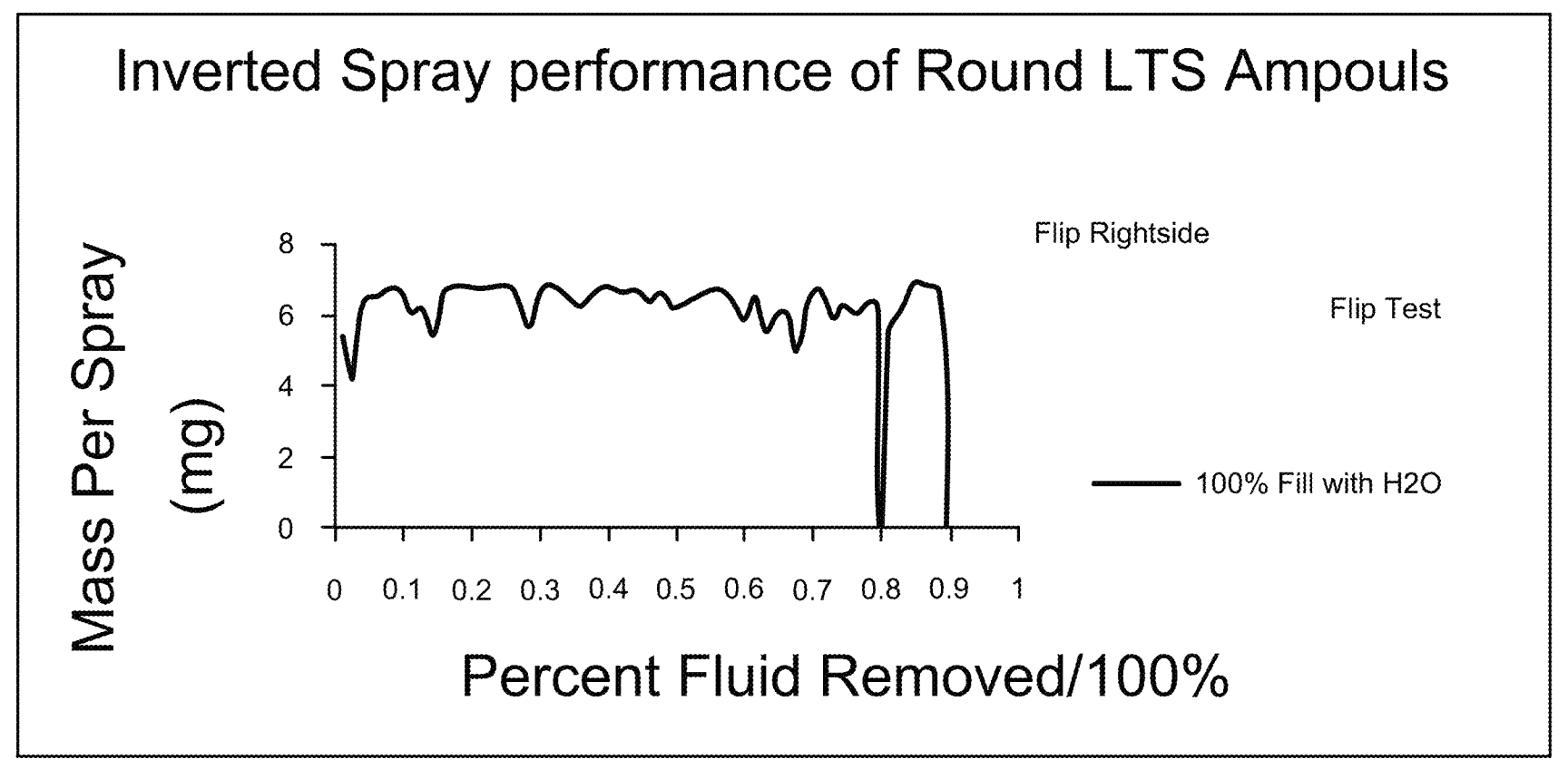

FIG. 40 shows the spray down performance of two separate runs with one embodiment of a round LTS reservoir. This reservoir showed a marked improvement, with over 90 percent of the fluid removed. FIG. 41 shows the pull downs for select round LTS ampoule designs from FIG. 35. These graphs show a large improvement in the negative pressure generated from the system when using the round LTS reservoir. Without intending to be limited by theory, FIG. 42 shows the mechanism involved in inverted spray using a round LTS reservoir, while FIG. 43 shows the actual spray down performance results of an LTS reservoir sprayed down in a complete puncture system upside down.

In accordance with other aspects of the disclosure, the fluid loading plate may be designed with a different needle puncture systems, as illustrated in FIGS. 44-46. Such designs may be used in connection with reservoir designs, e.g., standing rectangular LTS reservoirs (i.e., IV bag style designs).

As discussed above, an ejector plate of the system may include capillary rise holes to provide additional air pressure relief above the active area (ejector openings). This additional air pressure relief may thereby allow for complete capillary rise of the fluid, which allows the retention/reservoir to be completely filled with fluid. In accordance with certain aspects of the invention, it was unexpectedly found that if these holes are not placed above the ejector openings, the device may not operate efficiently once the fluid falls below the level of the ejector openings (thereby potentially allowing outside air to move into the system during operation).

When constructing capillary rise holes, optimization of hole size is of importance. The holes are preferably large enough to allow a reasonable venting rate so that the capillary rise is not too slow, and are preferably small enough so that the fluid does not readily leak when the hole is aligned in the direction of gravity. Leaking of the fluid out of the rise hole is a function of the size of the hole as well as the surface tension of the fluid. Fluids with higher surface tensions have increased resistance to leaking due to the strength of the fluid meniscus (which is a function of the surface tension of the fluid) formed within the rise hole by the fluid, which creates a barrier from fluid leaking out and air moving in. The barrier is breached when the hydrostatic pressure of the reservoir (ampoule) overcomes the surface tension within the rise hole cavity (see FIG. 47).

The fluid loading plate of the disclosure utilizes capillary action to transport fluid to a location behind the active area of the piezoelectric mesh for ejection, e.g., as discussed earlier with respect to FIG. 27. Capillary rise is a function of the surface tension of the fluid, surface energy of the surfaces in contact with the fluid (contact angle), and the separation distance of the surfaces in contact with the fluid. To achieve optimal performance for the puncture plate system a hydrophilic material (contact angle between the fluid and the surface less than 90 degrees) is preferably used for the capillary channels. In addition the material is preferably biocompatible and chemically inert. The separation distance of the surfaces containing the fluid rise are preferably tuned to ensure that the capillary width is considerably less than the capillary length of the fluid thereby ensuring that the surface forces are more significant than that of gravity. As shown in FIG. 27, capillary rise in the system occurs between the puncture plate (capillary plate+needles) and the ejector plate (which includes the active area or openings (piezoelectric mesh screen).

Example 4: Measurement of Capillary Rise

FIGS. 48-49 illustrate capillary pressure for various sized half droplets of water and an exemplary ocular medication, latanaprost. Thus, the fluid loading plate separation distance from the ejector plate is an important parameter for optimization of capillary rise to a certain height above the ejector openings. This plate separation distance (along with viscosity and surface tension of the fluid) also impacts the time for the fluid to rise to the final height. As shown in FIG. 50, a device designed to spray water and saline can operate with a capillary distance less than or equal to 2.7 mm. However, the systems of the disclosure are not so limited, and a capillary distance (separation between capillary plate and the ejector plate) from 2.7 mm-1.7 mm, and below 1.7 mm may be utilized to achieve greater capillary rise. In certain embodiments, a distance for the puncture plate system may be between 50-200 micrometers.

In this regard, FIG. 51 shows capillary rise for saline in capillary channels made of different materials. FIG. 52 shows capillary rise between capillary plate and puncture plate without a capillary rise hole 2302. This is contrasted with the much better capillary rise shown in FIG. 53, which shows the rise when a capillary rise hole is included.

Further, Tables 8-10 below show capillary rise data in the capillary channel between the fluid loading plate and the rear surface of the ejector mechanism as a result of using different numbers and sizes of capillary rise holes 2302. Table 8 shows the data for rise time for water, Table 9 shows rise time for Latanaprost at room temperature, and Table 10 shows the rise time for Latanaprost refrigerated to 38° F. Some results had to be discarded as in operative (In-Op, No Fill Past Active Area, blank entry) due to defects in the capillary rise holes, or showed asymmetric fill (marked with an asterisk), but the results indicated the benefits in rise time when using 5 capillary holes, and showed faster rise times with increase capillary hole size.

TABLE 8

| | | 1 Hole | 3 Holes | 5 Holes |
|---|---|---|---|---|
| 5 um | Test 1 | 395 s | 200 s | In-Op |
| | Test 2 | 370 s | 155 s* | In-Op |
| 10 um | Test 1 | No Fill Past Active Area | 70 s | 23 s |
| | Test 2 | No Fill Past Active Area | 54 s | 25 s |
| 20 um | Test 1 | 22 s | 8 s | 6 s |
| | Test 2 | 22 s | 10 s | 5.5 s |
| 5 um | Test 1 | 3 s | 2 s | In-Op |
| | Test 2 | 3.5 s | 1.6 s | In-Op |

TABLE 9

|        |        | 1 Hole              | 3 Holes | 5 Holes |
|--------|--------|---------------------|---------|---------|
| 10 um  | Test 1 | No Fill past A.A.   | 60 s    | 26 s    |
|        | Test 2 |                     | 68 s*   | 32 s    |
| 20 um  | Test 1 | 11 s                | 8 s     | 6 s     |
|        | Test 2 | 8 s                 | 11 s    | 5 s     |

TABLE 10

|        |        | 1 Hole | 3 Holes | 5 Holes |
|--------|--------|--------|---------|---------|
| 10 um  | Test 1 |        | 25 s    | 28 s*   |
|        | Test 2 |        | 42 s    | 44 s*   |
| 20 um  | Test 1 | 7 s    | 10 s    | 3.5 s   |
|        | Test 2 | 10 s   | 7 s     | 4.5 s   |

Example 5: Fluid Leak Testing for Select Ocular Drugs and Rise Hole Sizes

Figure 54:
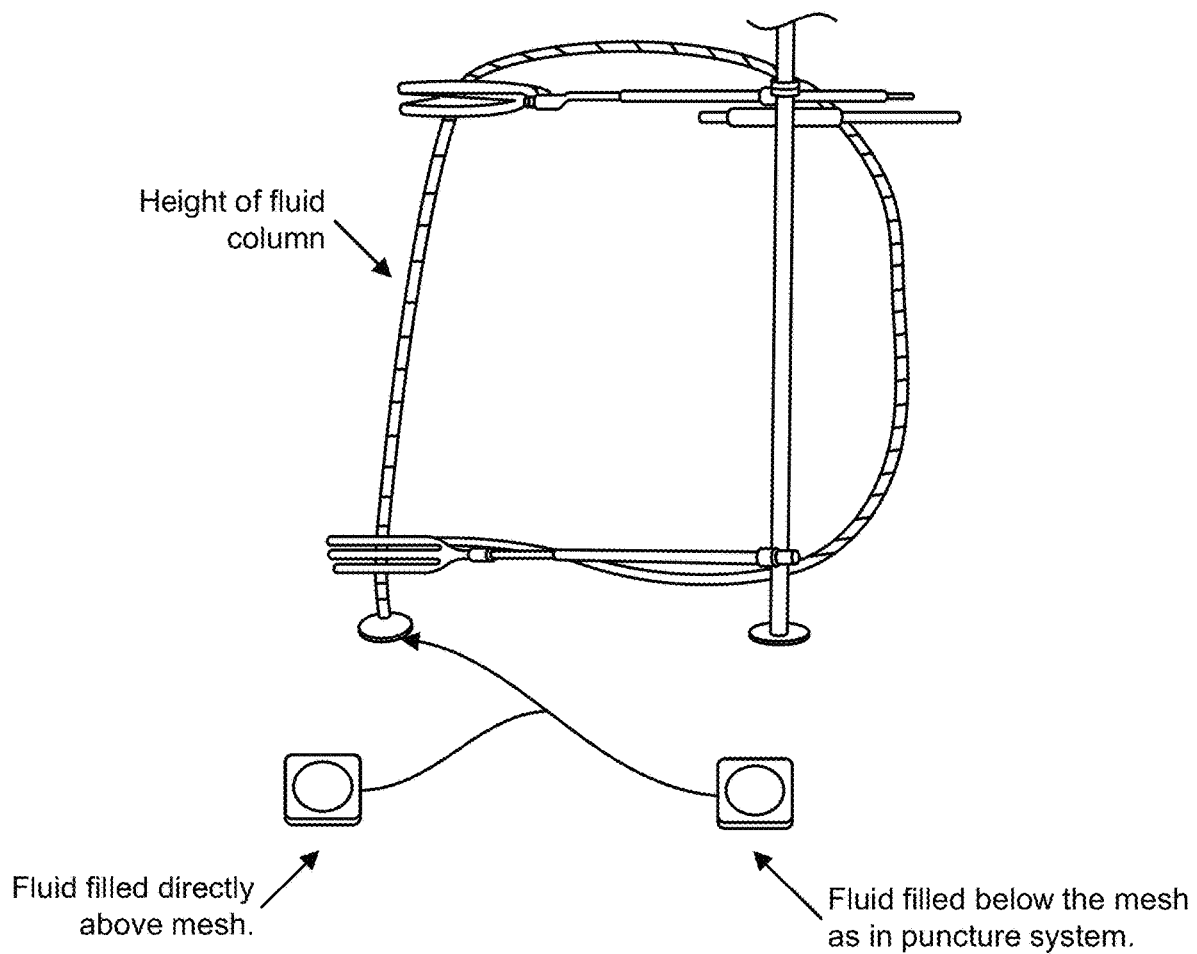
FIG. 54 shows a test set-up to test for fluid leaking out of capillary rise hole under different fluid fill locations.

To test for fluid leaking out of capillary rise holes or vent holes of one embodiment of the device, a hydrostatic pressure test assembly was constructed as shown in FIG. 54. The ejector plate with the rise holes and the ejector assembly was placed beneath the fluid column defined by the tube. The test fluid was filled into the tube oriented directly above the ejector plate with the height of the fluid column carefully monitored. When the fluid reached test heights (hydrostatic pressure) at which the fluid above the ejector openings caused leakage through the rise holes and the ejector openings, the heights (corresponding to the pressure values) were recorded and used as a design parameter for optimizing rise hole dimensions. Results are shown in Tables 5-7 below.

TABLE 11

|                     |                     | Water column to side of mesh | | | | Water column directly above mesh | | | |
|---|---|---|---|---|---|---|---|---|---|
|                     |                     | Vent Holes (inches water) | | Mesh Holes (inches water) | | Vent Holes (inches water) | | Mesh Holes (inches water) | |
| Annulus Vent Hole   | Mounting Condition  | Average | Standard Deviation | Average | Standard Deviation | Average | Standard Deviation | Average | Standard Deviation |
| 1 × 5 um            | 1                   | 32      |                    | 31      | 2                  | 22      | 3                  | 29      | 4                  |
|                     | 2                   | 28      | 3                  | 31      |                    | 23      | 3                  | 31      |                    |
| 3 × 5 um            | 1                   | 28      |                    | 27      | 2                  |         |                    |         |                    |
|                     | 2                   | 26      | 3                  | 29      | 3                  |         |                    |         |                    |
| 5 × 5 um            | 1                   |         |                    |         |                    | No leak |                    | 27      | 6                  |
|                     | 2                   |         |                    |         |                    | No leak |                    | 28      | 6                  |
| 1 × 10 um           | 1                   | 23      | 10                 | 27      | 3                  | 15      | 1                  | 25      | 4                  |
|                     | 2                   | 22      | 4                  | 27      | 2                  | 18      | 2                  | 23      | 5                  |
| 3 × 10 um           | 1                   | 15      | 1                  | 25      | 4                  |         |                    |         |                    |
|                     | 2                   | 14      | 2                  | 26      | 5                  | 13      | 3                  | 23      | 5                  |
| 3 × 20 um           | 1                   |         |                    |         |                    |         |                    |         |                    |
|                     | 2                   | 22      | 2                  | 23      | 5                  |         |                    |         |                    |
| 1 × 50 um           | 1                   |         |                    |         |                    |         |                    |         |                    |
|                     | 2                   |         |                    |         |                    | 12      | 4                  | No leak |                    |
| 3 × 50 um           | 1                   |         |                    |         |                    |         |                    |         |                    |
|                     | 2                   |         |                    |         |                    | 14      | 3                  | No leak |                    |
| 5 × 50 um           | 1                   |         |                    |         |                    |         |                    |         |                    |
|                     | 2                   |         |                    |         |                    | 13      | 4                  | No leak |                    |

TABLE 12

|                     |                     | Tropicamide column to side of mesh | | | | Tropicamide column directly above mesh | | | |
|---|---|---|---|---|---|---|---|---|---|
|                     |                     | Vent Holes (inches Tropicamide) | | Mesh Holes (inches Tropicamide) | | Vent Holes (inches Tropicamide) | | Mesh Holes (inches Tropicamide) | |
| Annulus Vent Hole   | Mounting Condition  | Average | Standard Deviation | Average | Standard Deviation | Average | Standard Deviation | Average | Standard Deviation |
| 1 × 5 um            | 1                   |         |                    |         |                    |         |                    |         |                    |
|                     | 2                   | 7       | 1.5                | 6.8     | 1                  |         |                    |         |                    |
| 1 × 10 um           | 1                   |         |                    |         |                    |         |                    |         |                    |
|                     | 2                   | 4.8     | 0.9                | 6       | 0.7                | 7       |                    | 5.6     | 1.2                |
| 3 × 10 um           | 1                   |         |                    |         |                    |         |                    |         |                    |
|                     | 2                   | n/a     |                    | 6.3     | 1.3                | n/a     |                    | 4.8     | 0.5                |
| 3 × 20 um           | 1                   |         |                    |         |                    |         |                    |         |                    |
|                     | 2                   | n/a     |                    | 8.1     | 1.6                | n/a     |                    | 3.8     | 0.8                |
| 1 × 50 um           | 1                   |         |                    |         |                    |         |                    |         |                    |
|                     | 2                   | 4       | 0.9                | 6       | 1.3                |         |                    |         |                    |
| 3 × 50 um           | 1                   |         |                    |         |                    |         |                    |         |                    |
|                     | 2                   | 4.8     | 0.7                | 6.4     | 0.8                |         |                    |         |                    |

TABLE 13

| | | Latanoprost column to side of mesh | | | |
|---|---|---|---|---|---|
| | | Vent Holes (inches Latanoprost) | | Mesh Holes (inches Latanoprost) | |
| Annulus Vent Hole | Mounting Condition | Average | Standard Deviation | Average | Standard Deviation |
| 1 × 5 um | 1 | | | | |
| | 2 | n/a | | 3.7 | 0.6 |
| 1 × 10 um | 1 | | | | |
| | 2 | n/a | | 3.5 | 0.6 |
| 1 × 50 um | 1 | | | | |
| | 2 | 3.3 | 0.7 | 3.7 | 0.6 |

Although the foregoing describes various embodiments by way of illustration and example, the skilled artisan will appreciate that various changes and modifications may be practiced within the spirit and scope of the present application.

As mentioned above, droplets may be formed by an ejector mechanism from fluid contained in a reservoir that is coupled to the ejector mechanism. The ejector mechanism and reservoir, which together form an ejector assembly, may be configured to be removable to allow the assembly to be disposed of or reused. Thus the components may be packaged in a housing, e.g., the upper section 200 of the housing 202 shown in FIG. 2, in a removable manner. The housing itself may therefore be disposable, or may be reusable by being configured to receive a removable ejector mechanism. The housing may be handheld, miniaturized, or formed to couple to a base, and may be adapted for communication with other devices. Housings may be color-coded or configured for easy identification.

While specific embodiments of the ejector mechanism are discussed below, this does not limit the configuration or use of the ejector mechanism nor the features that may be added to the ejector device. Ejector devices, in some implementations, may include illumination means, alignment means, temperature control means, diagnostic means, or other features. Other implementations may be part of a larger network of interconnected and interacting devices used for subject care and treatment. The ejector mechanism may, for example, be a piezoelectric actuator as described herein.

Referring to FIGS. 55 A-C, an ejector assembly 5500 may include an ejector mechanism 5501 and a reservoir 5520. The ejector mechanism 5501 may include an ejector plate 5502 coupled to a generator plate 5532 that includes one or more openings or holes 5526. The ejector plate 5502 and generator plate 5532 that can be activated by a piezoelectric actuator 5504 which vibrates to deliver a fluid 5510, contained in the reservoir 5520, in the form of ejected droplets 5512 along a direction 5514. Again, the fluid may be an ophthalmic fluid that is ejected towards an eye 5516 of a human adult, child, or animal. Additionally, the fluid may contain an active pharmaceutical to treat a discomfort, condition, or disease of a human or an animal. In some implementations, the generator plate is a high modulus polymer generator plate, e.g., formed from a material selected from the group consisting of: ultrahigh molecular weight polyethylene (UHMWPE), polyimide, polyether ether ketone (PEEK), polyvinylidene fluoride (PVDF), and polyetherimide. comprises a high modulus polymeric generator plate.

As shown in FIG. 55A, ejector plate 5502 is disposed over the front of the reservoir 5520 which contains fluid 5510. The rear surface 5525 of ejector plate 5502 is arranged to be adjacent to the fluid 5510. In this embodiment, the reservoir 5520 therefore has an open end 5538 which is attached adjacent to surface 5525 and to openings 5526. In this embodiment, surface 5525 encloses the fluid 5510 in the reservoir 5520. The reservoir 5520 may be coupled to the ejector plate 5502 at a peripheral region 5546 of the surface 5525 of the ejector plate 5502 using a suitable seal or coupling. By way of example, the reservoir 5520 may be coupled via an O-ring 5548a. Although not shown, more than one O-ring can be used. As known in the art, the O-rings may have any suitable cross-sectional shape. Furthermore, other couplers such as polymeric, ceramic, or metallic seals can be used. Alternatively, the coupling can be eliminated altogether and reservoir 5520 may be integrally connected to ejector plate 5502, for example by welding or over molding. In such an implementation, an opening through which fluid is supplied to reservoir 5520 may be provided (not shown). In embodiments where couplings are used, the couplings may be made removable, e.g., by providing a hinged connection between the reservoir 5520 and the ejector plate 5502, or by providing a flexible or non-rigid connector, e.g., polymeric connector.

The reservoir 5520 may define a peripheral lip or wall 5550 covering portions of the ejector plate 5502. In the implementation of FIG. 55A, the wall 5550 does not directly contact the ejector plate 5502, rather it is coupled to O-rings 5548a. Alternatively, the wall 5550 can be directly attached to ejector plate 5502. Instead, the reservoir can be directly attached to the ejector plate 5502 and the wall 5550 can be omitted altogether.

The configuration of the reservoir, including the shape and dimension, can be selected based on the amount of fluid 5510 to be stored, as well as the geometry of the ejector plate 5502. Alternative forms of reservoirs include gravity-fed, wicking, or collapsible bladders (as discussed above and which accommodate pressure differentials). These reservoirs may be prefilled, filled using a micro-pump or may be configured to receive a replaceable cartridge. The micro pump may fill the reservoir by pumping fluid into or out of a collapsible or non-collapsible container. The cartridge may include a container which is loaded into the reservoir. Alternatively, the cartridge itself may be coupled to a disposable ejector assembly which is then replaced after a specified number of discharges. Examples of reservoirs are illustrated in U.S. patent application Ser. No. 13/184,484, filed Jul. 15, 2011, the contents of which are herein incorporated by reference.

In some implementations, the reservoir 5520 includes through holes 5542 (only one shown in FIG. 55A) to allow air to escape from or enter the reservoir 5520 and keep the fluid 5510 in the reservoir at the appropriate ambient pressure. The through holes 5542 have a small diameter so that the fluid 5510 does not leak from the holes. Alternatively, no openings may be formed in the reservoir 5520, and at least a portion, e.g., the portion 5544, or the entire reservoir 5520 can be collapsible, e.g., in the form of a bladder, as is discussed in greater detail above. Thus the entire reservoir may, in some embodiments, be made in the form of a flexible or collapsible bladder. Accordingly, as the fluid 5510 is ejected through the openings 5526, the reservoir 5520 changes its shape and volume to follow the changes in the amount of fluid 5510 in the reservoir 5520.

In the embodiment of FIG. 55A, the ejector mechanism 5501 is activated by being vibrated by a piezoelectric actuator 5504, which in this embodiment has an annular shape. Two electrodes 5506a and 5506b are formed on two opposite surfaces 5536 and 5534 of the piezoelectric actuator 5504 that are parallel to the surface 5522 of the ejector plate 5502 and activate the piezoelectric actuator 5504 to vibrate the ejector plate 5502 and a generator plate 5532. For ease of representation the ejector plate 5502 and generator plate 5532 are shown lying in a common plane. However, as is discussed in greater detail below with respect to FIGS. 1B-1D, the generator plate 5532 in this embodiment is attached to a surface of the ejector plate 5502. The electrodes 5506a and 5506b can be attached to the ejector plate or piezoelectric actuator in any known manner including fixing by adhesive or otherwise bonding. They may also be overmolded in place to ejector plate 5502. Wires or other conductive connectors can be used to affect necessary electrical contact between the ejector plate 5502 and the electrodes 5506a and 5506b. Alternatively, the electrodes may be formed on the ejector plate 5502 by plating or otherwise depositing. By way of example, the electrodes are attached by means of electrically conductive adhesive 5528 which is applied between the electrode 5506a and the ejector plate 5502 to place the electrode 5506a in electrical contact with the ejector plate 5502. When a voltage is applied across the electrodes 5506a and 5506b, the piezoelectric actuator 5504 deflects ejector plate 5502 and likewise generator plate 5532 to change the shape to a more concave or convex shape.

Accordingly, when a voltage is applied across the electrodes 5506a and 5506b, the piezoelectric actuator 5504 deflects ejector plate 5502 and likewise generator plate 5532 to change shape to be alternately more concave or convex at the resonance frequency of the coupled ejector plate 5502 and generator plate 5532. The coupled ejector plate 5502 and generator plate 5532 deflected by the piezoelectric actuator 5504 at the resonant frequency may amplify the displacement of the coupled ejector plate 5502 and generator plate 5532 thereby decreasing the power requirements of the piezoelectric actuator input. In a further aspect, the damping factor of the resonance system of the coupled ejector plate 5502 and generator plate 5532 due to the inherent internal resistance of the annulus/mesh limits the movement to prevent a runaway condition and prevent catastrophic failure.

An extensive range of voltages corresponding to different piezoelectric materials are known in the art, but by way of example, a voltage differential of between 5 and 60 V, or 30 and 60 V, e.g., 40 or 60 V may be applied to the electrodes. When the direction of the voltage differential is reversed, for example to −40 or −60, the plate will deflect in the opposite direction. In this way, the piezoelectric actuator 5504 causes oscillation of ejector plate 5502 and generator plate 5532 which constitutes the vibration that results in formation of the droplets 5512 from fluid 5510. As the alternating voltage is applied to electrodes 5506a and 5506b, the ejector plate 5502 and the generator plate 5532 oscillate, causing the fluid droplets 5512 to accumulate in the openings 5526 and eventually to be ejected from the openings 5526 along the direction 5514 away from the reservoir 5520. The frequency and wavelength of oscillation may depend on many factors, including but not limited to, the thickness, composition and morphology and mechanical properties of the ejector plate 5502, including its stiffness, the properties of the generator plate 5532, the volume of the openings 5526, the number of openings 5526, composition and structure of the piezoelectric actuator 5504, piezoelectric actuation driving voltage, frequency and waveform, the viscosity of the fluid, temperature and other factors. These parameters may be adjusted or selected to create the desired droplet stream. The frequency of droplet ejection also depends on many factors. In some implementations, the droplets 5512 are ejected at a frequency lower than the pulse frequency applied to the piezoelectric actuator 5504. For example, the droplets 5512 are ejected every 1-1000 cycles, and more specifically 8-12 cycles, of the ejector plate/generator plate vibration (which vibrate at the same frequency as the actuator 5504). In some implementations, the generator plate comprises a high modulus polymeric generator plate.

In one embodiment of the present disclosure, as illustrated in FIG. 55 C, the ejector plate 5502 may be centro-symmetrically mounted by symmetric mounting structures 5555 through optional mounting holes 5551. Symmetric mounting structures may maximize the constant velocity surface area of ejector plate 5502, suppress anti-symmetric modes and mechanically match the piezoelectric material to the low order Bessel modes. In this embodiment there are four mounting tabs 5555 as shown in FIG. 1C. In another embodiment, there may be eight mounting tabs 5555. In yet another embodiment, there may be 16 mounting tabs 5555.

In certain aspects, the centro-symmetrical mounting provides for the use of piezoelectric materials that are lead free, e.g., $BaTiO_3$. In one embodiment of the disclosure, the resonance coupling of the ejector plate 5502 to a generator plate 5532 and to the piezoelectric actuator 5504 provides for the use of piezoelectric materials having smaller displacements than industry standard piezoelectric materials.

In accordance with certain embodiments of the disclosure, with reference to FIG. 55A, an ejector plate 5502 may be a simple ejector plate 5502 having an integrated generator plate 5532 having a center region 5530 and openings 5526. In other embodiments of the disclosure (FIGS. 55B-D) the ejector plate 1602 may be hybrid ejector plate 1602 having a coupled generator plate 5532 having a center region 5530 and openings 5526. The first surface 5522 of the ejector plate 5502 may be coupled to the generator plate 5532. The ejector plate 5502 may generally comprise a central open region 5552 configured to align with the generator plate 5532. The generator plate 5532 may then be coupled with the ejector plate 5502 such that a center region 5530 of the generator plate 5532 aligns with the central open region 5552 of the ejector plate 5502. The center region 5530 of the generator plate 5532 may generally include one or more openings or holes 5526, and alignment of the central open region 5552 of the ejector plate 5502 with the central region 5530 of the generator plate 5532 with its one or more openings 5526 allows for through communication of the one or more openings 5526. In some embodiments, the generator plate comprises a high modulus polymeric generator plate.

In certain embodiments, the central open region 5552 of the ejector plate 5502 may be smaller than the generator plate 5532 to provide sufficient overlap of material so as to allow for coupling of the ejector plate 5502 and the generator plate 5532. However, the central open region 5552 of the ejector plate 5502 should, in such embodiments, be sized and shaped so as to not interfere with or obstruct the center region 5530 (and thereby one or more openings 5526) of the generator plate 5532. By way of non-limiting example, the central open region 5552 of the ejector plate may be shaped in a manner similar to the generator plate 5532, and may be sized so as to have, for example, about 0.5 mm to about 4 mm, e.g., about 1 mm to about 4 mm, or about 1 mm to about 2 mm, etc., of overlap material available for coupling of the generator plate 5532 to the ejector plate 5502 (e.g., overlap on all sides). For instance, the central open region 5552 of the ejector plate may be shaped as a square, a rectangle, a circle, an oval, etc., in a manner to generally match the shape of the generator plate 5532, and sized such that the central open region 5552 is, for example, about 0.5 mm to about 4 mm smaller in overall dimensions (i.e., the diameter of a circle is about 0.5 to about 4 mm smaller, the major and minor axes of an oval are about 0.5 to about 4 mm smaller, the length of the sides of a square or rectangle are about 0.5 to about 4 mm smaller, etc.). In some embodiments, the generator plate comprises a high modulus polymeric generator plate.

Except as otherwise described herein, exemplary ejector mechanisms are disclosed in U.S. application Ser. No. 13/712,784, filed Dec. 12, 2012, entitled "Ejector Mechanisms, Devices, and Methods of Use", and Ser. No. 13/712,857, filed Dec. 12, 2012, entitled "High Modulus Polymeric Ejector Mechanism, Ejector Device, and Methods of Use," the contents of which are herein incorporated by reference in their entireties.

The generator plate 5532 may be coupled to the ejector plate 5502 using any suitable manner known in the art, depending on the materials in use. Examples of coupling methods include the use of adhesive and bonding materials, e.g., glues, epoxies, bonding agents, and adhesives such as loctite 409 or other suitable super glue, welding and bonding processing, e.g., ultrasonic or thermosonic bonding, thermal bonding, diffusion bonding, or press-fit etc.

Surface 5522 of ejector plate 5502 may also be coupled to a piezoelectric actuator 5504, which activates generator plate 5532 to form the droplets upon activation. The manner and location of attachment of the piezoelectric actuator 5504 to the ejector plate 5502 affects the operation of the ejector assembly 5500 and the creation of the droplet stream. In the embodiment of FIGS. 55B-C, the piezoelectric actuator 5504 may be coupled to a peripheral region of surface 5522 of plate 5502, while generator plate 5532 is coupled to surface 5522 so as to align with the central open region 5552 of ejector plate 5502, as described above. The piezoelectric actuator 5504 is generally coupled to the ejector plate 5502 so as to not cover or obstruct the central region 5530 (and thereby one or more openings 5526) of the generator plate 5532. In this manner, fluid 5510 may pass through the openings 5526 to form droplets 5512 (as shown in FIG. 55A).

The structure defined by the ejector plate 5502 and optionally coupled generator plate 5532 possesses a large number of eigenmodes which define, for each eigenmode, the shape the structure will take when said structure is excited. Examples of eigenmodes are presented in FIG. 3. For maximum ejection at any of these eigenmodes, the piezoelectric actuator 5504 must be shaped properly and placed in a position that provides the least amount of resistance to the deformation of the ejector plate 5502 and optionally coupled generator plate 5532 in the desired eigenmode. If the piezoelectric actuator 5504 provides a restriction on the shape of a given eigenmode the stiffness of the piezoelectric actuator 5504 and bonding layer may damp the mode (provide resistance toward continued movement), and may force the movement of the structure to be extremely dependent on the piezoelectric actuator 5504 material properties. This can limit the mass ejection in approximately the ratio of the piezoelectric actuator 5504 properties.

In some implementations, the ejector plate 5502 and optionally coupled generator plate 5532 eigenmodes can be excited with low or no resistance (other than the internal the ejector plate 5502 and optionally coupled generator plate 5532 resistance) to continued movement (ejector plate 5502 and optionally coupled generator plate 5532 resonance) simply by mounting the piezoelectric actuator 5504 to the edge of the ejector plate 5502 and optionally coupled generator plate 5532. By bonding the piezoelectric actuator 5504 to the edge of the ejector plate 5502 and optionally coupled generator plate 5532, the least possible resistance to ejector plate 5502 and optionally coupled generator plate 5532 movement can be provided. In an edge bonded, or near edge bonded embodiment, limitations of the piezoelectric actuator 5504 properties are minimized, as the mechanical resistance offered by the stiffness of the ceramic (e.g., the piezoelectric actuator 5504) and bonding to the eigenmode shapes is less than that of the ejector plate 5502 and optionally coupled generator plate 5532 itself.

In certain aspects of the present disclosure, the eigenmodes of the ejector plate 5502 and optionally coupled generator plate 5532 may be optimized by varying the dimensions of the piezoelectric actuator 5504. In an aspect, a given eigenmode may be excited by mounting the driving force (e.g., piezoelectric actuator 5504) at the right location, relative to the standing wave on the ejector plate 5502 and optionally coupled generator plate 5532, and constraining the dimensions of the piezoelectric actuator 5504—within the standing wave node or anti-node (depending on dominant radial or longitudinal drive mode). The eigenmodes of a ejector plate 5502 and optionally coupled generator plate 5532 and their shape can be found by solution of the Sturm-Liouville problem analytically.

While idealized eigenmodes of a membrane (e.g., a drum) may be found by solution of the Sturm-Liouville problem, in certain aspects of the present disclosure it becomes mathematically difficult or even intractable to analytically solve for the eigenmode shapes, frequencies, and corresponding amplitude coefficients of the vibration of an ejector plate 5502 and optionally coupled generator plate 5532. Analytical limitations to obtaining a solution to the Sturm-Liouville problem arise when an idealized membrane is loaded, includes a driving element, has a non-ideal boundary condition, or comprises multiple materials.

In aspects according to the present disclosure, the ejector plate 5502 and optionally coupled generator plate 5532 may include loads such as fluid 5510. In other aspects, the ejector plate 5502 and optionally coupled generator plate 5532 may include a piezoelectric actuator 5504 driving element. In another aspect, the ejector plate 5502 may include the coupled generator plate 5532 comprising one or more materials. In a further aspect, the ejector plate 5502 may be of non-uniform thickness. Similarly, in an aspect, the coupled generator plate 5532 may be of non-uniform thickness. In yet another aspect, the generator plate 5532 may have openings 5526 that are non-uniform and may lead to non-trivial analytical solutions.

The analytic limitations arising from a non-idealized membrane may be overcome. In certain aspects according to the present disclosure, computational software may be used which divides an entire structure into smaller discrete elements using Finite Element Methods (FEM). In an aspect, the computational software discretizes the structure into elements that may be one half or less of the size of the minimum wavelength (maximum frequency) of vibrational interest. In other aspects the discrete elements may be one fifth or less of the size of the minimum wavelength (maximum frequency) of vibrational interest. In other aspects, the discrete elements may be one tenth or less of the size of the minimum wavelength (maximum frequency) of vibrational interest. In another aspect of the present disclosure, the discrete elements may be one fifteenth or one twentieth or less of the size of the minimum wavelength (maximum frequency) of vibrational interest. In an aspect, the analytical problem comprising a partial differential equation may then be represented by the central differences at each point of the discrete elements. In another aspect the partial differential equation may be solved by finding a sum of basis functions that minimize the system energy.

In an aspect, using FEM techniques, the eigenmode frequencies and shapes may be determined through modal analysis for a given set of boundary conditions, such as free, simply supported, clamped, pinned, or some hybrid of these boundary conditions. In an aspect, the shape of the piezoelectric actuator 5504 may be determined by the eigenmode shape it is meant to drive. In certain aspects, the shape of the piezoelectric actuator 5504 is largely determined by the counterbalance of applied force per unit area, which is directly related to the area of the piezoelectric actuator 5504 in contact with the ejector plate 5502 and optionally coupled generator plate 5532, and the resistance or damping applied to the mode shape by the stiffness of the bonded piezoelectric actuator 5504.

In certain embodiments according to the present disclosure, once the piezoelectric actuator 5504 location and initial size is determined, it is modeled on the ejector plate 5502 and simulated with a voltage applied to the top of the piezoelectric actuator 5504 and grounded on the ejector plate 5502 and optionally coupled generator plate 5532 terminal. The ejector plate 5502 and optionally coupled generator plate 5532 can be a simple ejector plate 5502, a hybrid ejector plate 5502 having a coupled generator plate 5532, a simple or hybrid ejector plate 5502 having a 4 post structure, electric field screened structure, or any other combination of structures. The piezoelectric actuator 5504 excitation frequency is swept in the simulation from near zero frequency up to several hundred kilohertz (kHz), or more generally any frequency. The mode shape, amplitude of the displacement and velocity the simple or hybrid ejector plate 5502 experiences are computed for each frequency in the sweep. By applying FEM techniques, the amplitude and velocity of a design may be assessed.

If the ejector plate 5502/piezoelectric actuator 5504 system moves with adequate amplitude and velocity at the desired frequency the design is complete. If not, the design is tuned by thinning or thickening the piezoelectric actuator 5504 height in order to alter the damping of the ejector plate 5502 applied by the piezoelectric actuator 5504. In certain aspects, the piezoelectric actuator 5504 can also be tuned in lateral/radial thickness in order to reduce the damping of specific modes or to shift resonant frequencies either higher or lower. Simulations are repeated given the trending of the piezoelectric actuator 5504 sizing until design optimization is complete.

As the ejector assembly 5500 is used for delivering therapeutic agents or other fluids to the desired target, e.g., the eye, the ejector assembly 5500 may be designed to prevent the fluid 5510 contained in the reservoir 5520 and the ejected droplets 5512 from being contaminated. In some implementations, for example, a coating (not shown) may be formed over at least a portion of the exposed surface(s) of the piezoelectric actuator 5504, the ejector plate 5502, the generator plate 5532, etc., that are exposed to the fluids. The coating may be used to prevent direct contact of the piezoelectric actuator 5504 and the electrodes 5506a and 5506b with the fluid 5510. The coating may be used to prevent interaction of the ejector plate 5502 or generator plate 5532 with the fluid. The coating or a separate coating may also be used to protect the piezoelectric actuator 5504 and electrodes 5506a and 5506b from the environment. For example, the coating can be a conformal coating including a nonreactive material, e.g., polymers including polypropylene, nylon, or high density polyethylene (HDPE), gold, platinum, or palladium, or coatings such as Teflon®. Coatings are described in further detail herein.

The generator plate 5532 may be a perforated plate that contains at least one opening 5526. The one or more openings 5526 allow the droplets to form as fluid 5510 is passed into the openings and ejected from generator plate 5532. The generator plate 5532 may include any suitable configuration of openings. Examples of generator plates 5532 comprising high modulus polymers are illustrated in U.S. application Ser. No. 13/712,857, filed Dec. 12, 2012, entitled "High Modulus Polymeric Ejector Mechanism, Ejector Device, And Methods Of Use", the contents of which are herein incorporated by reference in its entirety for the purpose of such disclosures.

In some implementations, the ejector plate 5502 may be formed of a metal, e.g., stainless steel, nickel, cobalt, titanium, iridium, platinum, or palladium or alloys thereof. Alternatively, the plate can be formed of other suitable material, including other metals or polymers, and may be coated as described herein. The plate may be a composite of one or more materials or layers. The plate may be fabricated for example by cutting from sheet metal, pre-forming, rolling, casting or otherwise shaping. The coatings may also be deposited by suitable deposition techniques such as sputtering, vapor deposition including physical vapor deposition (PAD), chemical vapor deposition (COD), or electrostatic powder deposition. The protective coating may have a thickness of about less than 0.1 μm to about 500 μm. It is desirable that the coating adhere to the ejector plate 5502 sufficiently to prevent delamination when vibrating at a high frequency.

Referring to FIGS. 55B and 55D, in one implementation, the ejector plate 5502 and generator plate 5532 may have concentric circular shapes. In certain embodiments, the ejector plate may be larger than the generator plate, so as to accommodate coupling of the generator plate and other components (e.g., piezoelectric actuator, etc.) described herein. In certain embodiments, the overall size or diameter of the generator plate 5532 may be, at least in part, determined by the size of central region 5530 and by the arrangement of openings 5526. In some embodiments, the generator plate comprises a high modulus polymeric generator plate.

However, both plates may independently have other shapes, e.g., an oval, square, rectangular, or generally polygonal shape, and may be the same or different. Overall size and shape may be any suitable size and shape, and may be selected based on ejector device design parameters, e.g., size and shape of an outer device housing, etc. Additionally, the plates need not be flat, and may include a surface curvature making it concave or convex. The piezoelectric actuator 5504 may be of any suitable shape or material. For example, the actuator may have a circular, oval, square, rectangular, or a generally polygonal shape. The actuator 5504 may conform to the shape of the ejector plate 5502, generator plate 5532, or regions 5530 or 5552. Alternatively, the actuator 5504 may have a different shape. Furthermore, the actuator 5504 may be coupled to the ejector plate 5502 or surface 5522 of the ejector plate 5502 in one or more sections. In the example shown in FIGS. 55B-D, the piezoelectric actuator 5504 is in the shape of a ring that is concentric to the ejector plate 5502, generator plate 5532, and regions 5530/5552.

In some implementations, the ejector plate 5502 and/or generator plate 5532 may be coated with a protective coating that has anti-contamination and/or anti-microbial properties. The protective coating can be conformal over all surfaces of the ejector plate and/or generator plate, including surfaces defining the openings 5526. In other implementations, the protective coating can be applied over selected surfaces, e.g., the surfaces 5522, 5525, or surface regions, e.g., parts of such surfaces. The protective coating can be formed of a biocompatible metal, e.g., gold, iridium, rhodium, platinum, palladium or alloys thereof, or a biocompatible polymer, e.g., polypropylene, HDPE, or Teflon®. Antimicrobial materials include metals such as silver, silver oxide, selenium or polymers such as polyketones. The protective coating can be in direct contact with the fluid 5510 or the droplets 5512. The coating may provide an inert barrier around the fluid or may inhibit microbial growth and sanitize the fluid 5510 and/or the droplets 5512.

Additionally, one or both of the surface 5522 of ejector plate 5502 and the wetted surface of generator plate 5532 that faces the reservoir 5520 may be coated with a hydrophilic or hydrophobic coating. Additionally, the coating may be coated with a protective layer. The surfaces may also be coated with a reflective layer. A coating layer may be both protective and reflective. Alternatively, one or more of the surfaces may have been formed to be reflective. For example, the surfaces may be made of stainless, nickel-cobalt, or other reflective material. A surface may have been formed or polished to be reflective. In addition to making the surface reflective, the surface may also be backlit on its surface or around its perimeter. In ophthalmic applications, a reflective surface aids the user in aligning the ejector assembly with the eye.

If desired, surfaces of the ejector assembly may include coatings that may be pre-formed by dipping, plating, including electroplating, or otherwise encapsulating, such as by molding or casting. The coatings may also be deposited by suitable deposition techniques such as sputtering, vapor deposition, including physical vapor deposition (PAD) and chemical vapor deposition (COD), or electrostatic powder deposition. The protective coating may have a thickness of less than 0.1 μm to about 500 μm. It is desirable that the coating adhere to the plate sufficiently to prevent delamination when vibrating at a high frequency.

Piezoelectric actuator 5504 may be formed from any suitable material known in the art. By way of example, in some implementations, the piezoelectric actuator can be formed from PZT, barium titanate or polymer-based piezoelectric materials, such as polyvinylidine fluoride. The electrodes 5506a and 5506b can be formed of suitable conductors including gold, platinum, or silver. Suitable materials for use as the adhesive 5528 can include, but is not be limited to, adhesives such as silicone adhesives, epoxies, or silver paste. One example of a conductive adhesive includes Thixotropic adhesive such as Dow Corning DA6524 and DA6533. The reservoir 5520 may be formed of a polymer material, a few examples of which include Teflon®, rubber, polypropylene, polyethylene, or silicone.

Piezoelectric ceramic materials are isotropic in the unpolarized state, but they become anisotropic in the polarized state. In anisotropic materials, both the electric field and electric displacement must be represented as vectors with three dimensions in a fashion similar to the mechanical force vector. This is a direct result of the dependency of the ratio of dielectric displacement, D, to electric field, E, upon the orientation of the capacitor plate to the crystal (or poled ceramic) axes. This means that the general equation for electric displacement can be written as a state variable equation:

$$D_i = \in_{ij} E_j$$

The electric displacement is always parallel to the electric field, thus each electric displacement vector, $D_i$, is equal to the sum of the field vectors, $E_j$, multiplied by their corresponding dielectric constant, $\in_{ij}$:

$$D_1 = \in_{11} E_1 + \in_{12} E_2 + \in_{13} E_3$$

$$D_2 = \in_{21} E_1 + \in_{22} E_2 + \in_{23} E_3$$

$$D_3 = \in_{31} E_1 + \in_{32} E_2 + \in_{33} E_3$$

The majority of the dielectric constants for piezoelectric ceramics (as opposed to single crystal piezoelectric materials) are zero. The only non-zero terms are:

$$\in_{11} = \in_{22}, \in_{33}$$

The piezoelectric effect relates mechanical effects to electrical effects. These effects are highly dependent upon their orientation to the poled axis. The axis numbering scheme is shown in FIG. 56. For example, for the electro-mechanical constant $d_{ab}$, a=electrical direction; b=mechanical direction and for electro-mechanical constant $D_{33} = \in_{33} E_3$ with mechanical displacement in the poled direction, Z in this case. Referring to FIG. 55A, the Z direction is the direction of the ejected droplets 5512, direction 5514.

Accordingly, $D_{33}$ is the induced polarization in direction Z (poled direction, corresponding to direction 5514 in FIG. 55A) which is parallel to the direction in which the ceramic material is polarized.

In accordance with certain embodiments of the disclosure, piezoelectric materials may be described by mechanical displacement in the poled direction, Z (e.g. direction 5514 of FIG. 55A).

In some embodiments, the piezoelectric material may be a lead Zirconium titanate (PZT) having a $D_{33}$=330 pC/N. In an another embodiment, the piezoelectric material may be a type of a PbTiO3-PbZrO3 (PZT)-based multi-component system that is widely used. Commercially available PZT piezoelectric ceramics include PZT-4 having a $D_{33}$ of 225 pC/N, PZT-5A having a $D_{33}$ of 350 pC/N, and PZT-5H having a $D_{33}$ of 585 pC/N. The (PZT)-based piezoelectric actuator can be formed from a material having a $D_{33}$ of greater than 300 pC/N. In another embodiment, the piezoelectric ceramic may have a $D_{33}$ of 200 pC/N to 300 pC/N. In another embodiment, the piezoelectric ceramic may have a $D_{33}$ of 250 pC/N to 300 pC/N.

In some implementations, it may be desirable to eliminate lead from the piezoelectric material for safety reasons and FDA/EU compliance. In an implementation, a lead free piezoelectric ceramic may be used having a $D_{33}$ of less than 300 pC/N. In another embodiment, a lead free piezoelectric ceramic may have a $D_{33}$ of less than 200. In yet another embodiment, a lead free piezoelectric ceramic may have a $D_{33}$ of between 150 pC/N and 200 pC/N. In yet another embodiment, the D33 of the lead free ceramic may be less than 150 pC/N. In yet another embodiment, a lead free piezoelectric ceramic may have a $D_{33}$ of between 100 and 150 pC/N. In yet another embodiment, the $D_{33}$ of a lead free ceramic suitable for a piezoelectric actuator may be less than 100 pC/N.

In some embodiments the piezoelectric device may be prepared from commercially available materials. For a non-limiting example, materials available from Sunnytec Powder Materials presented in Table 14 may be suitable for piezoelectric devices of the disclosure.

TABLE 14

| Materials Physical & Properties | | S-42 P-42 | S-44 FM-2-1 | S-44-2 SP-12-4 | S-81 P-8 | S-51 P-5A | S-52 FT-3 | S-53 FT-4 | S-54 P-5H | S-55 TK-4800 | S101-D S101-D | S101-F S101-F |
|---|---|---|---|---|---|---|---|---|---|---|---|---|
| Density (g/cm³) | p | 7.6 | 7.7 | 7.7 | 7.6 | 7.6 | 7.56 | 7.56 | 7.6 | 7.7 | 7.55 | 7.6 |
| Curie temperature (° C.) | Tc | 305 | 300 | 280 | 320 | 260 | 280 | 250 | 180 | 170 | 185 | 165 |
| Dielectric constants | 33 T/0 | 1450 | 1550 | 1600 | 1030 | 2300 | 2200 | 3200 | 3800 | 4600 | 3200 | 4200 |
| Dissipation factor (%) | tgo | 0.4 | 0.4 | 0.5 | 0.3 | 1.5 | 1.8 | 1.8 | 1.7 | 2 | 1.6 | 1.6 |
| Coupling Coefficients (%) | $K_p$ | 65 | 68 | 66 | 58 | 71 | 80 | 81 | 77 | 81 | 72 | 68 |
| | Kt | 48 | 48 | 47 | 46 | 51 | 51 | 52 | 52 | 51 | 50 | 46 |
| | K31 | 33 | 34 | 35 | 30 | 38 | 43 | 44 | 42 | 45 | 38 | 36 |
| Frequency constants (MHz) | $N_p$ | 2230 | 2250 | 2220 | 2300 | 2080 | 1960 | 1950 | 1980 | 1950 | 2030 | 2100 |
| | Nt | 2050 | 2050 | 2080 | 2050 | 2040 | 2030 | 2045 | 2040 | 2020 | 2040 | 2100 |
| | NL | 1650 | 1630 | 1630 | 1655 | 1545 | 1420 | 1420 | 1500 | 1465 | 1510 | 1545 |
| Mechanical quality factor | Qm | 600 | 1400 | 1200 | 1000 | 80 | 70 | 65 | 65 | 55 | 100 | 70 |
| Piezoelectric Charge Constants (×10−12 M/V) | d33 | 320 | 330 | 330 | 250 | 450 | 550 | 640 | 650 | 750 | 620 | 650 |
| | d31 | −155 | −135 | −140 | −110 | −200 | −260 | −300 | −290 | −300 | −250 | −265 |
| Piezoelectric voltage constants (×10−3 Vm/N) | g33 | 25.8 | 23.4 | 23.2 | 27.4 | 22.1 | 28.2 | 22.6 | 19.3 | 18.4 | 21.8 | 17.4 |
| | g31 | −12.5 | −10.5 | −10.2 | −9.8 | −11.1 | −11.5 | −10.8 | −8.6 | −7.5 | −8.5 | −7.1 |
| Elastic constants (×10−12 m2/N) | SE11 | 11.5 | 12.5 | 12.1 | 12.1 | 13.8 | 16.2 | 16.5 | 14.1 | 15.2 | 14.5 | 13.7 |
| | SD11 | 10.2 | 11.2 | 11.1 | 10.9 | 11.8 | 13.3 | 13.2 | 11.6 | 12.9 | 12.3 | 11.8 |

In some embodiments, the piezoelectric material may be a $BiFeO_3$-based ceramic. In some embodiments, the ceramic may be selected from the group consisting of (Bi,Ba)(Fe, Ti)$O_3$, (K,Na,Li)Nb$O_3$, (K,Na,Li)Nb$O_3$, (K,Na,Li)Nb$O_3$, (K,Na,Li)NbO3, Bi(Fe,Mn)$O_3$+BaTi$O_3$, Bi(Fe,Mn)$O_3$+BaTi$O_3$, $BiFeO_3$—NdMn$O_3$—BiAlO3, (Bi,La)(Fe,Mn)$O_3$, (Bi,La)(Fe,Mn)O3, BiFeMnO3-BaTi$O_3$, Bi(Fe,Mn)O3-BaZrTi$O_3$, (Bi,La)(Fe,Mn)$O_3$, (Bi,La)(Fe,Mn)$O_3$, (Bi,Ba)(Fe, Ti)$O_3$, Bi(Zn,Ti)$O_3$—La(Zn,Ti)$O_3$—Ba(Sc,Nb)$O_3$ (d33=250), $BiFeO_3$, (Ba, M)(Ti,Ni)$O_3$, $BiFeO_3$, Bi(Al,Ga)$O_3$, BT-$BiFeO_3$, Bi(Fe,Al)$O_3$, Bi(Fe,Al)$O_3$, Bi(Fe,Co,Mn)$O_3$, $BiFeO_3$—BaTi$O_3$, $BiFeO_3$—BaTi$O_3$, Bi(Al,Ga)$O_3$ (d33=150), Bi(Al,Ga)$O_3$, $BiFeO_3$+AD, $BiFeO_3$+BaTi$O_3$, $BiFeO_3$-based, BaTi$O_3$—$BiFeO_3$, (Bi, x)(Fe,Mn)$O_3$, and (Bi, x)(Fe, Ti,Mn)$O_3$.

In some embodiments, the piezoelectric material may be a bismuth sodium titanate (BNT) material or a bismuth potassium titanate (BKT) material. The BNT or BKT material may be selected from the group consisting of (1-x)$Bi_{0.5}Na_{0.5}TiO_3$— xLaFe$O_3$, (1-x)$Bi_{0.5}Na_{0.5}TiO_3$—xNaSb$O_3$, (1-x)$Bi_{0.5}Na_{0.5}TiO_3$— xBiCr$O_3$, (1-x)$Bi_{0.5}Na_{0.5}TiO_3$— xBiFe$O_3$, $Bi_{0.5}(Na_{1-x}K_x)_{0.5}TiO_3$ (BNKT), $Bi_{0.5}(Na_{1-x}K_x)_{0.5}TiO_3$ (BNKT), $Bi_{0.5}(Na_{1-x}K_x)_{0.5}TiO_3$ (BNKT), $Bi_{0.5}(Na_{1-x}K_x)_{0.5}TiO_3$ (BNKT), ((1-x)$Bi_{1-a}Na_a)TiO_3$— (1-x)LiNb$O_3$, $Bi_{0.5}(Na_{1-x}Li_x)_{0.5}TiO_3$, $Bi_{0.5}(Na,K)_{0.5}[Ti, (Mg, Ta)]O_3$, $Bi_{0.5}(Na,K)_{0.5}[Ti,(Al, Mo)]O_3$, $Bi_{0.5}(Na,K)_{0.5}[Ti,(Mg, Nb)]O_3$, $Bi_{0.5}(Na,K)_{0.5}[Ti,(M, V)]O_3$, $Bi_{0.5}(Na,K)_{0.5}[Ti,(M,V)]O_3$, BNT-BT-KNN, (1-x)$Bi_{0.5}Na_{0.5}TiO_3$— xBaTi$O_3$ (BNBT) ($d_{33}$=100×10$^{-12}$C/N or more), BNT-BKT-BT ($d_{33}$=158pC/N), BNT-BKT-BT+PT ($d_{33}$=127), BNT-KN, $Bi_{0.5}Na_{0.5}TiO_3$— BaTi$O_3$ (BNBT) ($d_{33}$=253pC/N), NGK2, BNT-BKT-BT, NGK, BNT-BKT-BT, NGK4, $Bi_{0.5}Na_{0.5}TiO_3$— BaTi$O_3$—CaTi$O_3$—Ba(Zn$_{1/3}$Nb$_{2/3}$)$O_3$+Y$_2$O$_3$, MnO, (1-v)[(Li$_{1-y}$Na$_y$)zNb$O_3$]-v[$Bi_{0.5}Na_{0.5}TiO_3$], (1-v-x)[(Li$_{1-y}$Na$_y$)zNb$O_3$]-xLMn$O_3$-v[$Bi_{0.5}Na_{0.5}TiO_3$], $Bi_{0.5}Na_{0.5}TiO_3$, BNT-BT, BNT-BT, x$Bi_{0.5}Na_{0.5}TiO_3$— y(MNb$O_3$)— (Z/2)(Bi$_2$O$_3$—Sc$_2$O$_3$) (M=K, Na), BNT-BKT-Bi(Mg2/3Ta1/3)O3, [(Bi$_{0.5}$Na$_{0.5}$)xMy]z(TiuNv)$O_3$ (M=Ba, Mg, Ca, Sr, (Bi$_{0.5}$K$_{0.5}$)) (N=Zr, Hf), [(Bi$_{0.5}$Na$_{0.5}$)xMy]z(TiuNv)$O_3$ (M=Ba, Mg, Ca, Sr, (Bi$_{0.5}$K$_{0.5}$), others) (N=Zr, Hf, others), BNT-BKT-BT-CT-NaNb$O_3$, BNT-BKT-Bi(Ni,Ti)$O_3$, BNT-BKT-Bi(Ni,Ti)$O_3$, BNT-BKT-BT, BNT-BT-ST, BNT-BKT-BT, BNT-BKT-Ag-NbO$_3$, BNT-BKT-BT, BT-BKT, BNT-BT-Bi(Fe0.5Ti0.5)3, BNT-BKT-Bi(Zn0.5Zr0.5)O3, BNT-BKT-Bi(Fe0.5Ta0.5)O3, BNT-BKT-Bi(M1,M2)O3, BNT-BKT, BNT-BT, BNT-BKT, $Bi_{0.5}K_{0.5}TiO_3$ (BKT) and $Bi_{0.5}Na_{0.5}TiO_3$— (1-x) AB$O_3$.

In some implementations, the piezoelectric material may be a dual-mode magnetostrictive/piezoelectric bilayered composite, tungsten-bronze material, a sodium niobate material, a barium titanate material, and a polyvinylidine fluoride material. Examples of suitable materials for the piezoelectric actuator of the disclosure include A2Bi4Ti5O18 (A=Sr,Ca,(Bi$_{0.5}$Na$_{0.5}$),(Bi$_{0.5}$Li$_{0.5}$), ((Al-xBix)2Bi4Ti5O18 (A=Sr,Ca,(Bi$_{0.5}$Na$_{0.5}$), (,(Bi$_{0.5}$Li$_{0.5}$), (Bi$_{0.5}$Li0.5), Bi4TiO12-x(Sr1-aA'a)TiO3 (A=Ba, Bi$_{0.5}$Na0.5, Bi$_{0.5}$K0.5, Bi$_{0.5}$Li0.5), Bi4Ti3O12-(Ba, A)TiO$_3$, Bi4Ti3O12-x{(Sr1-aA'a)TiO3-AB$O_3$} (A'=Ba, Bi$_{0.5}$Na0.5, Bi$_{0.5}$K0.5, Bi0.5Li0.5, A=Bi,Na,K,Li, B=Fe,Nb), (Al-xBix)Bi4Ti4O15 (A=Sr,Ba), BaBi4Ti4O15, (Sr2-aAa)x(Na1-bKb)y(Nb5-cVc)O15 (A=Mg, Ca, Ba) d33=80pC/N or more, Tc=150° C. or more, (Sr2-aAa)x(Na1-bKb)y(Nb5-cVc)O15, (Na0.5 Bi$_{0.5}$)1-xMxBi4Ti4O15, Bi4Ti3O12, SrBi2(Nb,W)O9, (Sr1-xM1x)Bi2(Nb1-zWy)2O9, (Sr, Ca)NdBi2Ta2O9+Mn, (Sr1-xMx)(Bi, Nd)(Nb, Ta)2O9, Bi2(Sr1-xMx)Nb2O9 (M=Y, La), (Sr2CaK)Nb5O15 (d33=120).

In implementations according to the disclosure, the niobate material may be selected from (Sn,K)(Ti,Nb)O3, KNbO3-NaNbO3-LiNbO3-SrTiO3-BiFeO3, KNbO3-NaNbO3-LiNbO3, KNbO3-NaNbO3-LiNbO3, xLiNbO3-yNaNbO3-zBaNb2O6, NaxNbO3-AyBOf (A=K,Na,Li,Bi B=Li,Ti,Nb,Ta,Sb), (1-x)(Na1-aMna)b(Nb1-aTia)O3-xMb-TiO3 (M=(Bi1/2K1/2),Bi1/2Na1/2),(Bi1/2Li1/2), Ba, Sr, (K,Na,Li)NbO3-Bi(Mg,Nb)O3-Ba(Mg,Nb)O3, (1-x)[(Li1-yNay)zRO3]-xLMnO3(R=Nb,Ta,Sb, L=Y,Er,Ho,Tm, Lu, Yb), (LixNa1-x-yKy)z-2wMa2wNb1-wMbwO3 (Ma=$^{2+}$ metal A, Mb=$^{3+}$ metal B), NN-BT d33=164, K1-xNaxNbO3+ Sc$_2$O$_3$, [(K1-xNax)1-yAgy]NbO3-z[Ma+]

[O2-] (M=additive), Li(K,Na)(Nb,Sb)O3, KNbO3-NaNbO3 (d33=200), (Li,Na,K)(Nb,Ta,Sb)O3, (K,Na,Li)NbO3, KNbO3+MeO3 (MnWO3. etc.) (d33=130).

Barium titanate material is an inorganic compound with the chemical formula $BaTiO_3$. Barium titanate materials include $BaTiO_3$ materials that further comprise substoichiometric amounts of other elements. Examples of other elements that are included in $BaTiO_3$ materials include rare earth elements and alkaline earth metals. The substoichiometric amounts of other elements modify the piezoelectric properties of the $BaTiO_3$ materials. Doping of $BaTiO_3$ materials refers to the inclusion of substoichiometric amounts of other elements.

Examples of suitable single crystal barium titanate materials further include {(Bi1/2,Na1/2)1-xAlx}TiO3 (A1=Ba, Ca, Sr), {(Bi1/2,Na1/2)1-x(Bi1/2, A21/2)xTiO3 (A1=Ba, Ca, Sr, A2=Li, K, Rb) (Single crystal), (Sr,Ba) 3TaGa3Si2O14, La3-xSrxTayGa6-y-zSizO14, (Ba,Ca)TiO3, $LiNbO_3$, $LiTaO_3$, (K3Li2)1-xNaxNb5O15, La3Ga5SiO14, MgBa(CO3)2, NdCa4O(BO3)3 (M1=rare earth elements, M2=alkaline earth metals), LaTiO2N.

In some implementations, the ejector plate 5502 may be formed of a suitable material where the suitable material is selected based on out of plane displacement, direction 5514. The ejector plate 5502 displacement Z (e.g. movement in the direction 5514), depends on the diameter of the ejector plate 5502 and the thickness of the ejector plate 5502. The suitable material may also be selected in view of the Young's Modulus and Poisson's Ratio of the ejector plate 5502. The Young's Modulus and Poison's Ratio are intrinsic properties of the material and conforming materials can be selected to determine a desired displacement. For a suitable material for the ejector plate 5502, displacement Z may be increased by decreasing the thickness of the ejector plate 5502.

Suitable materials for ejector plate 5502, having a displacement in direction 5514 can be coupled to the frequency of the piezoelectric actuator 5504 so that the resonant frequency of the ejector plate 5502 is matched. By coupling the displacement of the ejector plate 5502 with the piezoelectric actuator 5504 in a resonance system, the ejection of liquid through the holes of the generator plate 5532 can be accomplished with piezoelectric actuator that are not limited by $D_{33}$ values.

Referring to FIG. 55C, the manner and location of attachment of the piezoelectric actuator 5504 to the ejector plate 5502 may affect the operation of the ejector assembly 5500 and the creation of the droplet stream.

As discussed above, the ejector plate 5502, whether as a simple ejector plate 5502 or as a hybrid ejector plate 5502 coupled to a generator plate 5502, may possess a large number of eigenmodes which define, for each eigenmode, the shape the structure will take when said mode is excited. As provided above, using for example FEM techniques, the eigenmodes of an ejector plate 5502 and optionally coupled generator plate 5532 may be calculated and the desired amplitude and velocity of the eigenmodes determined.

In one embodiment, the piezoelectric actuator 5504 is edge-mounted on the ejector plate 5502 where the distance 5554 is zero. An edge mount design is a special case which has near zero inherent resistance to modes it is designed to excite. When a circular piezoelectric actuator 5504 is bonded to the edge of a circular ejector plate 5502 (e.g., the distance 5554 is at or near zero) the ejector plate 5502 is stiffened considerably where a stiff piezoelectric actuator 5504 is placed, but the portion of the ejector plate 5502 on the inside of the piezoelectric actuator 5504 inner diameter 5557 is left to move freely, restricted only by its own limits of elasticity rather than the piezoelectric actuator 5504. Similarly, hybrid ejector plates 5502 having a coupled generator plate 5532 would also be left to move freely, restricted only by the combined limits of elasticity rather than the piezoelectric actuator 5504. If the edges of the piezoelectric actuator 5504 are pinned or clamped, the ejector plate 5502 behaves virtually as though it was the diameter of inner diameter 5557 of the piezoelectric actuator 5504 with ideal (edge driven) radial and longitudinal excitation. Other modes relevant to the entire size of the ejector plate 5502 are suppressed due to the stiffness of the piezoelectric actuator 5504. In certain embodiments, the stiffness of the piezoelectric actuator 5504 may be modulated by increasing or decreasing the thickness of a piezoelectric actuator 5504. Embodiments illustrating the modulation of piezoelectric actuator 5504 are presented in Example 5 below.

In other embodiments according to the present disclosure, the mounting configuration of the piezoelectric actuator 5504 to the ejector plate 5502 effects the displacement and velocity of the ejector plate 5502 and the generator plate 5532. In general, the amplitude of displacement and the velocity of the ejector plate 5502 in a given mode is a balance between the force, largely determined by the movement per unit voltage ($D_{33}$) of the piezoelectric material, and the damping/resistance that a piezoelectric presents to the ejector plate 5502 movement. Increasing stiffness of the piezoelectric material increases the damping and resistance. For embodiments of the present disclosure having piezoelectric materials having a large $D_{33}$, for example materials like PZT, the damping/resistance of the piezoelectric material plays a less significant role in the amplitude of displacement. In other embodiments with a lower $D_{33}$, for example $BaTiO_3$, the performance of a droplet ejector system may be significantly decreased by the damping/resistance. The performance of an ejector assembly 5500 reduces in direct proportion to the $D_{33}$ of the material used to prepare a piezoelectric activator 5504.

The properties of an edge mounted embodiment of a piezoelectric actuator 5504/ejector plate 5502 can be used to bypass the effects of lower material movement. Specifically, when the ejector plate 5502 is excited in a mechanical mode where only its own resistance limits its movement due to a given force per unit area applied by the piezoelectric actuator 5504, the piezoelectric $D_{33}$ can be scaled down with no impact on performance for the same electrical input until a minimum force per unit area value is reached. This property is illustrated in FIG. 8, where if the force per unit area is above a certain threshold, the increase in ejector plate 5502 movement is very small. Below this threshold, the ejector plate 5502 movement decreases linearly with force per unit area.

For ejector plates 5502 of the present disclosure, low order modes are generally excited at the lowest frequencies on a structure where the wavelength of the standing wave is an integer multiple of a half wavelength. The frequency and wavelength of this mode is determined by the material properties of the ejector plates 5502 and its radial dimension. As the eigenmode shape always possesses a node at the edges of the ejector plates 5502 for these modes and a maximum at the center of the membrane, only two piezoelectric locations are relevant for exciting these modes in a fluid ejection system.

In an embodiment according to the present disclosure, a piezoelectric actuator 5504 can be placed in the center of the ejector plate 5502 in order to excite maximum movement. However, because there must be an area directly in the center of the ejector plate 5502 for fluid ejection to take place, this mounting position is not optimum for this application. Performance must be sacrificed to allow fluid ejection.

A piezoelectric actuator 5504 can likewise be placed at the edge of the ejector plate 5502 to excite maximum movement in the center of the ejector plate 5502 at low frequencies. In this configuration, minimum resistance to the natural movement of the mode occurs, allowing large displacements at low frequencies and enhanced mass depositions in these modes. Generally, these modes are favorable for continuous fluid ejection due to their nearly constant shape and velocity distribution over the ejection area. Furthermore, loading the center of the ejector plate 5502 with a mass, such as in a hybrid ejector plate 5502 having a coupled generator plate 5532, enhances low order mode displacement due to the inertia of the center mass (e.g. generator plate 5532).

In some embodiments, the edge-mounted piezoelectric actuator 5504 oscillates the ejector plate 5502 coupled to the generator plate 5532 at the resonant frequency of the ejector plate coupled to said generator plate. In one embodiment, matching the resonant frequency decreases the displacement requirement of the piezoelectric material. In one embodiment, the resonant frequency matching provides for the generation of a directed stream of droplets using a piezoelectric material having a $D_{33}$ of less than 200. In another embodiment, the resonant frequency matching provides for the generation of a directed stream of droplets using a piezoelectric material having a $D_{33}$ of less than 150 or less than 125. In yet another embodiment, the resonant frequency matching provides for the generation of a directed stream of droplets using a piezoelectric material having a $D_{33}$ of less than 100 or less than 75.

In another embodiment, the piezoelectric actuator 5504 is slightly less than edge mounted (e.g., inside mounted) on the ejector plate 5502 where the distance 5554 is greater than zero. In one embodiment, the distance 5554 may be 0.05 mm. In another embodiment, the distance 5554 may be 0.01 mm. In yet another embodiment, the distance 5554 may be 0.25 mm. In yet another embodiment, the distance 5554 may be 0.5 mm. In further embodiments, the distance 5554 may be 0.75 mm, or 1.0 mm, or may be greater than 1.0 mm.

In other embodiments according to the present disclosure, the piezoelectric actuator 5504 is inside mounted on the ejector plate 5502 where the distance 5554 is greater than zero and the outer diameter of piezoelectric actuator 5504 is smaller than ejector plate 5502. In an embodiment, the piezoelectric actuator 5504 is inside mounted on the ejector plate 5502 and is 1% smaller than the diameter of ejector plate 5502. In an embodiment, the piezoelectric actuator 5504 is inside mounted on the ejector plate 5502 and is 1.5% smaller than the diameter of ejector plate 5502. In an embodiment, the piezoelectric actuator 5504 is inside mounted on the ejector plate 5502 and is 2% smaller than the diameter of ejector plate 5502. In an embodiment, the piezoelectric actuator 5504 is inside mounted on the ejector plate 5502 and is 3% smaller than the diameter of ejector plate 5502. In an embodiment, the piezoelectric actuator 5504 is inside mounted on the ejector plate 5502 and is 4% smaller than the diameter of ejector plate 5502. In an embodiment, the piezoelectric actuator 5504 is inside mounted on the ejector plate 5502 and is 5% smaller than the diameter of ejector plate 5502. In an embodiment, the piezoelectric actuator 5504 is inside mounted on the ejector plate 5502 and is 7.5% smaller than the diameter of ejector plate 5502.

In some embodiments according to the present disclosure, the piezoelectric actuator 5504 is inside mounted on the ejector plate 5502 where the distance 5554 is greater than zero and the inner diameter of the annular piezo actuator is selected so that the low frequency edge mode of the ejector plate 5502 is damped or eliminated.

In certain embodiments of the disclosure, the ejector mechanism may be configured so as to facilitate actuation of the ejector plate 5502, and thereby the generator plate 5532, by the piezoelectric actuator. As described above, the generator plate 5532 may be configured to optimize ejection of a fluid of interest. For example, the aspect ratio of the openings of the generator plate may be selected based, in part, on fluid properties, such that the general thickness of the generator plate 5532 ranges from about 50 µm to about 200 µm, as described above. Without being limited by theory, in certain implementations, direct actuation of a relatively thick generator plate, though possible, may be less optimal. In some implementations, the generator plate comprises a high modulus polymeric generator plate.

As such, in certain implementations, actuation of the ejector mechanism may be optimized using configurations including a generator plate coupled to an ejector plate, as described herein. In addition, reducing the surface area of the generator plate 5532 (i.e., the central region having one or more openings) likewise reduces manufacturing costs, reduces potential manufacturing defects, and increases manufacturing efficiencies and output. In certain embodiments, the ejector plate may be sized and shaped in a manner to facilitate actuation of the ejector mechanism (i.e., actuation of the ejector plate and thereby the generator plate). By way of example, configurations of the ejector plate may effectuate actuation of the ejector mechanism through selection of properties (e.g., size, shape, material, etc.) that facilitate flex of the ejector plate, and thereby vibration of the generator plate. For instance, the ejector plate 5532 may have a thickness generally ranging from about 10 µm to about 400 µm, from about 20 µm to about 100 µm, from about 20 µm to about 50 µm, or from about 30 µm to about 50 µm, etc. Again, without being limited by theory, in certain implementations, direct actuation of a relatively thinner ejector plate 5502 (compared to the generator plate 5532), may be more optimal. In some implementations, the generator plate 5532 comprises a high modulus polymeric generator plate.

In accordance with certain implementations of the disclosure, the configuration of the ejector plate 5502 and the generator plate 5532 may be selected such that the center region of the generator plate 5532 including openings (the "active region" of the generator plate) produces a symmetric oscillation with a normal mode of oscillation. Without being limited by theory, in certain implementations, configurations of the ejector plate 5502 and generator plate 5532 may be selected such that 0.2 normal mode and 0.3 normal mode of oscillation of the active region of the generator plate is observed. The mode is associated with a maximum amplitude and displacement of the active region, wherein the mode is designated as (d,c) where d is the number of nodal diameters and c is the number of nodal circles.

The magnitude and frequency of the ejector plate 5502 vibration can also be controlled by controlling the voltage pulses applied to the electrodes 5506a, 5506b, e.g., a voltage differential of 40 or 60 V may be applied to the electrodes. As discussed above, the pulses are created by voltage differentials that deflect the ejector plate 5502, and thereby generator plate 5532. In some implementations, one of the electrodes 5506a or 5506b is grounded and voltage pulses, e.g., bipolar pulses, are applied to the other one of the electrodes 5506a or 5506b e.g., to vibrate the ejector plate 5502. By way of example, in one implementation, the piezoelectric actuator 5504 can have a resonant frequency of about 5 kHz to about 1 MHz, e.g., about 10 kHz to about 160 kHz, e.g., about 50-120 kHz or about 50-140 kHz, or about 108-130 kHz, etc. The applied voltage pulses can have a frequency lower, higher, or the same as the resonant frequency of the piezoelectric actuator 5504.

In certain implementations, delivery time of the droplets is about 0.1 ms to about several seconds. Without wishing to be bound by theory, it is believed that human eyes take about 300 ms to about 400 ms for a blink. Therefore, for implementations where delivery is desired to be within the duration of a blink, the delivery time may be about 50 ms to about 300 ms and more particularly 25 ms to 200 ms. In one implementation, the delivery time is 50 ms to 100 ms. In this way, the ejected droplets can be effectively delivered and deposited in the eye during a blinking cycle of the eye. In some implementations, for example over-the-counter saline dispensers, the delivery time can be as long as several seconds, e.g., 3-4 seconds, spanning several blink cycles. Alternatively, a single dosage can be administered over several bursts or pulses of droplet ejection. Additionally, and not intending to be limited by theory, pulsing may be used to reduce the peak amplitude of the droplet airstream by spreading the impulse out over time. Therefore, the pressure of the ejection on the target may be mitigated. Furthermore, pulsing may also reduce droplet agglomeration and result in less entrained air generation. By way of example, pulses of 25 ms can be administered with stop times of 25 ms separating the pulses. In one implementation, the pulses may be repeated for a total of 150 ms.

As described herein, the ejector device and ejector mechanism of the disclosure may be configured to eject a fluid of generally low to relatively high viscosity as a stream of droplets. By way of example, fluids suitable for use by the ejector device can have very low viscosities, e.g., as with water at 1 cP, or less, e.g. 0.3 cP. The fluid may instead have viscosities in ranges up to 600 cP. More particularly, the fluid may have a viscosity range of about 0.3 to 100 cP, 0.3 to 50 cP, 0.3 to 30 cP, 1 cP to 53 cP, etc. In some implementations, the ejector device may be used to eject a fluid having a relatively high viscosity as a stream of droplets, e.g., a fluid having a viscosity above 1 cP, ranging from about 1 cP to about 600 cP, about 1 cP to about 200 cP, about 1 cP to about 100 cP, about 10 cP to about 100 cP, etc. In some implementations, solutions or medications having the suitable viscosities and surface tensions can be directly used in the reservoir without modification. In other implementations, additional materials may be added to adjust the fluid parameter. By way of example, certain fluids are listed below in Table 15:

TABLE 15

Viscosity measured at 20° C.

| drugs/fluids | dynamic viscosity (cP) | kinematic viscosity (cP) | density |
| --- | --- | --- | --- |
| water | 1.017 | 1.019 | 0.99821 |
| Xalatan ™ | 1.051 | 1.043 | 1.00804 |
| Tropicamide | 1.058 | 1.052 | 1.00551 |
| Restasis ™ | 18.08 | 17.98 | 1.00535 |

From the above discussion it will be appreciated that different configurations and material will result in different attributes. In order to assist in understanding some of these attributes in a few select embodiments of the ejector mechanism, experiments were conducted to compare certain embodiments. The experiments described herein should not, of course, be construed as specifically limiting the invention and such variations of the invention, now known or later developed, which would be within the purview of one skilled in the art are considered to fall within the scope of the invention as described herein and hereinafter claimed.

Example 6: Measurement of Mass Deposition

To measure the mass deposition of an ejector device, the ejector devise is clamped horizontally to eject material towards to the ground where the poled direction Z, as shown in FIG. 56, is toward to the ground (e.g., parallel to gravity). Referring to FIG. 55A, the direction 5514 of the ejected droplets 5512 is towards to the ground. A ground wire and positive wire of the device is connected to an operational amplifier and a current probe and voltage probe are connected to an oscilloscope.

The frequency region that provides for device spraying is initially determined by a frequency sweep through the range of 2 kHz to 500 kHz. The electrical data, including the voltage and current, are recorded and stored. Upon analysis, the spray ranges for mass deposition determination are selected. The results are plotted to provide a mass ejection profile as shown in FIG. 58, for example.

To determine the mass deposition, the frequency and voltage are set, for example, to a 90V peak to peak (90Vpp) sine wave at a frequency of 50 kilohertz (kHz) and the spray from the ejector device is measured 5 times on a 24 mm×60 mm No. 1 glass coverslip using a scale with a 1 milligram (mg) sensitivity and calibrated with a 1 mg class 1 weight with traceable certificate. For each measurement, the coverslip is placed on the scale and the scale is zeroed. The slide is place underneath the ejector device and the voltage applied for a defined period of time. The slide is returned to the scale and the mass is determined and recorded. The coverslip is cleaned, the scale re-zeroed before each measurement. A total of 5 measurements are recorded for each frequency. The process is repeated with the frequency incrementally changed based on a predetermined step size (normally 1 kHz).

Figure 59:
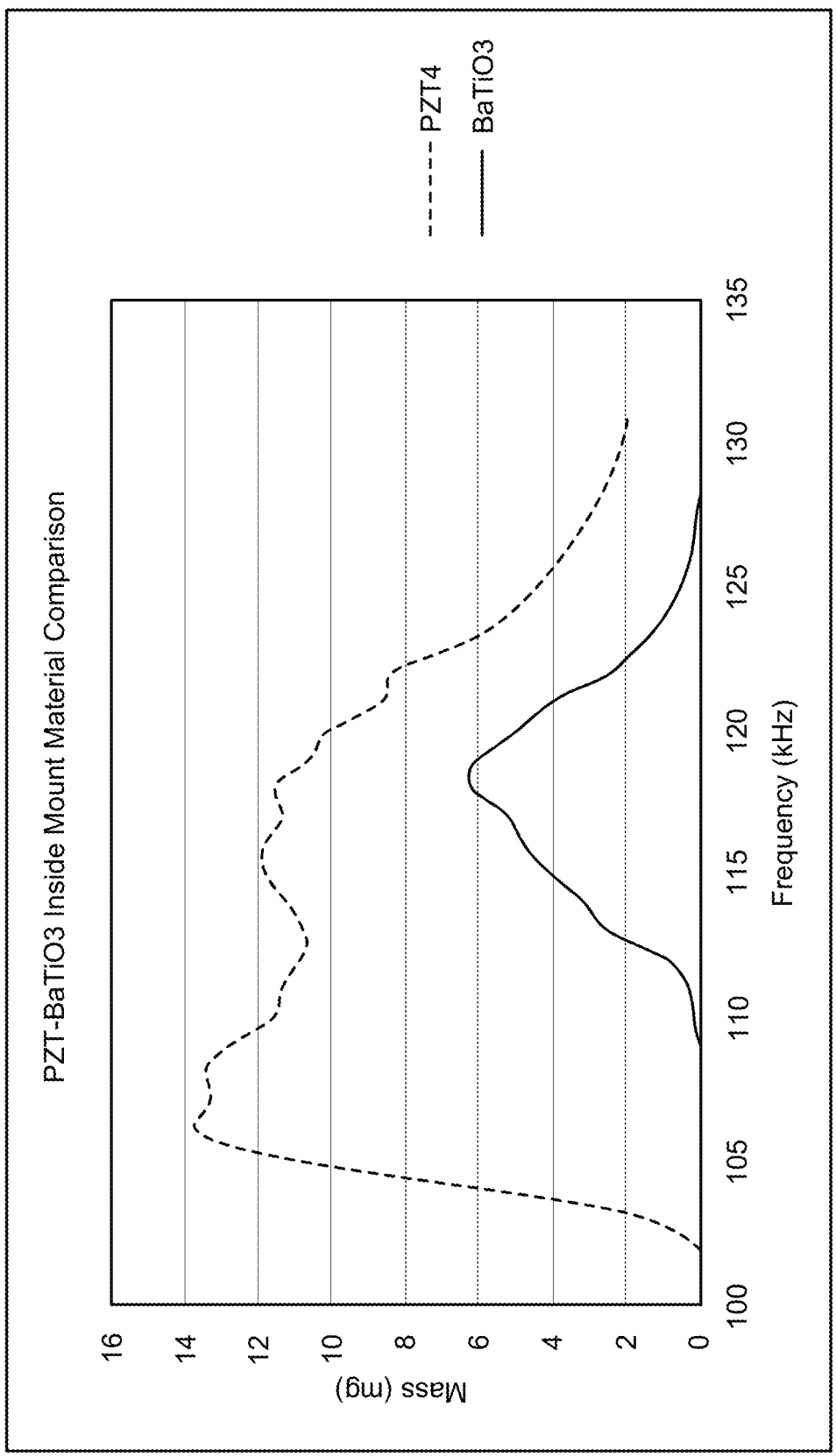
FIG. 59 illustrates a comparison of mass ejection for PZT and $BaTiO_3$ (lead free) piezoelectric actuator materials using an ejector assembly with an edge mounted piezoelectric actuator according to another embodiment of the disclosure.

Example 7: Comparison of PZT to BaTiO$_3$ Using an Inside Mount Ejector Assemblies The mass deposition profile of ejector devices having an inside mounted ejector assembly are determined using the method described in Experiment 6 above to determine the frequency region for device spraying. For both the PZT and BaTiO$_3$ piezoelectric materials, the piezoelectric actuator 5504 has a 16 mm outer diameter by 8 mm inner diameter, with a height of 550 um, mounted to a 20 mm diameter circular ejector plate 5502 50 um thick. In this embodiment, several samples of PZT are compared directly to BaTiO$_3$ with PZT ejecting more fluid than BaTiO$_3$ in approximately the ratio of the d33 coefficients of the materials. The only significantly ejecting mode is shown in FIG. 59.

Where the distance 5554 is greater than zero (here, 2 mm), the PZT material provides a broader range of effective frequencies when compared to BaTiO$_3$. The maximal mass ejection of the PZT-based ejector is more than twice the output of the BaTiO$_3$ ejector. While less efficient, the BaTiO$_3$ provides maximal mass ejection between 115 and 102 kHz of about 6 mg.

7a: Comparison of PZT and BaTiO$_3$ Using Edge Mounted Ejector Assemblies

Using the method of Experiment 6, mass ejection at different frequencies is determined using a frequency step size of 1 kHz, beginning at 10 kHz to 500 kHz. The mass deposited in milligrams is plotted versus the frequency and is shown in FIG. 58 for edge mounted PZT and BaTiO$_3$ piezoelectric actuators having a 20 mm outer diameter by 14 mm inner diameter of 550 um height piezoelectric on a 20 mm circular 50 um thick ejector plate 5502. In this case, several samples of PZT are compared directly to BaTiO$_3$ with PZT and BaTiO$_3$ ejecting nearly equivalently (adjusted for sample variation) even with vastly different material d33 coefficients. As is also apparent from FIG. 58, many modes are excited with equivalent performance between materials.

When PZT and BaTiO$_3$ piezoelectric actuators are edge mounted (that is, the distance 5554 is at or near zero), mass ejection occurs at discrete ranges of frequencies corresponding to the resonance coupling between the piezoelectric actuator and the coupled ejector plate 5502 and generator plate. While the PZT based device has a $D_{33}$=330 pC/N and the BaTiO$_3$ has a $D_{33}$=160 pC/N, the ejection profiles and efficiencies are very similar. The centro-symmetric design and edge mounting of the piezoelectric actuator overcomes the differences in displacement allowing a wide variety of piezoelectric materials to be incorporated into the ejection device.

7b: Effect of Decreasing Piezoelectric Actuator 5504 Diameter Relative to Ejector Plate 5502

As the piezoelectric actuator 5504 is shifted in from the edge of the ejector plate 5502 (e.g., the distance 5554 is increased from zero), performance is lost as the ejecting modes are increasingly damped by the piezoelectric stiffness. In one embodiment the piezoelectric was 20 mm outer diameter by 14 mm inner diameter with an optimized thickness of 250 um and an ejector plate diameter of 20 mm. It showed ejection exceeding all other cases by 20-33%. In another embodiment the outer diameter of the piezoelectric was altered to 19 mm and the ejector plate diameter was changed to 21 mm with an optimized thickness of 200 um. The ejection frequencies remain virtually the same, but opposed to the edge mounted case, ejection is reduced across every mode even though piezoelectric thickness is optimized, (thicknesses from 150 um to 550 um were lab tested in 25 um increments). In the third embodiment, the piezoelectric remained at 19 mm outer diameter and 14 mm inner diameter but the ejector plate was changed to 23 μm. Once again, the thickness was optimized to 175 μm to reduce stiffness but all modes are severely suppressed and performance was degraded over 80%.

Example 8: Comparison of BaTiO$_3$ Piezoelectric Materials

BaTiO$_3$ materials having differing properties were distinguished using Scanning Electron Microscopy (SEM). SEM images of two exemplary BaTiO$_3$ materials were obtained and showed a uniform particle size about 2 to 5 microns in diameter in the first sample and a fused structure with particles tens of microns in diameter in the second sample. While both samples had similar $D_{33}$ values, the smaller grain size improves performance by lowering the resonance frequencies.

Example 9: Modulation of Eigenmodes

For a circular ejector plate 5502 excited by a piezoelectric actuator 5504, increasing the stiffness of the piezoelectric actuator 5504 resulted in suppression of high frequency eigenmodes. To test the effects of increasing the stiffness of the piezoelectric actuator 5504, a first piezoelectric actuator 5504 of 200 um thickness having an outer diameter of 20 mm and an inner diameter of 14 (20 mm×14 mm) and a second piezoelectric actuator 5504 of 400 um thickness (20 mm×14 mm) were bonded to an ejector plate 5502 with an outer diameter of 20 mm (e.g., edge mounted). The normalized displacement of the two ejector mechanisms were [modeled or measured] at a frequency range from 1 Hz to $3\times10^5$ Hz. The greater flexibility of the thinner piezoelectric actuator 5504 allows for high frequency complex eigenmodes. In contrast, the thicker, stiffer piezoelectric actuator 5504 limits the eigenmodes to low frequency modes limited to the region of the ejector plate 5502 within the inner diameter of the piezoelectric actuator 5504 (e.g., inside 14 mm).

It will be understood that the ejector assembly described herein may be incorporated into an ejector device and system. Exemplary ejector devices and systems are illustrated in Ser. No. 13/712,784, filed Dec. 12, 2012, entitled "Ejector Mechanisms, Devices, and Methods of Use", Ser. No. 13/712,857, filed Dec. 12, 2012, entitled "High Modulus Polymeric Ejector Mechanism, Ejector Device, and Methods of Use", and Ser. No. 13/184,484, filed Jul. 15, 2011, entitled "Droplet Generator Device", the contents of which are herein incorporated by reference in their entireties.

When fluid is exposed to an air interface, it will evaporate into the air, causing a loss over time of fluid volume. If the fluid has any mineral elements that are left behind, the mixture contents change over time which results in crystallization at the air-fluid interface. However, if a small air volume around the fluid-air interface is sealed, the evaporation rate and crystallization rate drop to the leak rate of the seal, thereby reducing or eliminating evaporation and crystallization. Contamination is also possible whenever a device is open to the environment.

In part to address these issues, the present disclosure provides an auto-closing system for use with a droplet ejection device, which prevents the device from being open to the environment for any longer that the actual droplet ejection period, which greatly reduces the risk of contamination. In certain embodiments, the auto-closing system is dimensionally compact along the path of fluid ejection, uses a minimum of components, and provides a consistent seal in the presence of component dimensional variance. The system provides for a closed, sealed position and an open, active position used for fluid ejection. The change between closed and open positions can be configured for manual actuation by a user, or can be configured for powered actuation. In certain embodiments, the system may provide a manual configuration with low actuation force. Furthermore, movement between sealed and open positions can be configured for linear actuation or for rotary actuation. For instance, certain embodiments provide a linear actuation configuration used in conjunction with a user-operated, hinged activation button.

Figure 60:
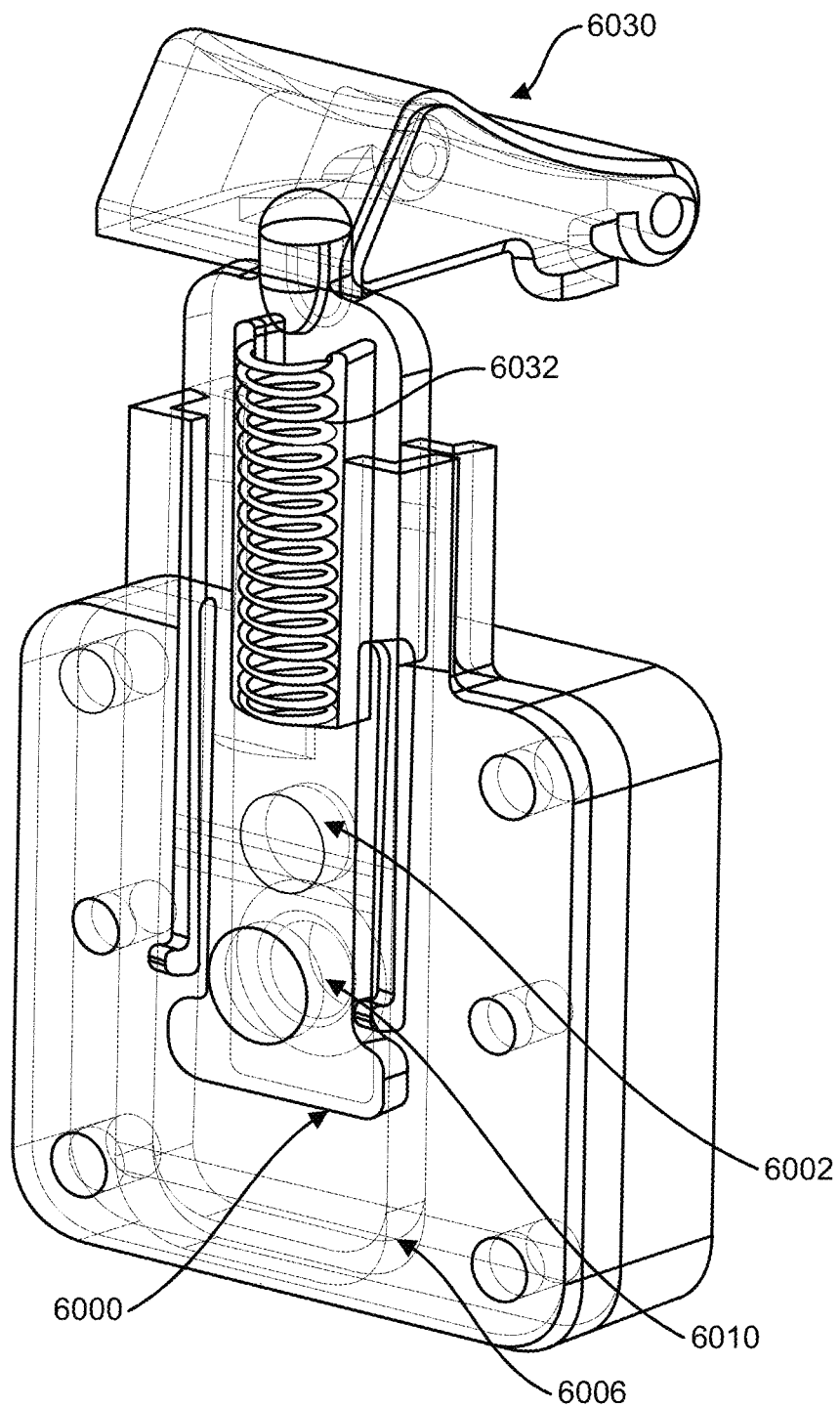
FIG. 60 shows a three dimensional transparent view of one embodiment of an ejector assembly with auto-closing system of the disclosure.
Figure 61:
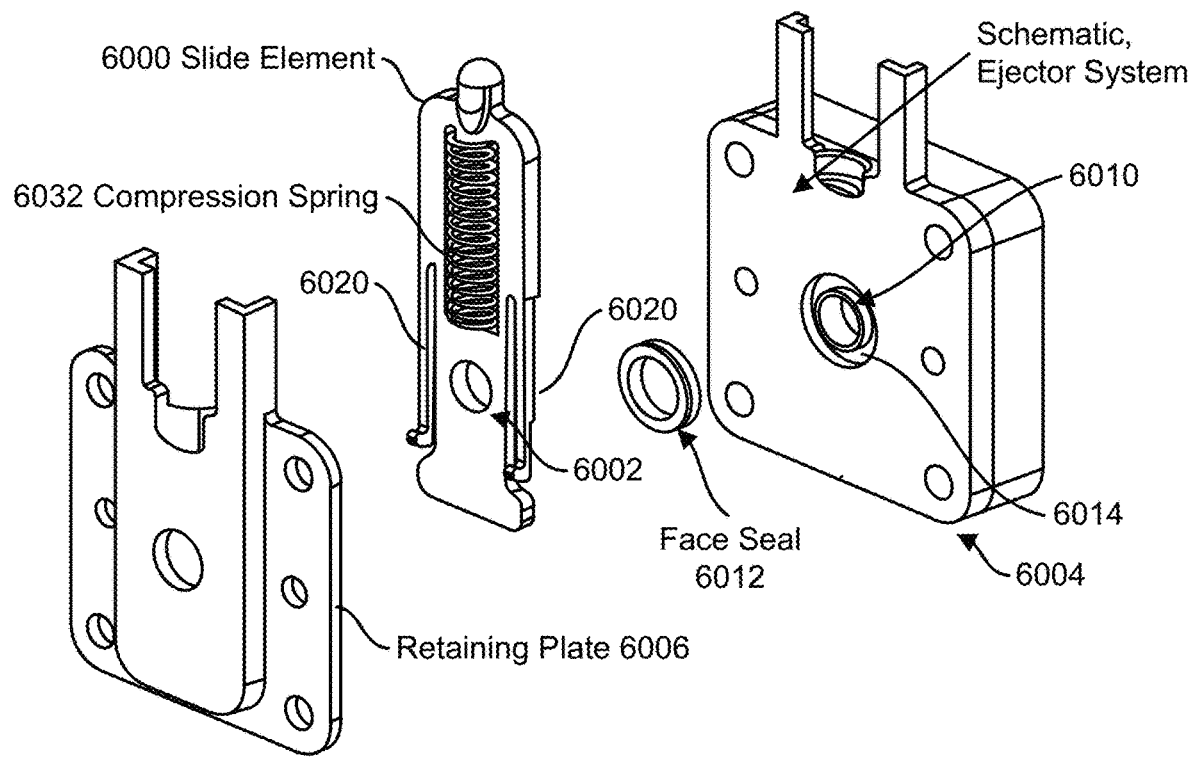
FIG. 61 shows the ejector assembly with auto-closing system of FIG. 60 in a dismantled state.

FIGS. 60-65 show one embodiment of an auto-closure system of the disclosure. FIG. 60 shows a compact, linearly actuated embodiment of an auto-closing system of the disclosure, and FIG. 61 shows an exploded assembly view of the main components of this embodiment.

As shown in FIGS. 60 and 61, a slide element 6000 with an aperture 6002 is retained between the ejection system 6004 to be sealed and a retaining plate 6006. The ejection system is shown schematically without reference to internal features. The face of the ejection system has a round aperture 6010 surrounded by a round, elastomeric face seal 6012. The face seal resides in a gland or groove 6014 in the face of the ejector. In one embodiment, the slide element is squeezed against the face seal by flexures 6020 integral to the slide element. The flexures could alternatively be located on the retaining plate or could be incorporated as a separate component. In one position of the slide element (the open position) the slide aperture 6002 is aligned with the ejector aperture 6010 for fluid dispensing. In the closed position the slide element aperture 6002 and ejection system aperture 6010 are fully non-aligned and the ejection system is sealed. A hinged activation button 6030 (FIG. 60) pivots about a fulcrum 6031 connected to a housing (not shown). The button 6030 is finger operated by the user and actuates the slide element in the downward direction to open the seal. Upon removal of user finger pressure, a compression spring 6032 returns the slide element 6000 to the closed and sealed position.

Figure 62:
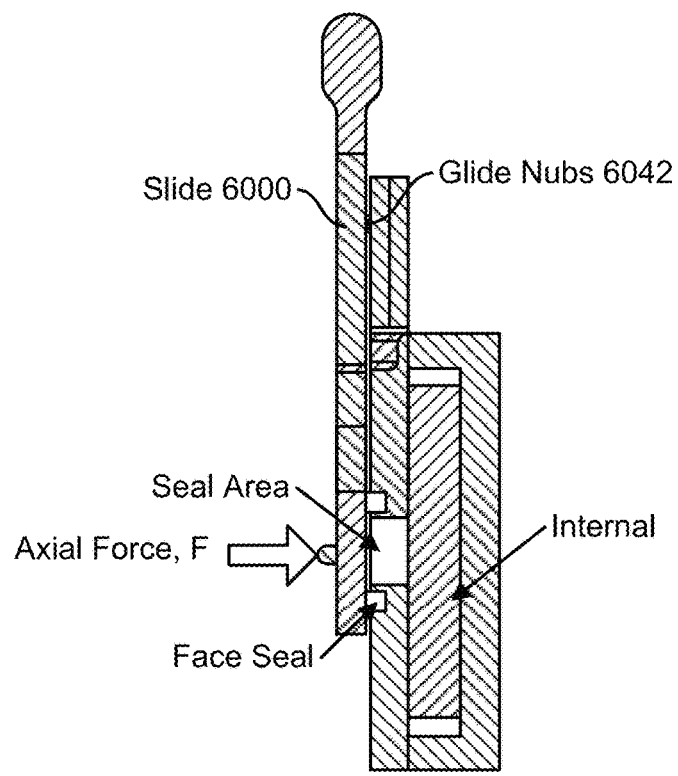
FIG. 62 is a sectional side view of part of the ejector assembly with auto-closing system of FIG. 60.
Figure 63:
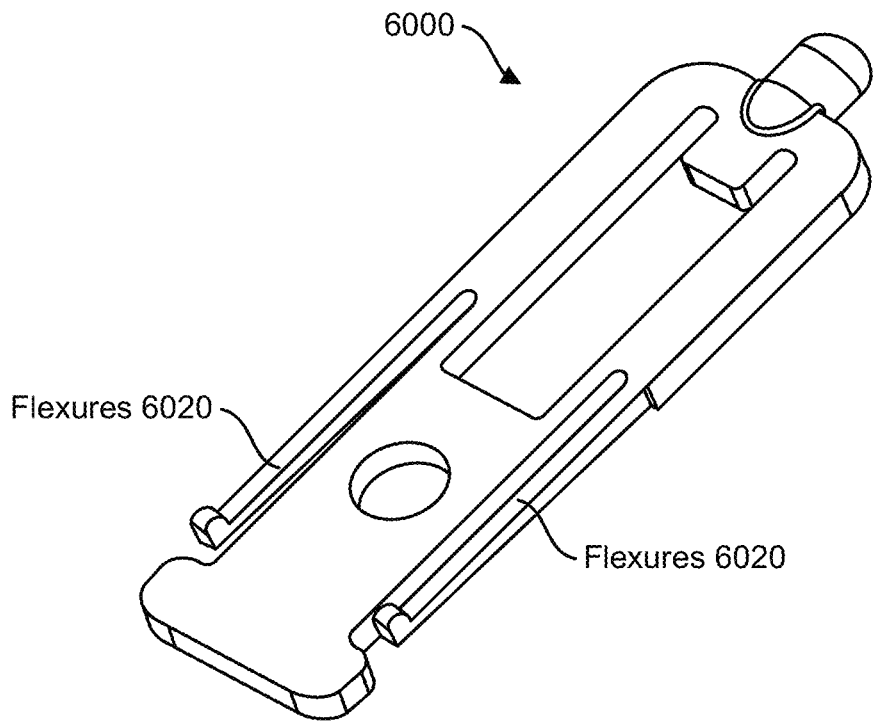
FIG. 63 shows three-dimensional front view of a sliding unit of the self-closing system of FIG. 60.
Figure 64:
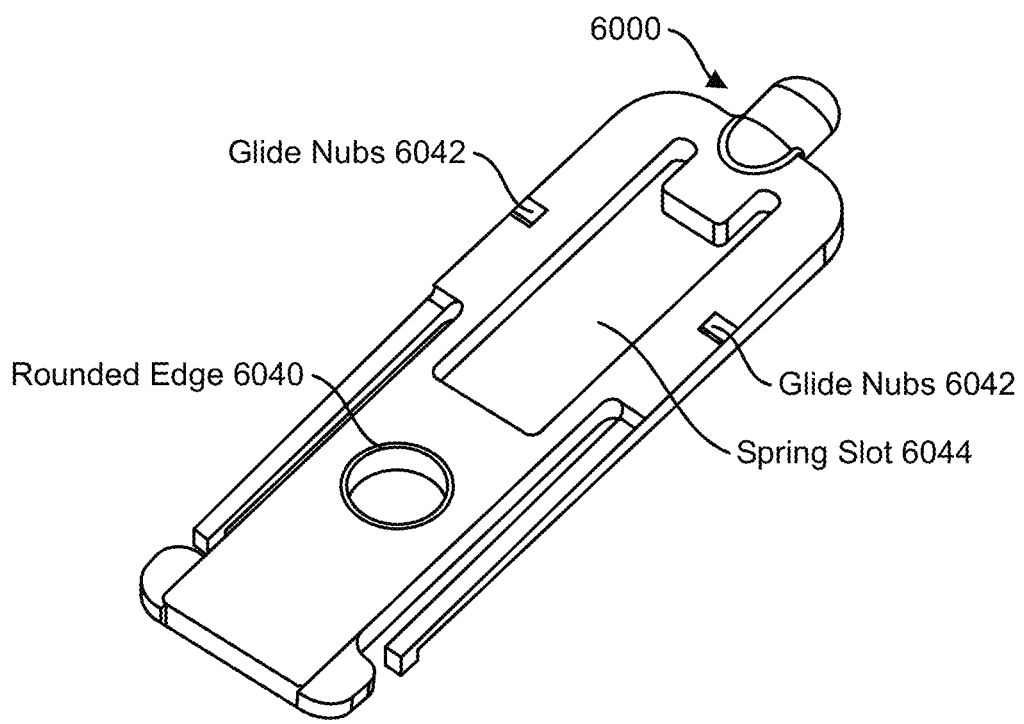
FIG. 64 shows three-dimensional back view of the sliding unit of FIG. 63.
Figure 65:
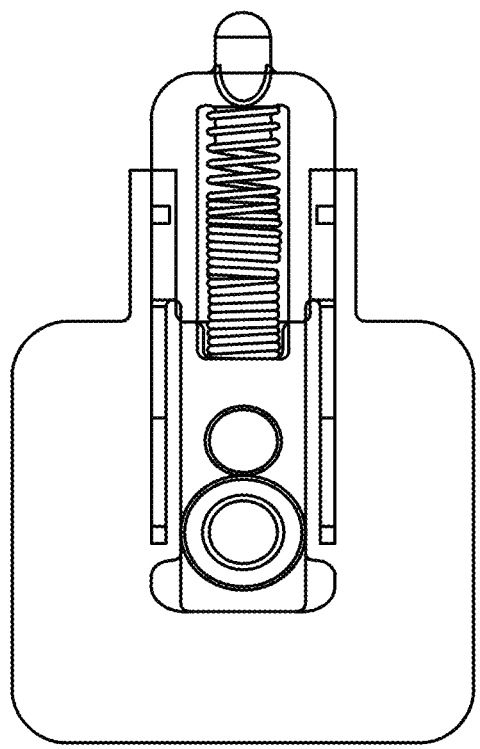
FIG. 65 is a front view of the auto-closing unit of FIG. 60 in a closed position.

FIG. 62 shows a schematic cross-sectional view of the auto-closing system and demonstrates the basic sealing principle. An axial force, F, presses the slide element against the elastomeric face seal located within the gland on the face of the ejection system. The face seal surface protrudes from the surface of the ejection system by approximately 20% of the seal cross section. The maximum anticipated internal pressure in the ejection system is countered by the axial squeezing force, F, such that the squeeze force exceeds the internal pressure force given by the product of the internal pressure P and the seal area A. For this embodiment, the axial force was chosen to be approximately 2× the anticipated internal pressure force. In the preferred embodiment, the axial squeeze force is provided by compact flexures 6020 as shown in FIGS. 63 and 64. The flexures 6020 provide a consistent force on the seal that is not sensitive to manufacturing variance in the dimensions of the components. Having the flexures integral to the slide element provides a minimum stack-up height from the ejection system to the aperture of the retaining plate, allowing the face of the ejection system to be closer to the final delivery point. To minimize actuation force the face seal 6012 is formed from a pre-lubricated silicone. To prevent abrasion, the slide element 6000 is always in contact with the seal. No edge of the slide element 6000 travels off and back onto the seal 6012; only the slide aperture edges traverse the face seal. To further prevent abrasion and reduce actuation force, the slide aperture edge 6040 is rounded and the top edges of the face seal are rounded. To keep the slide element parallel to the face seal, small glide nubs 6042 are provide on the slide element as shown in FIGS. 63 and 64.

The slide element in the preferred embodiment is injection molded from an anti-microbial thermoplastic. However, the disclosure is not so limited, and any suitable material may be used. As discussed, flexures 6020 integral to the slide 6000 provide the pre-load force on the face seal. Flexure geometry is chosen to provide the desired axial force without over-stressing the thermoplastic. In particular, the maximum stress in the flexure when fully deflected is chosen to be below the long-term creep limit of the chosen thermoplastic. This ensures that the desired face seal pre-load is achieved long-term, after the device has been assembled, without stress relaxation in the flexures. For compactness, the compression spring 6032 for auto-closing the device is located in a slot 6044 within the bounds of the slide element 6000. As mentioned above, two glide nubs 6042 are located on the of the slide element 6000 to keep the slide element 6000 parallel to the face seal, as the exposed face seal surface protrudes above the guide surface on the ejection system that constrains the back side of the slide element 6000.

As described above, the axial force on the face seal is chosen to exceed the anticipated internal pressure force by some margin of safety. In the event the axial force required exceeds the force that can be provided by small plastic flexures, an alternative approach is to use a separate spring component, which could be formed from steel. Long term creep issues are not present with a steel leaf spring and the exerted force can be increased to provide significant advantages, but with an increase in the cost and space required due to the separate part. One approach to address this problem is to use the compression spring 6032 for a secondary purpose as well. The primary purpose of the compression spring would be to provide the auto-closing feature of the device. When user finger pressure is removed from the activation button, the compression spring returns the device to the closed and sealed position, passively, without user interaction. To maintain a fully closed device, the geometry of the device is set such that the compression spring is in a pre-loaded state when the slide element is in its fully closed position. This pre-load can be used for the secondary purpose of increasing the axial force on the face seal, a feature employed in the present embodiment.

Figure 66:
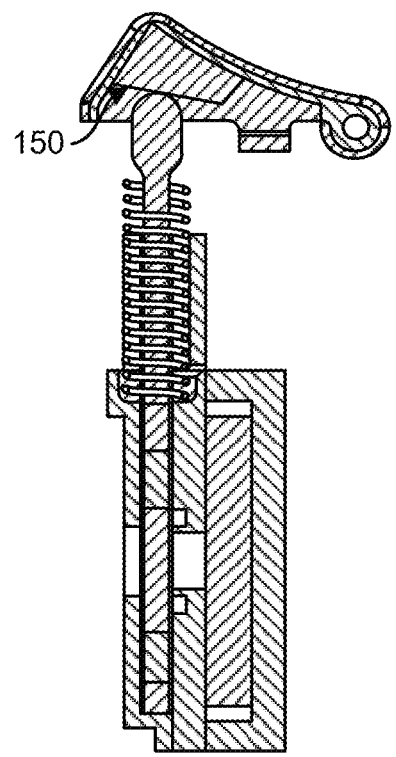
FIG. 66 is a sectional side view of the auto-closing unit of FIG. 60 in a closed position.
Figure 67:
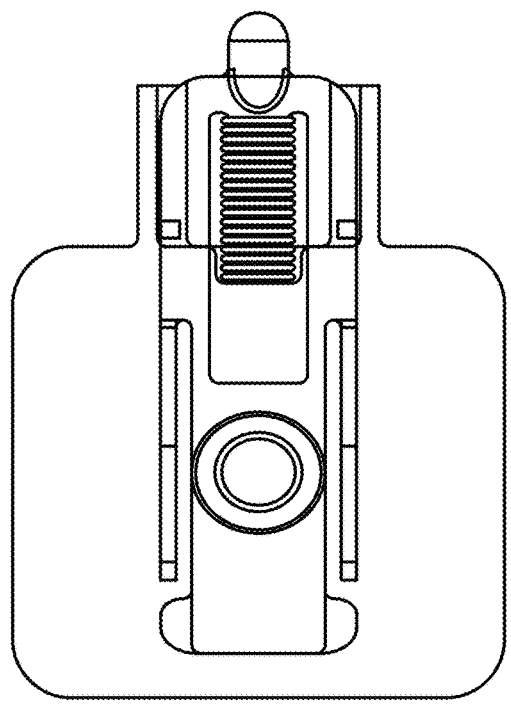
FIG. 67 is a front view of the auto-closing unit of FIG. 60 in an open position.
Figure 68:
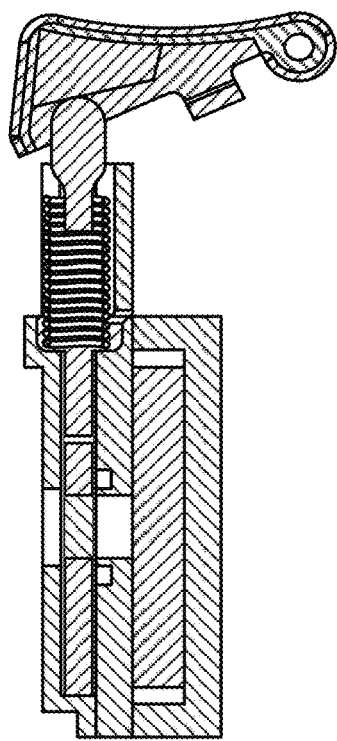
FIG. 68 is a sectional side view of the auto-closing unit of FIG. 60 in an open position.

As shown in FIG. 66, in the closed position the activation button 6030 interacts with the slide element on an angled, inclined surface 6050. This angle results in a horizontal outward force component acting on the top of the slide element 6000. A small fulcrum feature (not shown) is integrated into the top of the retaining plate. The fulcrum is a small raised portion interacting with the front face of the slide element. In the presence of the horizontal force vector, the slide element 6000 pivots about the fulcrum causing the lower part of the slide element 6000 to pivot toward the face seal to thereby increase the axial force on the face seal. This increases the seal integrity without the addition of added parts or increased space requirement. Furthermore, the axial force on the face seal is no longer solely dependent on the flexures, allowing a wider choice of thermoplastics with lower modulus (stiffness) values.

FIGS. 65-68 show a complete schematic representation of one embodiment in both closed (left) (FIGS. 65 and 66) and open (right) (FIGS. 67 and 68) positions, with implementation of all features described above. In certain embodiments, the auto-closing system includes umbrella valves or other suitable pressure relief means utilized in connection with the retention plate (also referred to herein as a compression plate) in order to address vapor pressure build-up. By way of non-limiting example, alternative pressure relief systems may include: duckbill valves; umbrella/duckbill 2-way valves; other suitable pressure release valves; pinhole valve in a silicone sheet; slit valve in silicone sheet; single pinhole/vent hole in a rigid material (e.g., 50 micron diameter hole in 50 micron thick stainless steel); an array of vent holes; or any other suitable pressure relief means that can restore pressure equilibrium quickly enough, while also preventing excess evaporation due to vapor pressure. Aspects of the umbrella valves or pressure relief means are discussed in further detail herein.

Example 10: Measurement of Crystallization, Evaporation, and Sealing

Crystallization occurs, especially in small holes where the evaporation rate is high, at rates that can be prohibitive to operation of a droplet ejector device. If crystallization occurs, it prevents droplet ejection out of ejector openings by blocking flow.

In accordance with one embodiment, for a generator plate with of 20 um wide holes 50 microns deep with no puncture/capillary plate and openly exposed to the environment, FIGS. 69 (a)-(c) shows the crystal growth over time for isotonic saline solution. In FIG. 69(a), the ejector openings are shown at time zero (fluid has just been inserted into a hard reservoir that is sealed to the ejector mesh (which defines multiple ejector openings) and shows no crystallization. A stack compression plate sealingly engages the mesh screen by means of an O-ring and the opposite surface of the mesh screen is attached via an O-ring to a reservoir, the assembly being held together with screws and nuts. At 50 seconds after fluid is inserted, shown in FIG. 69(b), noticeable crystallization begins to form in the ejector nozzles (holes). At 3 minutes, shown in FIG. 69(c), a number of ejector openings or holes are completely occluded and several ejector nozzles (holes) exhibit crystal growth. The images were acquired by transmission light microscopy, wherein crystals occlude transmitted light through openings.

In order to demonstrate the effect of a fluid loading plate, a system was similarly set up, composed of a mesh screen of a generator plate with 20 um wide holes 50 microns deep, but in this case a capillary plate was added and openly exposed to the environment. FIGS. 70(a)-(c) show the crystal growth over time for isotonic saline solution. In FIG. 70(a), the ejector openings are shown at time zero (fluid has just been inserted into a hard reservoir that is sealed to the ejector mesh via the following: a stack compression plate, O-ring, mesh screen, O-ring, puncture/capillary plate, O-ring, reservoir held together with screws and nuts) and no crystallization has occurred. At 5 minutes, shown in FIG. 70(b), still no crystallization has formed. At 6 hours, shown in FIG. 70(c) a number of ejector openings are completely occluded and several ejector openings exhibit crystal growth. Although the puncture/capillary plate cannot reduce the evaporation, it reduces crystallization. The decrease in crystallization rate is obtained by delivering a constant fluid supply, and preventing mineral deposits not immersed in fluid.

Evaporation may in certain applications lead to changes in drug strength and potency, e.g., through loss of water and resulting change in concentration. Evaporation can also lead to crystallization in ejector openings. Table 16 shows evaporation rates from the auto-closure system of the present disclosure versus evaporation rates with two types of umbrella valves with different cracking pressures provided in the fluid loading plate. The evaporation rates shown are those exhibited without valve cracking due to pressure fluctuation for isotonic saline using one type of valve, and for latanoprost and isotonic saline using a different valve. Both valves showed very high evaporation rates. In contrast, the auto-closure systems of the present disclosure resulted in a decrease in evaporation rate by a factor of 7-10, depending on the test fluid. This also resulted in an extension of crystallization time by a factor of 7-10 in between sprays compared to the puncture/capillary plate and umbrella valves alone.

TABLE 16

Umbrella valve evaporation rates versus perfect face seal using auto-closure system.

| Fluid | Umbrella Valve | Mass Lost in 1 day (mg) | Predicted Mass Lost in 30 days (mg) | Predicted % fluid lost from 2.0 mL ampoule in 30 days |
|---|---|---|---|---|
| Isotonic Saline | 5.3 mm (0.1-0.2 PSI vent pressure) | 23.6 | 707 | 35% |
| Isotonic Saline | | 18.0 | 539 | 27% |
| Isotonic Saline | | 20.4 | 613 | 31% |
| Latanoprost | 5.8 mm (0.2-0.3 PSI vent pressure) | 3.5 | 104 | 5% |
| Latanoprost | | 8.6 | 258 | 13% |
| Isotonic Saline | | 11.7 | 351 | 18% |
| Latanoprost | | 7.5 | 224 | 11% |
| Isotonic Saline | Perfect Seal | 2.4 | 72 | 4% |
| Latanoprost | | 2.6 | 79 | 4% |

In certain aspects of the disclosure, auto-closure systems were utilized in order to prevent large pressure excursions from forcing fluid out of the ejector system. Valves equalize pressure nearly instantly if the pressure exceeds the cracking pressure.

Alternatives to umbrella valves are within the scope of the present disclosure. In this regard, any suitable manner for equalizing pressure while preventing evaporation may be utilized, e.g., a 50 um and 100 um vent hole solution with a bacteria and fluid resistant membrane filter bonded over the vent hole. This solution also equalizes pressure almost instantly, 10 psi/0.25 cc per second of air, but also reduces evaporation rates 10-20 times below that of the umbrella valves, as shown in Table 17. Leak rates for pressure equalization (not evaporation) are also shown in Table 17.

TABLE 17

Evaporation and Leak rates for pressure equalization of filtered vent holes

| Condition | Average mass loss per day (mg) | Standard Deviation (mg) | Number of samples |
|---|---|---|---|
| 50 um hole | 1.3 | 0.3 | 4 |
| 50 um hole & 1.2 um membrane | 0.9 | 0.2 | 3 |

Leak rates from 50 um hole in SS316 steel, 50 um thick (Sample size: N = 10 for each condition)

| Condition | Average Leak Rate (cm^3/sec) | Corrected Leak Rate (cm^3/sec) | Standard Deviation (cm^3/sec) |
|---|---|---|---|
| No 50 um hole (SS316 plate) | 0.035 | 0 | 0.004 |
| 50 um hole | 0.431 | 0.40 | 0.08 |
| 50 um hole & 1.0 um membrane (PTFE on non-woven polyester LHOP support) | 0.428 | 0.39 | 0.06 |
| 50 um hole & 1.2 um membrane (acrylic copolymer on non-woven nylon support) | 0.473 | 0.44 | 0.13 |

The auto-closure system provides an air and pressure barrier necessary to prevent evaporation of fluid which could lead to crystallization in the ejector openings. The purpose of this experiment was to determine the normal force necessary to produce an auto-closure system seal capable of sealing at 1.00 PSI.

Using the gravitational force of a plastic sealing element upon the silicone face sealing ring to determine face seal quality as a function of normal force. An ABS/Polycarbonate plastic seal element was attached to the bottom of a beaker so that water could be added for variable mass. The self-lubricating silicone seal was housed inside the compression plate, with a pressure regulator and pressure gauge attached to the inside of the compression plate. The variable mass sealing element was balanced upon the silicone seal, and fluid was added to the beaker. Pressure data was recorded as a function of face seal normal force.

As gauge pressure approached 1.00 PSI, the auto-closure system seal mass was increased. Normal forces of 40 grams and larger typically sealed at 0.90 PSI or greater. This was identified as an acceptable seal because it is significantly higher than the 0.2 PSI umbrella valve venting pressure.

Another identified condition was that the frictional force of the closing slider upon the auto-closure system should be less than the restoring force of the auto-closure spring. This condition was fulfilled by choosing a spring with a sufficient spring constant and displacement.

To measure the seal quality provided by the interior auto-closure system seal over a sequence of multiple sliding actuations. An auto-closure system according to the disclosure was attached to an air pressure regulator and pressure gauge. The regulator was set to 1.00 PSI with a perfect seal, and then the perfect seal is removed. The auto-closure is actuated to provide a seal, and the gauge pressure inside the seal increased until it reached a maximum pressure. This maximum equilibrium pressure is recorded as the seal pressure for that trial.

The maximum equilibrium pressure was recorded for 20 trials, whereafter the auto-closure system was actuated 100 times. This process was repeated 3 more times, resulting in 4 data sets of 20 trials, with 100 actuations between each data set. This was designed to test the auto-closure system repeatability over a total of 380 slide actuations. The average seal pressure for each data set is shown in Table 18.

TABLE 18

Auto-closure face seal testing over 380 actuations

| Data Set # (N = 20 actuations) | Average Seal Pressure (PSI) |
|---|---|
| 1 | 0.940 ± 0.006 |
| 2 | 0.937 ± 0.007 |
| 3 | 0.934 ± 0.005 |
| 4 | 0.936 ± 0.005 |

Note:
Maximum seal pressure is 1.00 PSI because of regulator

A 1.00 PSI seal was identified as an acceptable face seal because it provides a safety margin above the 0.2 PSI umbrella valve vent. The data from this test was consistently within 6-7% of this target sealing pressure over 380 total actuations.

Many implementations of the inventions disclosed in the present application and the above applications that are incorporated by reference have been disclosed. This disclosure contemplates combining any of the features of one implementation or embodiment with the features of one or more of the other implementations or embodiments. For example, any of the ejector mechanisms or reservoirs can be used in combination with any of the disclosed housings or housing features, e.g., covers, supports, rests, lights, seals and gaskets, fill mechanisms, or alignment mechanisms.

Further variations on any of the elements of any of the inventions within the scope of ordinary skill are contemplated by this disclosure. Such variations include selection of materials, coatings, or methods of manufacturing. Any of the electrical and electronic technology can be used with any of the implementations without limitation. Furthermore, any networking, remote access, subject monitoring, e-health, data storage, data mining, or internet functionality is applicable to any and all of the implementations and can be practiced therewith. Furthermore, additional diagnostic functions, such as performance of tests or measurements of physiological parameters may be incorporated into the functionality of any of the implementations. Performance of glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms. For example, the device or base may be equipped with or coupled to an iris or retina scanner to create a unique identification to match a device to the user, and to delineate between eyes. Alternatively, the device or base may be coupled to or include sophisticated imaging devices for any suitable type of photography or radiology.

What is claimed is:

1. A removable ejector assembly and reservoir for an ejector device, comprising:
   a reservoir containing a fluid;
   an ejector mechanism having a generator plate and a piezoelectric actuator;
   a fluid loading plate spaced apart from a rear surface of the ejector mechanism so as to form a fluid retention area at the rear surface of the ejector mechanism; and
   an ejector mechanism/fluid loading plate interface and a fluid reservoir/fluid loading plate interface which directly or indirectly attaches the fluid loading plate to the ejector mechanism and the reservoir, respectively;
   one or more fluid channels for channeling the fluid from the fluid reservoir to the fluid retention area at the rear surface of the ejector mechanism;
   at least one needle for transferring the fluid from the reservoir to the ejector mechanism; a first mating portion including the at least one needle and being coupled to the ejector mechanism, the first mating portion forming a receptacle; and
   a second mating portion attached to the reservoir and configured to be coupled to the receptacle of the first mating portion, the second mating portion being inserted into the receptacle of the first mating portion, the second mating portion including a puncturable sealing element;
   wherein:
   the generator plate includes a plurality of openings formed through a thickness, the piezoelectric actuator being operable to oscillate the generator plate at a frequency to generate a directed stream of droplets when the ejector mechanism is activated during use; and
   the fluid loading plate being placed in a parallel arrangement with the ejector mechanism so as to form a capillary separation between the fluid loading plate and the ejector mechanism, wherein the capillary separation generates a capillary fluid flow between the fluid loading plate and the ejector mechanism via the one or more fluid channels at the rear surface of the ejector mechanism so as to channel the fluid from the fluid reservoir to the fluid retention area at the rear surface of the ejector mechanism during use, the fluid loading plate and the ejector mechanism being separated by a distance of 0.2 mm to 0.5 mm so as to form said capillary separation.

2. The removable ejector assembly and reservoir for an ejector device of claim 1, wherein:
the ejector mechanism has an ejector plate coupled to the generator plate and the piezoelectric actuator.

3. The removable ejector assembly and reservoir for an ejector device of claim 1, wherein:
the ejector mechanism and reservoir are configured to be removably mounted to a housing of an ejector device having electronics and a power source for controlling the ejection of the fluid from the ejector mechanism.

4. The removable ejector assembly and reservoir for an ejector device of claim 1, wherein: the first mating portion has a wall that surrounds the at least one needle and defines the receptacle that receives the second mating portion.

5. The removable ejector assembly and reservoir for an ejector device of claim 1, wherein: the puncturable sealing element is formed from a self-sealing material such that the puncturable sealing element self-seals following puncturing by the at least one needle of the first mating portion during use.

6. The removable ejector assembly and reservoir for an ejector device of claim 1, further comprising: a fitment connected to the reservoir, the fitment defining a secondary reservoir fluidly coupled to the fluid in the reservoir, the fitment also having the second mating portion and the seal.

7. The removable ejector assembly and reservoir for an ejector device of claim 1, wherein: the first mating portion is snap-fit to the second mating portion.

8. The removable ejector assembly and reservoir for an ejector device of claim 1, wherein: the at least one needle is movable relative to the seal to move the at least one needle through the puncturable sealing element to fluidly couple the reservoir to the fluid retention area through the at least one needle.

9. The removable ejector assembly and reservoir for an ejector device of 1, wherein the directed stream of droplets have an average directed droplet diameter greater than 15 microns.

* * * * *